(12) United States Patent
Vom et al.

(10) Patent No.: US 11,276,482 B2
(45) Date of Patent: Mar. 15, 2022

(54) METHOD AND SYSTEM FOR PATIENT AND BIOLOGICAL SAMPLE IDENTIFICATION AND TRACKING

(71) Applicant: GENEA IP HOLDINGS PTY LIMITED, Sydney (AU)

(72) Inventors: Eduardo Vom, Box Hill (AU); Jeremy Phillip Stimson, Fitzroy (AU); Yassaman Pouladi, Box Hill (AU); Ben Hobbs, Box Hill (AU); Tammie Kim Roy, Glenmore Park (AU); Jan Kirsten, Bamberg (DE)

(73) Assignee: GENEA IP HOLDINGS PTY LIMITED, Sydney (AU)

( * ) Notice: Subject to any disclaimer, the term of this patent is extended or adjusted under 35 U.S.C. 154(b) by 0 days.

(21) Appl. No.: 15/735,269

(22) PCT Filed: Jun. 14, 2016

(86) PCT No.: PCT/AU2016/000201
§ 371 (c)(1),
(2) Date: Dec. 11, 2017

(87) PCT Pub. No.: WO2016/197183
PCT Pub. Date: Dec. 15, 2016

(65) Prior Publication Data
US 2018/0174670 A1    Jun. 21, 2018

(30) Foreign Application Priority Data

Jun. 12, 2015   (AU) ................................ 2015902235

(51) Int. Cl.
*H04W 4/80* (2018.01)
*G16H 10/40* (2018.01)
(Continued)

(52) U.S. Cl.
CPC ............. *G16H 10/40* (2018.01); *G06Q 10/08* (2013.01); *G16H 10/60* (2018.01); *G16H 10/65* (2018.01);
(Continued)

(58) Field of Classification Search
CPC ...... C12M 41/46; C12M 21/06; C12M 23/12; C12M 23/20; C12M 23/50; C12M 41/14;
(Continued)

(56) References Cited

U.S. PATENT DOCUMENTS

2006/0057555 A1* 3/2006 Damari .................. C12M 21/06
435/4
2006/0213964 A1* 9/2006 Excoffier ......... G01N 35/00732
235/375
(Continued)

FOREIGN PATENT DOCUMENTS

WO    2014131091    9/2014

*Primary Examiner* — Hai Phan
*Assistant Examiner* — Anthony D Afrifa-Kyei
(74) *Attorney, Agent, or Firm* — Eversheds Sutherland (US) LLP

(57) ABSTRACT

The present invention provides a device and system for monitoring the accuracy of procedures in the course of the performance of a task, the task comprising at least one procedure to be performed, the device comprising: an input interface for receiving input data relating to the procedures; a data store for storing data relating to the procedures; a processor for: comparing the input data with the stored data;
(Continued)

and generating a comparison result indicating the result of that comparison; and an output interface for outputting the comparison result.

9 Claims, 52 Drawing Sheets

(51) Int. Cl.
    *G16H 10/65*     (2018.01)
    *G16H 10/60*     (2018.01)
    *G06Q 10/08*     (2012.01)
    *G01N 35/00*     (2006.01)
    *G01N 35/04*     (2006.01)
    *A61D 19/02*     (2006.01)

(52) U.S. Cl.
    CPC ............... *H04W 4/80* (2018.02); *A61D 19/02* (2013.01); *G01N 2035/00831* (2013.01); *G01N 2035/00881* (2013.01); *G01N 2035/0493* (2013.01)

(58) Field of Classification Search
    CPC ....... C12M 41/34; C12M 41/36; G02B 21/02; G02B 21/30; G02B 21/34
    See application file for complete search history.

(56) References Cited

U.S. PATENT DOCUMENTS

| | | | |
|---|---|---|---|
| 2007/0124278 A1 | 5/2007 | Lewis, Jr. et al. | |
| 2009/0123419 A1* | 5/2009 | Sherman | A61K 31/166 424/85.4 |
| 2009/0131529 A1* | 5/2009 | Sherman | A61K 31/166 514/619 |
| 2010/0291618 A1* | 11/2010 | Robinson | C12Q 1/24 435/34 |
| 2012/0004853 A1* | 1/2012 | Oeltjen | G16H 10/40 702/19 |
| 2012/0100546 A1* | 4/2012 | Lowery, Jr | G01R 33/281 435/6.12 |
| 2013/0072748 A1* | 3/2013 | Hamamah | C12Q 1/6837 600/34 |
| 2013/0079599 A1* | 3/2013 | Holmes | G16H 10/40 600/300 |
| 2013/0337487 A1* | 12/2013 | Loewke | G06T 7/0016 435/29 |
| 2014/0187448 A1* | 7/2014 | O'Banion | G01N 35/00732 506/39 |
| 2014/0234949 A1* | 8/2014 | Wasson | G01N 35/00871 435/287.2 |
| 2014/0335193 A1* | 11/2014 | Rintoul | A61K 9/1694 424/501 |
| 2018/0174670 A1* | 6/2018 | Vom | G06Q 10/08 |

* cited by examiner

Thaw workflow

Female's label on embryology paperwork is scanned at every ID check unless otherwise stated Cryotop

*Embryologist takes photos of cane*

OR

Gavi

*Embryologist takes photos of Gavi pod*

Thaw dish (2 dishes used for Cryotop)

→

CMFET or BMFET Dish (CM/BM frozen embryo transfer)

METHOD AND SYSTEM FOR PATIENT AND BIOLOGICAL SAMPLE IDENTIFICATION AND TRACKING

RELATED APPLICATIONS

This application claims priority to Australian Provisional Patent Application No. 2015902235 in the name of Genea Ltd, which was filed on 12 Jun. 2015, entitled "Method and System for Patient and Biological Sample Identification and Tracking" and the specification thereof is incorporated herein by reference in its entirety and for all purposes.

FIELD OF INVENTION

The present invention relates to the field of identifying, monitoring and tracking biological materials and/or samples.

In one form, the invention relates to the identification, monitoring and tracking of biological material obtained from persons who are undergoing medical, or medical-related procedures. It is particularly suited to the identification, monitoring and tracking of biological material obtained from women and men in the course of assisted reproduction technology (ART) treatment, and in particular, of their gametes and embryos.

It will be convenient to hereinafter describe the invention in relation to persons who are undergoing ART treatment, however it should be appreciated that the present invention is not limited to that use, only.

BACKGROUND ART

Assisted reproductive technology (ART) is becoming increasingly important in developed countries as a means of assisted reproduction. By way of background, after being introduced into the United States in 1981, approximately 150,000 ART cycles were performed in that country during 2010, resulting in 47,090 live births and 61,564 infants. Although the use of ART is still relatively rare as compared with the potential demand, use has increased vastly over the past decade, such that today approximately 1% in the US and 2-4% in others countries of all infants born every year are conceived using In Vitro Fertilization (IVF).

IVF involves hormone stimulation of a woman's ovaries to mature multiple eggs, followed by collection of unfertilized eggs from the patient's ovaries and fertilisation with sperm from the woman's partner or the donor. The fertilised eggs (embryos) are then cultured for 2-6 days before being transferred back into her uterus for gestation. Clearly, it is important for the procedure to be administered under a rigorous and carefully-controlled protocol to ensure that the eggs are fertilised with sperm from the intended partner. Various instances have been reported in the media concerning unintended and highly distressing mix-up errors which become apparent following birth. Likewise, it is crucial that at embryo transfer the patient receives the correct embryo. To this end there is a requirement for traceability throughout the process from the start to finish. Furthermore, there is also a need to ensure that procedures are done on time and correctly, therefore minimising the risk of issues in development of a fetus which may come as a result. In addition, as infrequent the cases of patients deliberately presenting themselves to treatment under disguise are, this possibility also has to be considered. Overall, a reliable identification, tracking and matching process that is proven and can be audited provides greater assurance both to patients as well as protection from litigation to an organisation and their staff.

Hence it is extremely important to develop fail-safe mechanisms for matching and traceability of gametes, embryos and patients throughout the treatment cycles. Many strategies can be adopted to achieve this, including improved quality control and quality assessment systems and procedures, professional certifications (including process audits), educational programs, individual training and external quality assessment. Nevertheless, none of these alone can absolutely prevent identification, traceability and matching errors. Therefore, implementations of specific policies such as double-checking have been introduced. Especially in light of some well publicised high-profile cases of IVF mix-ups, double-checking every step of the IVF clinical and laboratory procedure has become mandatory in many countries, or at least highly recommended.

Matching and traceability processes in an IVF laboratory may comprise:
- Matching correct sperm to correct patient providing it (patient specimen labelling) and, for donor sperm, matching any donor sperm to the couple who are now owners of the sperm.
- Tracing that sperm is correctly identified and labelled at every step when they are moved, for example from one tube to another (sperm reception and processing, including possible cryopreservation).
- Matching correct eggs to correct patient from whom they are extracted.
- Tracing that eggs are correctly identified and labelled at every step when they are moved, for example from one dish to another (egg collection, ICSI [intracytoplasmic sperm injection] and IVF).
- Matching correct patient eggs to the correct sperm, i.e. to the patient's partner or the intended sperm donor (insemination of patient with sperm, mixing of sperm and eggs in IVF, or injection of sperm to eggs in ICSI).
- Tracing that embryos are correctly identified and labelled at every step when they are moved, for example from one dish to another.
- Matching correct embryos to the correct patient at embryo transfer (fresh transfer or transfer of cryopreserved embryo).
- Tracing that embryos are correctly identified and labelled at every step during the cryopreservation process and afterwards, for example if moved from one cryostorage location to another.
- Tracing that embryos are correctly identified and labelled at every step when they are transported, for example from one clinic to another.
- Tracing that embryos are correctly identified and labelled at embryo discard or possible donation to another couple or to research, at every step, for example from cryostorage to disposal bin, from one cryostorage location to another or from one clinic to another.

Currently the most common method for matching and traceability is double checking ('double witnessing') by two operators. The premise behind it is to have two people carrying out the checking; first the actual operator performing the step, immediately double-checked by another operator who can witness directly that the matching is correct. Often this second witness is another embryologist, but it can also be a member of the nursing staff, doctor or another suitable trained person who is familiar with the process and matching requirements. Regulatory authorities in the ART industry have mandated manual double witnessing in recent times following a series of high profile incidents involving misidentification in order to reduce the risk of misidentification of patient samples. Manual double witnessing is generally accepted as the double checking that is performed on all clinical and laboratory procedures. Accordingly, there is an expectation that if an operator or user makes an error, it will be caught by the other 'witness'. Although mandatory double witnessing is a safeguard and there is apparent value, it has been suggested it may not be as effective as it should be.

There are also drawbacks to this type of double-witnessing, which include doubling of workload, distraction from other procedures being performed by the witness(es), double signage of paperwork and variability in reliability depending upon the technique employed. It also becomes problematic outside of normal working hours when a limited number of staff is present. In addition, the element of human error cannot be completely eradicated. The following factors may be known to facilitate human error:

1. Conscious automaticity (Familiarity with the procedure allows attention to be focused elsewhere).
2. Involuntary automaticity (Procedure becomes so predictable and/or tedious that attention to it is inadvertently reduced/lost).
3. Ambiguous accountability (Individual attention is rendered insufficient, usually when two people are responsible for a procedure).
4. Stress (Usually correlated with workload, distraction and fatigue).

Unique pressures that each IVF clinic faces are tremendous—staff having to ensure processes are being correctly followed, performed with the correct equipment, performed by people with correct skills, using the correct medication, in the correct environment and in a timely manner. The fact that this work involves each patient's potential future offspring puts an additional strain into the procedures, their value being quite unique and irreplaceable should something go wrong. This can be very stressful for the staff, increasing the chance of an error occurring. The patient load at the clinic can also fluctuate vastly leading to extremely busy periods with heavy clinical workload, this in turn may lead to fatigue and increased likelihood of human error.

As embryos do not have readily apparent and available individual characteristics that can be used to identify them, the applied methodologies and protocols have to ensure identification by other means, mostly via the correct use of labels on vessels where gametes and embryos are stored.

Further to the above, a number of guidelines state that each patient must be uniquely identifiable both in terms of where the gametes/embryos are at any one stage and in terms of the accompanying paperwork/database entries. Identification usually utilises three different identifiers, often the surname and the birth date of the patient, as well as a unique laboratory ID assigned to a specific treatment cycle via a relevant patient management system or a Patient Number ID, which is different to the cycle ID.

An example of a typical process of fertility treatment, focusing on identification and traceability stages is as follows:

1. Patients sign up at the clinic and their details are recorded into the system. Identity details are checked via official documentation and unique laboratory IDs are assigned.
2. Various other visits for blood samples and their analyses, handing over the correct drugs for hormonal stimulation, ultrasound examinations and treatment discussions follow the initial appointment, all requiring both patient identification and traceability of the process outcomes (for example tracing of blood samples and results, ultrasound images and their results). Many of these processes are managed outside a typical IVF clinic and there is a plethora of other guidelines and systems to ensure traceability of these processes.
3. Patient(s) enter the clinic for the sperm donation/egg collection, and their identities are checked both verbally and visually, often in front of witnesses. Identity bracelets are often assigned to the patients.
4. All plastic ware including sample containers, tubes, dishes etc. to be used in the processes are marked with a minimum of, or at least two identifiers (i.e the unique ID). This marking must be indelible and be affixed to as many pieces of plastic ware as required to ensure affiliation with the biological materials (for example both bottom and lid of a culture dish).
5. Likewise all paperwork and/or database entries are created linking the process with the unique IDs.
6. In many clinics the location where the gametes or embryos are stored may also be recorded, be it short term (location in a specific incubator) or long term (cryostorage in a $LN_2$ tank). Currently the location of storage of samples is paper-based and subsequently entered in EMR with respect to the recording stage.
7. During the process the unique IDs are checked against the paperwork or stored data, the plastic ware and the progress of biological samples and signed off by the scientist at every step of the process (which may be up to 10 to 40 steps during an IVF cycle).
8. In addition, most clinics have strict protocols in place that forbid handling of more than one cohort of eggs, sperm or embryos at any one given time in any given space.
9. Disposable consumables coming into contact with biological materials are always used strictly on a single-use basis and disposed of immediately, thus not necessarily requiring labelling or further identification or traceability checks.
10. At the time of embryo transfer, a patient ID is crosschecked against both the paperwork/database and the vessel containing the embryo(s) before the embryos are transferred.

Many of these checks may include physical linking of the proof of identity to the records, for example removing the label of a container and affixing it to paperwork.

In addition to strictly laboratory based procedures there are several other steps during a typical treatment cycle that require patient ID checks and witnessing, including for example checks that appropriate clinical consents have been signed, collection of correct contact and billing details and so forth.

Patient files—both physical paper-based as well as database entries—have to be maintained for a minimum number of years, often defined by national legislation and guidelines.

All these protocols ensure that there is a paper/database trail that can be followed and assessed at any time. Internal and external audits of IVF clinics are routinely conducted as per national guidelines to make sure checks are being done properly and conform to international standards. The number of crosschecks may seem initially excessive, but this is a result of a deliberately built-in redundancy to make the system as 'fail-safe' as possible. That is, if one or more check is missed or wrongly conducted, the next check should capture and correct the situation.

Besides double-witnessing by humans, electronic witnessing systems have been developed over the last several years to address the witnessing and traceability requirements and improve accuracy and convenience of use. Barcode scanning was one of the first such applications, being very familiar and widely used already, having been used in the retail industry for more than 20 years and benefiting from an error rate of just 1 in more than 15,000. Examples of such systems are provided with the RI Witness® ART management system by Research Instruments Limited using RFID (Radio Frequency Identification) technology to track and record patient samples at each step of the ART process and, the Matcher® witnessing system by IMT International using barcode technology. It is considered that the RI Witness® system may not adequately address the issue of tracking consumable batches in the ART laboratory environment and requires removal of samples from $LN_2$ to achieve effective management and tracking at cryo stages. The RI Witness® system requires expensive capital equipment as each individual workstation will require a dedicated RFID reader. Another issue with this RFID arrangement is that it does not function reliably under a liquid nitrogen environment. The Matcher® system is a barcode matching system which lacks workflow management and does not have $LN_2$ tracking. Further, the Matcher® system is considered to lack an overall lab workflow indication or display and like the RI Witness® system requires removal of samples from $LN_2$ to achieve effective management and tracking at cryo stages.

By way of illustration, FIGS. 3 to 10 show a summary of some of the most common processes in an IVF lab workflow where each of the boxes with solid rectangular outline demonstrates a double witnessing step. FIG. 3 illustrates a general IVF workflow with at least 13 double witnessing steps. FIG. 4 shows an ICSI/IMSI/PICSI/TESE workflow with at least 15 double witnessing steps. FIG. 5 shows a sperm collection workflow with at least 14 double witnessing steps. FIG. 6 show a PGD workflow with at least 7 double witnessing steps. FIG. 7 shows a transfer workflow for Days 2, 3 and 5 with at least 7 double witnessing steps. FIG. 8 shows an embryo hatching workflow with at least 4 double witnessing steps. FIG. 9 shows a thaw workflow with at least 5 double witnessing steps. FIG. 10 shows a freeze/vitrification workflow with at least 5 double witnessing steps.

The discussion throughout this specification comes about due to the realisation of the inventor and/or the identification of certain related art problems by the inventor and, moreover, any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

Throughout this specification the use of the word "inventor" in singular form may be taken as reference to one (singular) inventor or more than one (plural) inventor of the present invention.

SUMMARY OF INVENTION

An object of the present invention is to eliminate the use of human-implemented double-checking protocols during ART procedures.

Another object of the present invention is to perform patient and biological sample identification and tracking during ART procedures to eliminate mismatching events and their potentially catastrophic consequences.

A further object of the present invention is to overcome or alleviate at least one of the above noted drawbacks of related art systems or to at least provide a useful alternative to related art systems.

Embodiments of this invention provide personalised intelligent ART assistance for clinical work flow management and error prevention, ensuring processes have a valid order at appropriate times, using appropriate materials and equipment by an appropriately trained staff. It can assist in tracking identity of materials, equipment, environmental conditions and staff, linking this information to a patient's clinical journey and clinics supply chain management.

Accordingly, in one aspect, embodiments of the present invention provide a device for monitoring the accuracy of procedures in the course of the performance of a task, the task comprising at least one procedure to be performed, the device comprising:
an input interface for receiving input data relating to the procedures;
a data store for storing data relating to the procedures;
a processor for:
comparing the input data with the stored data; and
generating a comparison result indicating the result of that comparison; and
an output interface for outputting the comparison result.

In another aspect, embodiments of the present invention provide a system for monitoring the accuracy of procedures conducted on a biological sample in the course of the performance of a task, in which:
the procedures comprising the task are each to be performed within a specific period on a time-line; and
an output device displays:
the procedures which are to be performed in each specific period of time on the time-line; and
the result of a comparison between input data relating to the procedures.

A method of monitoring the accuracy of procedures in the course of the performance of a task is provided in preferred embodiment in which, the method comprises:
inputting data relating to the procedures into a data store;
storing data relating to the procedures;
generating a comparison result indicating the result of that comparison; and
outputting the comparison result with an output device.

The procedures comprising the task may each be performed within a specific period on a time-line. Preferably, each specific time period is a day.

In other preferred embodiments a hand-held device and software is provided to identify and track human samples through the assisted reproduction cycle.

In preferred forms the invention further provides a method of indexing the location of a biological sample in a laboratory environment, the method comprising the steps of:
locating an RF transceiving device proximate a biological sample container wherein the RF transceiving device is of a construction and/or fabrication that is resistant to a range of laboratory conditions including one or more of a cryo-environment and gamma irradiation;
interrogating the RF transceiving device for identification signals unique to the biological sample.

The method may further comprising steps of:
locating further RF transceiving devices corresponding to each of a hierarchy of laboratory apparatus for addressing the location of the biological sample within a laboratory environment.

In the method above one or a combination of the step of interrogating and the RF transceiving device may comprise at least one MEMS device.

In the method above the RF transceiving device may be adapted to transmit in situ environmental conditions of the biological sample in addition to identification signals unique to the biological sample.

Furthermore embodiments comprise apparatus for indexing the location of a biological sample in a laboratory environment, comprising:

an RF transceiving device adapted for location proximate a biological sample container wherein the RF transceiving device is of a construction and/or fabrication that is resistant to a range of laboratory conditions including one or more of a cryo-environment and gamma irradiation; and interrogation means for interrogating the RF transceiving device for identification signals unique to the biological sample.

In the above apparatus one or a combination of the RF transceiving device and the interrogation means comprises a MEMS construction.

Other aspects of the present invention are set out in the claims which appear at the end of this specification.

In essence the present invention stems from the realisation that one or a combination of the identification, tracking, reporting and overall management of biological samples and associated objects in the ART laboratory environment is substantially improved where process flow rules and activities associated with the ART treatment procedures and apparatus are based on or correlated to the biological sample's development timeline, e.g. the days of the human embryo development timeline. Furthermore, the present invention stems from the realisation that a single centralised database of actual locations of all samples in the care of a laboratory may be achieved with avoidance of removal of a sample from a cryo processing environment by the use of an RF device embedded in polymer encasing resistant to a cryo environment and proximate individual samples for transmitting identification signals for use in addressing the location of individual samples.

Advantages of the present invention comprise the following:

Logging and validation of every step is possible with preferred embodiments of the invention given that there may be a specific electronic record of the location of each sample, which is used in both the logging in and the logging out of samples;
Electronic witnessing is achieved;
Process mapping and workflow management is configurable;
Overall laboratory workflow is displayed for users;
Tracking of consumable batches;
Labelling is able to be applied across the board;
Low cost equipment and per patient cost;
Reporting and auditing of ART laboratory is available;
Connectivity to electronic medical records (EMR);
Witnessing available in the cryo environment;
Management and tracking of biological samples in the cryo environment and furthermore, management and tracking of biological samples is provided in the cryo environment without sample removal being required;
Witnessing and monitoring the temperature at the sample level under liquid nitrogen.
A simple hand-held device used to scan dishes, tubes and other consumables used to maintain and process patient material such as oocytes and sperm to check that there is a correct match;
Sample identification and tracking during ART procedures to eliminate mismatching from occurring
Provide a personalised intelligent ART assistance for clinical workflow management;
Provide identification tracking in $LN_2$;
Assists clinics to comply with witnessing requirements from governing authorities;
Minimise error by confirming barcode matching;
Eliminate the requirement of manual double witnessing;
Low cost and integrate-able to current lab systems;
Quick and easy to implement;
Configurable workflow management to ensure the next processes are followed.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present invention may be better understood by those skilled in the relevant art by reference to the following description of embodiments taken in conjunction with the accompanying drawings, which are given by way of illustration only, and thus are not limitative of the disclosure herein. In the drawings:

FIGS. 15 to 18 show, from the aspect of a user interface, the activities and rules that can be established along with user messages in accordance with preferred embodiments;

FIG. 21 shows an exemplary display suitable for a hand held device or web interface showing the feature(s) of tracking, reporting, inventory management and stock take for consumables of an ART laboratory;

DETAILED DESCRIPTION

System Description

In accordance with preferred embodiments, the present invention provides an ART laboratory management system that addresses the following tabled laboratory functions with the associated features listed against each function as follows:

| Laboratory Function(s) | Feature |
| --- | --- |
| Witnessing | Define Labels |
|  | Cycle Prep/Patient Selection |
|  | Matching/Witnessing |
|  | Manual Witnessing |
| Administration/ | Logs And Reporting |
| Management | User Management |
| Error Prevention | Define Lab Processes |
| Workflow | Define Activities |
| Management | Workflow Tracking |
| EMR connectivity | EMR connectivity |
| Workflow | Cycle Progress Management - Lab Dashboard |
| Management | Cycle Progress Management - Handheld |
|  | Cycle Progress Management - Desktop |
| Consumable | Consumable Lot Tracking |
| Tracking & Checking |  |
| $LN_2$ management | Customise mobile device |
|  | $LN_2$ tracking ID tracking |
|  | Cryo-management location identification of patient |

Figure 11:
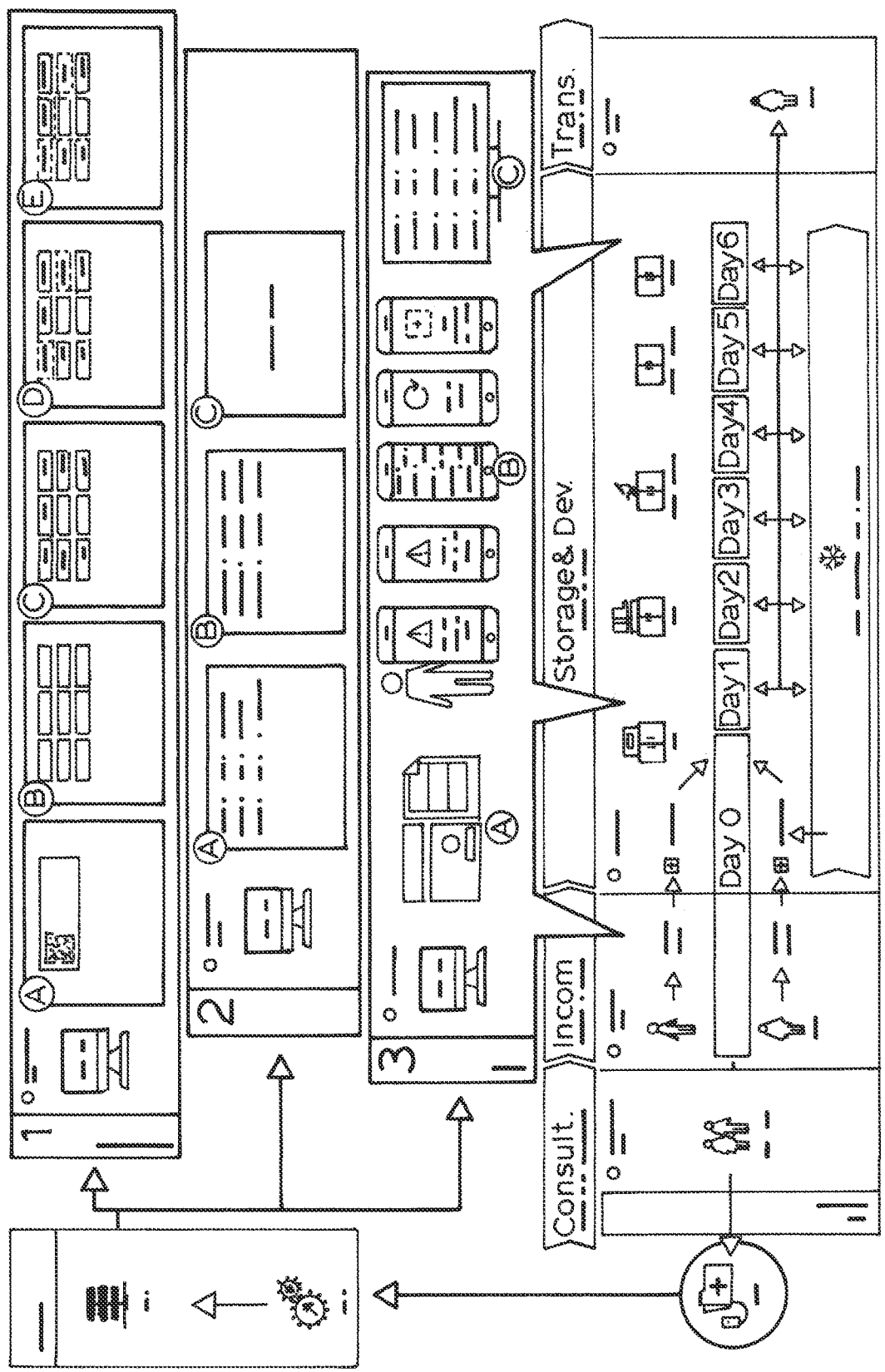
FIG. 11 is a schematic diagram showing an overview of ART treatment utilising the management of procedures in accordance with a preferred embodiment of the present invention.

FIG. 11 provides a conceptual schematic providing an overview of ART treatment utilising the management of procedures in accordance with a preferred embodiment of the present invention. In the context of an ART treatment involving patients in the stages of consultation over a period of weeks; pick up occurring within a day, storage and development of embryos for up to 7 days and then transfer of viable embryos within a day, workflows 1 (configuration), 2 (supervising) and 3 (Using) are illustrated in FIG. 11. Workflow 1 of FIG. 11 involves a configuration protocol in the laboratory/office involving creating and editing labels for patient biological samples, creating label groups corresponding to cycles, assigning labels to the development timeline of days in the cycle, specifying critical labels and specifying critical activities to be undertaken. Workflow 2 of FIG. 11 involves a supervising protocol in the laboratory/office involving management of an active patient list, management of consumables and generating reports including information for histories, inventories for lot numbers of consumables etc. where this reporting can facilitate audits.

Workflow 3 of FIG. 11 involves a user application protocol of embodiments of the invention within the laboratory and practice rooms of the clinic, which finds particular application to the stages of pick up after consultation and storage and development precedent to transfer of viable embryos.

In facilitating witnessing and a patient ID check a preferred protocol of embodiments provides for a check that multiple labels scanned as a group have matching patient ID's, prior to transferring samples between containers in a laboratory. Implementing this function needs minimal knowledge beyond the patient ID number encoded in the barcode itself.

In facilitating error prevention a preferred protocol of embodiments defines high level process flows based on days, and grouping of containers under each day. Then it is preferred to check which days the scanned containers are under and warn the user if they are incompatible. In accordance with preferred embodiments central server connectivity with a user accessible interface via web and/or hand held device provide access to:

Manage users
Access and export logs and reports for quality checks and audits
Generate and print labels & QR codes
.csv import of patient details
Generate billing reports
Create, import or export system configurations A consumables check is provided by a protocol in which a consumable is scanned prior to use. Lot numbers are recorded and the expiry date is checked. The compatibility may also be checked e.g. compatibility of the media with the container type.

Witnessing within cryo storage vessels may be provided by a scanning of barcodes on Cryo storage vessels such as Pods or Cryotops to provide electronic witnessing.

Workflow management of daily laboratory process flows is provided by defining high level process flows and keeping track of and displaying the work required for each day.

An EMR interface can be provided by an API with documentation enabling EMR access to embodiments of the invention to enable patient details entry, storage location update and process mapping.

An error prevention protocol for checking process steps is created by defining only the steps in the lab that are deemed to be most critical, either because the consequence of a mistake is severe and/or errors are more common at that step. The lab manager would identify these critical steps and define details such as container types, quantity and sequence.

An error prevention protocol for consumables in laboratory steps is created by checking that the number of dishes (of the same type) required for a particular step are all present. This may be dependent on the number of embryos and/or the type of transfer that is about to take place.

Embodiments of the invention may be utilised to index the location of a sample as it is placed in a $LN_2$ storage system (i.e. tank, level, canister, cassette/cane), and to help find the sample when removing it from the $LN_2$ storage system.

Embodiments of the invention may be utilised to eliminate the need for double-witnessing during $LN_2$ steps, including both sample identification prior to exposing samples to room temperature and sample identification prior to transferring a sample to the next container type.

Figure 1:
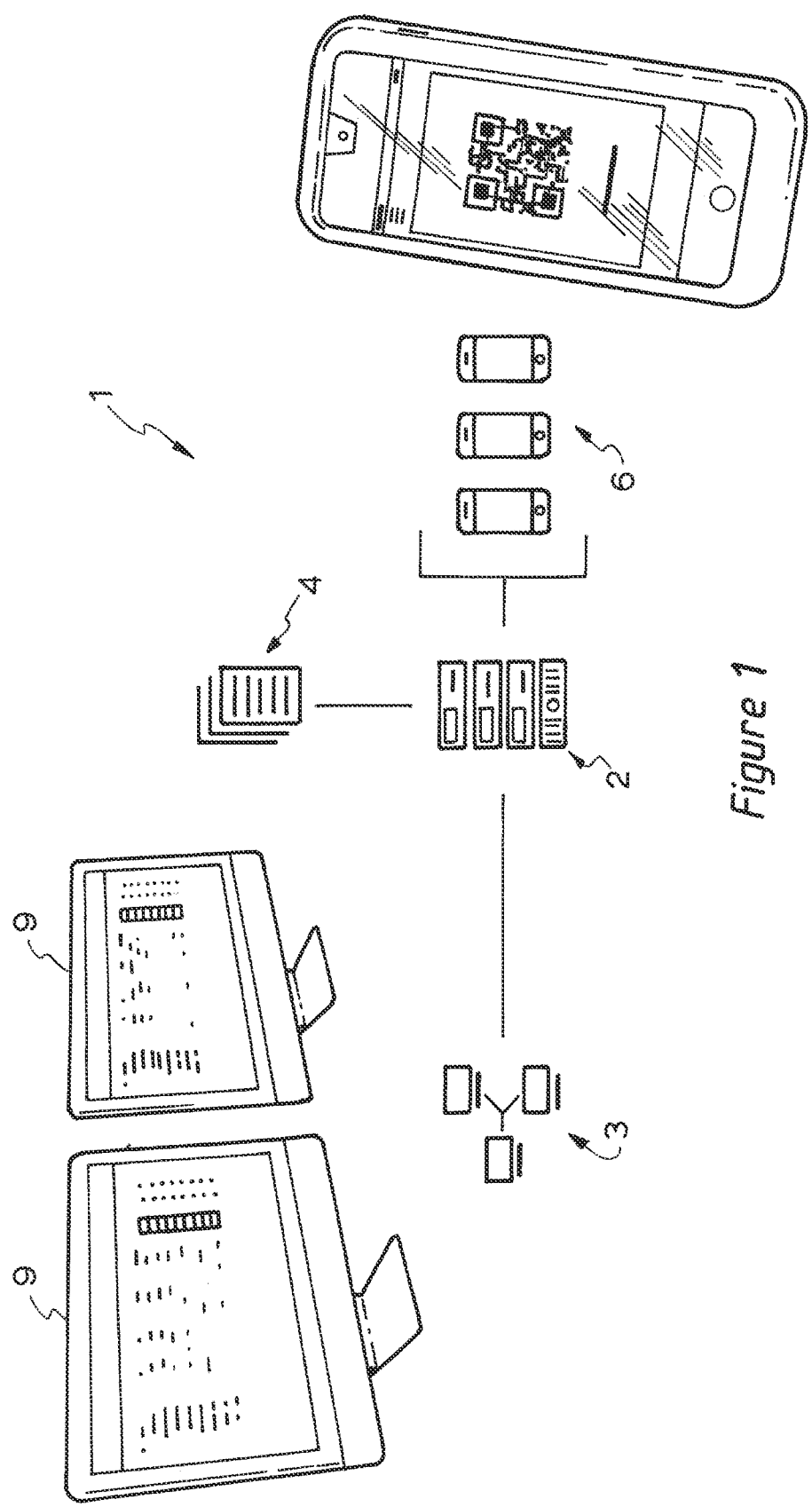
FIG. 1 is a block schematic drawing which illustrates a system for patient and biological sample identification and tracking during ART procedures according to preferred embodiments of a system according to the invention.
Figure 2:
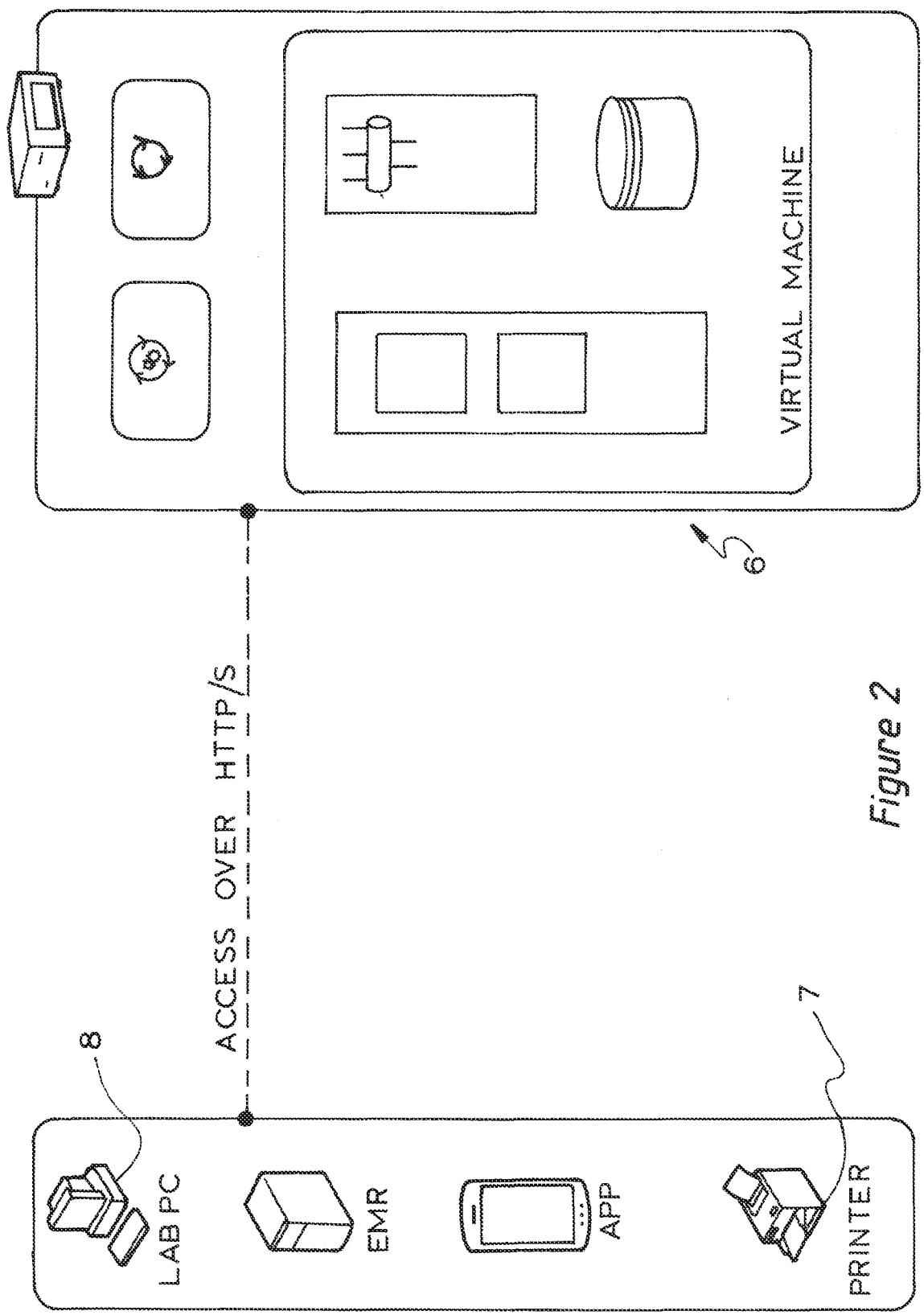
FIG. 2 is a message transfer level diagram illustrating deployment of a preferred embodiment of the present invention.
Figure 3:
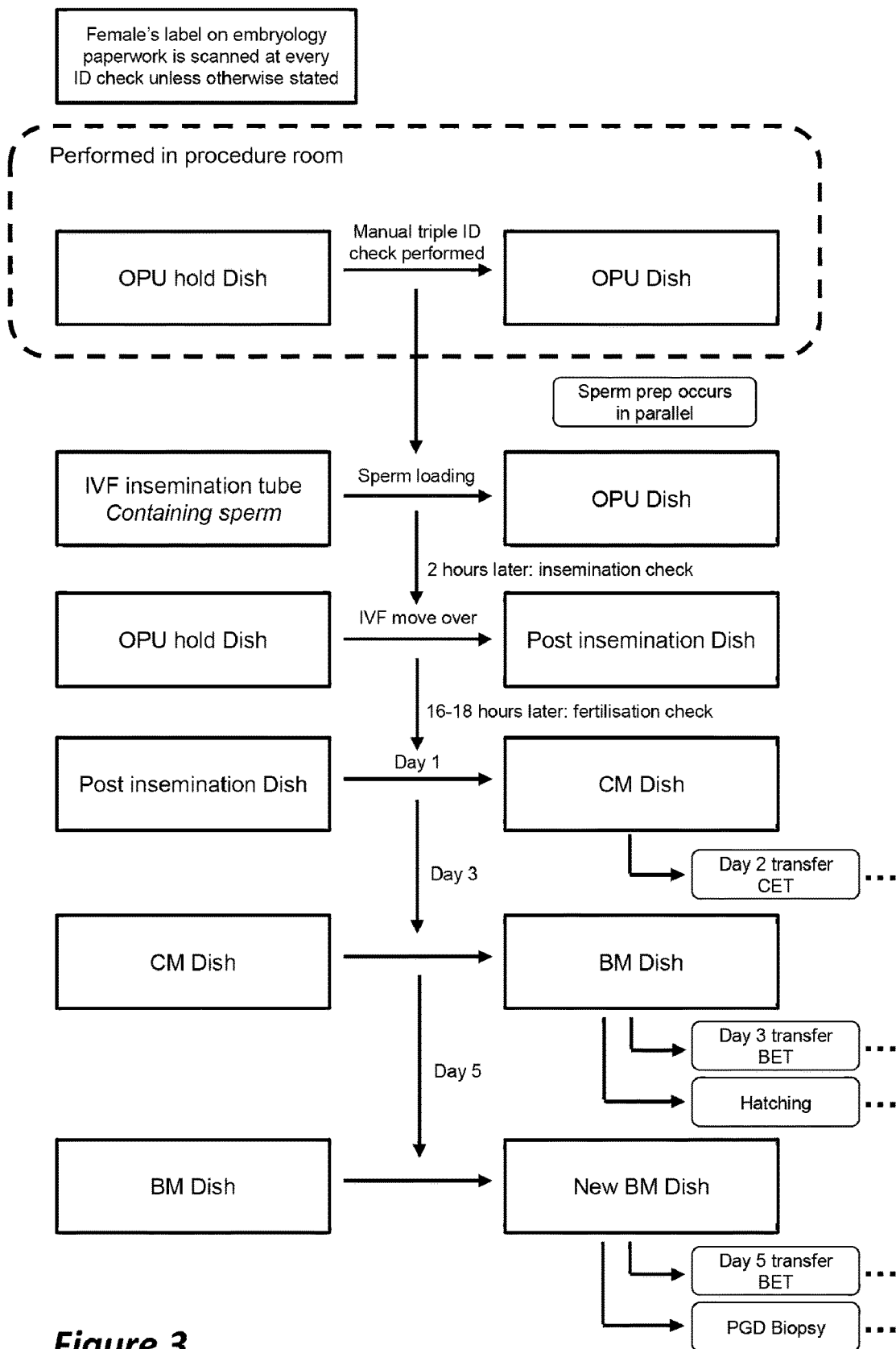
FIGS. 3 to 10 provide a summary of common process steps in an IVF laboratory workflow illustrating steps that require double witnessing.
Figure 4:
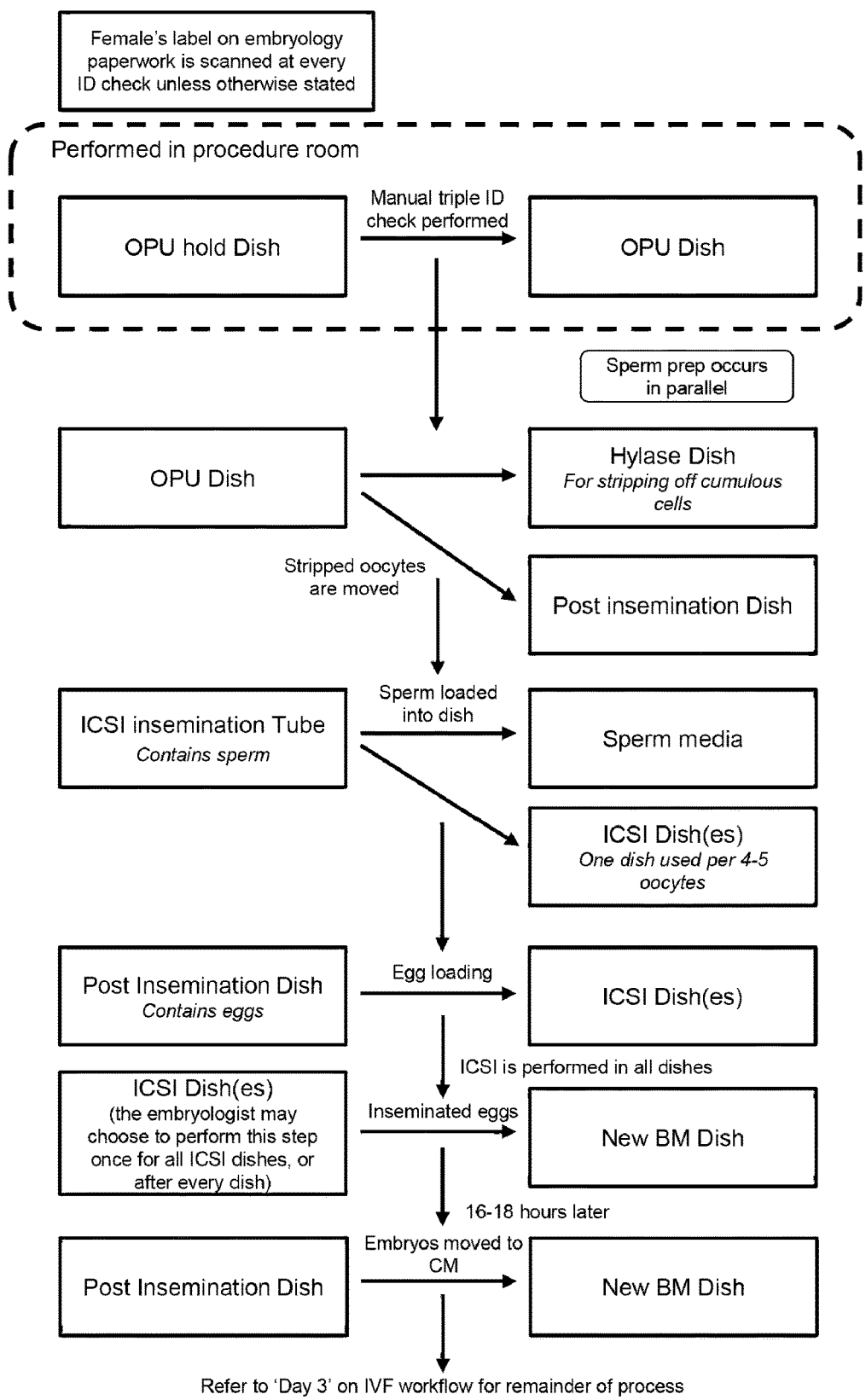
Figure 5:
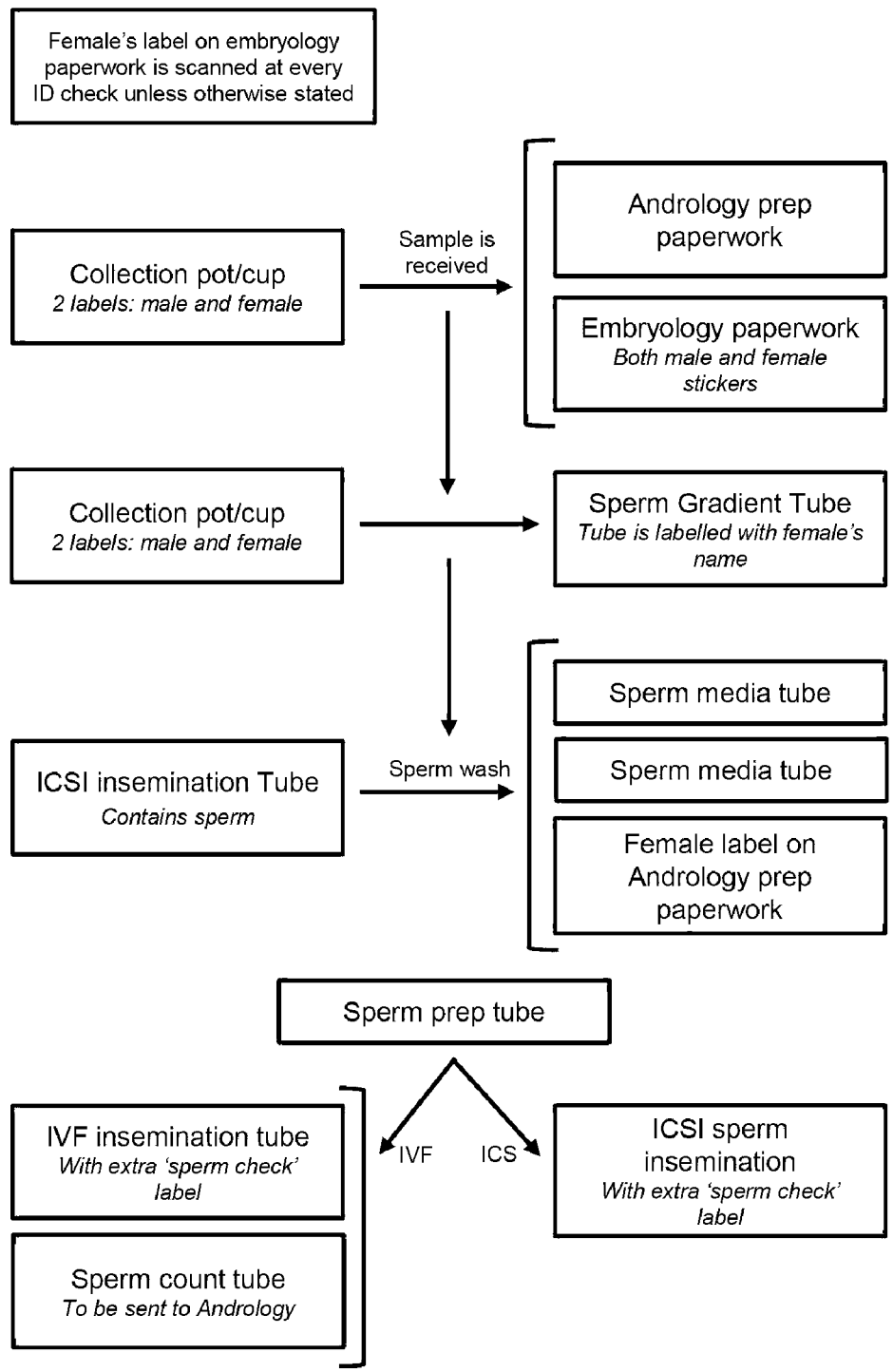
Figure 6:
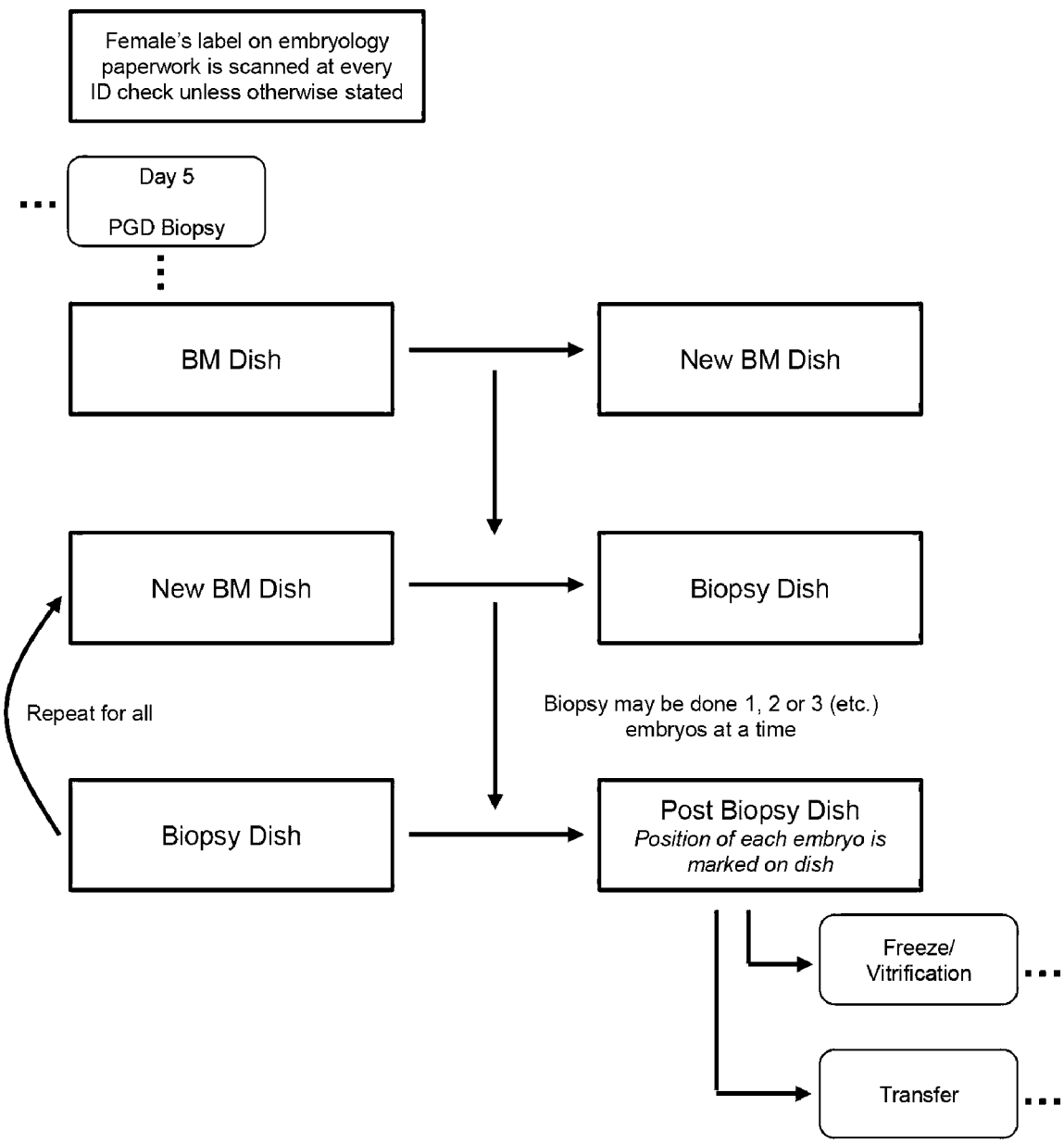
Figure 7:
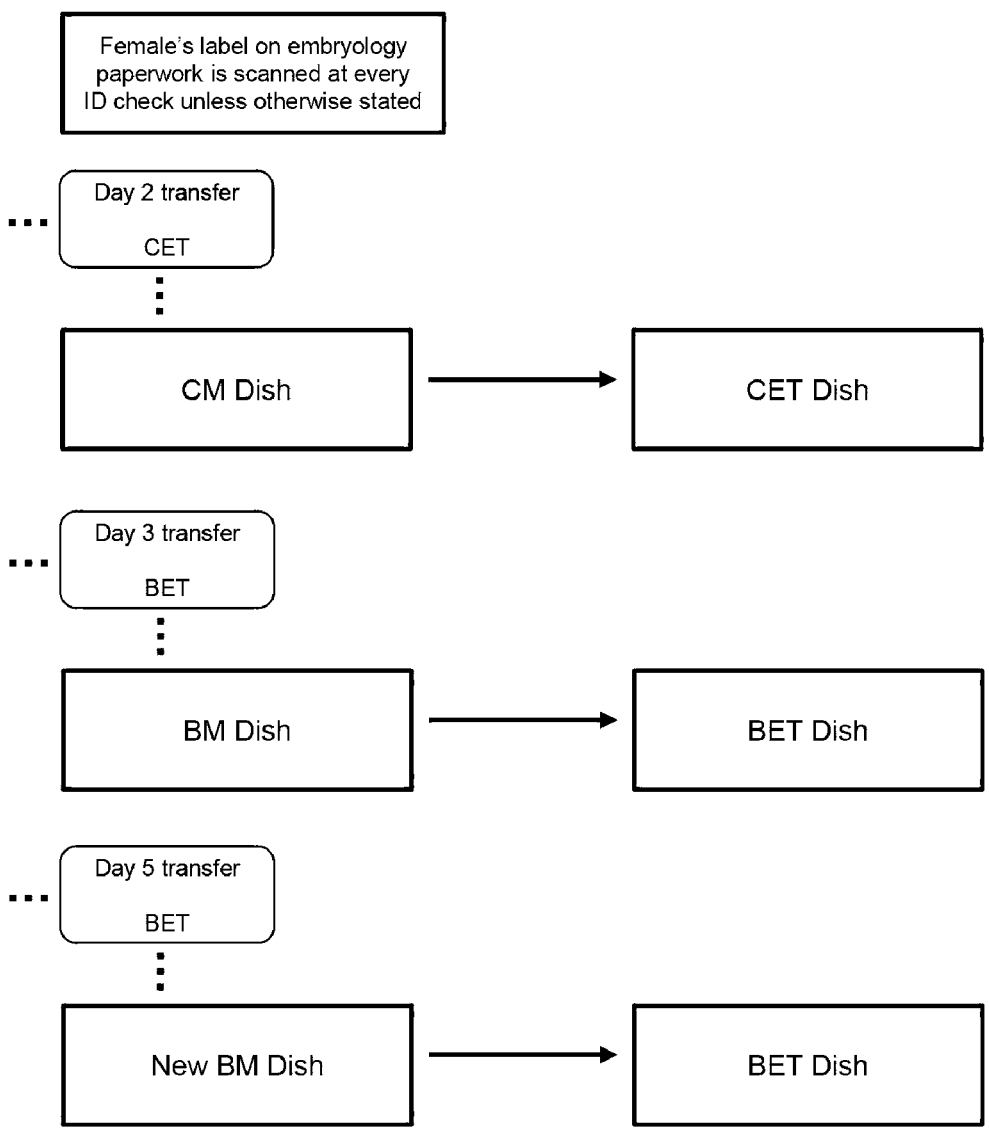
Figure 8:
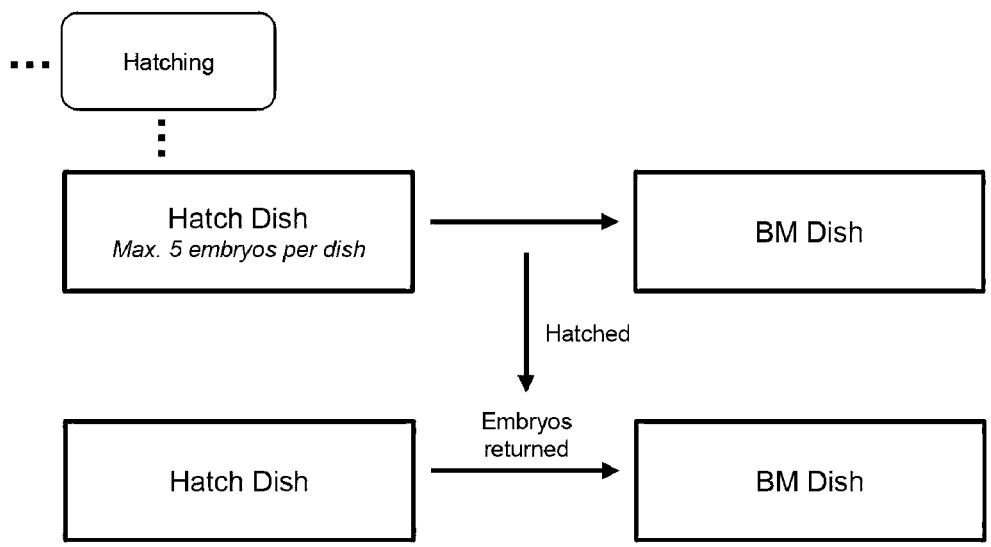
Figure 9:
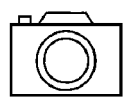
Figure 9:
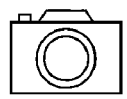
Figure 10:
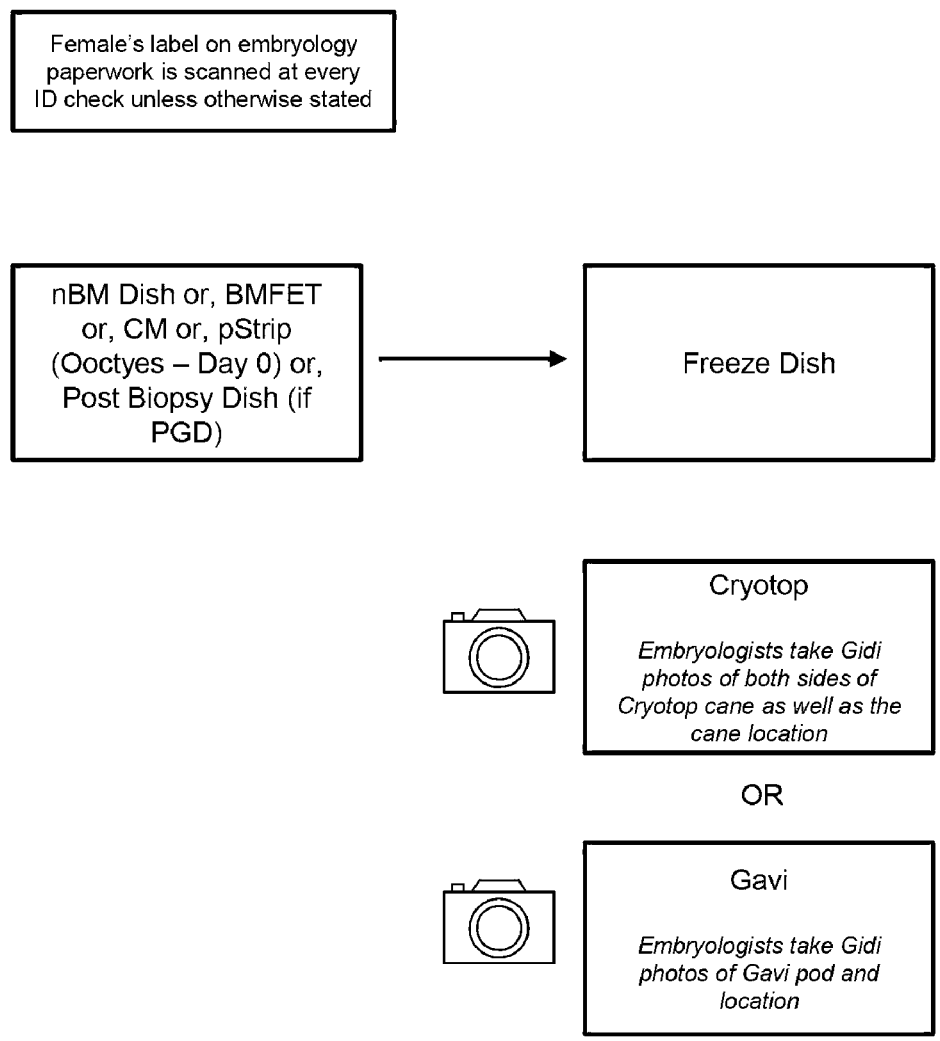

By way of practical implementation of the above, as is illustrated in FIG. 1, a system 1 according to preferred embodiments of the present invention includes a central computer means 2 comprising for example a database server. The central computer 2 is connected to a local area network LAN 3 for example by way of an Ethernet network and also an information storage 4 of medical and/or laboratory information such as a laboratory information system (LIS) and electronic medical records (EMR). In a practical implementation, the LAN network 3 includes a switch and a WiFi access point as would be appreciated by the person skilled in the art. The central computer 2 and LAN 3 is wired or otherwise connected to input and output devices 6 and may in preferred embodiments also be connected to a label and report printer (shown in FIG. 2), desktop computers 8 (shown in FIG. 2) with displays 9 and laptop computers (not shown) for use by laboratory staff. Portable devices which wirelessly connect with the WiFi access point include handheld devices such as the readers 6 shown in FIG. 1. These may take a smartphone form factor and tablet devices. The LAN network 3 also connects to an external network (which is not illustrated in the drawing) through a firewall which may have a VPN (virtual private network) functionality. According to alternative preferred embodiments of the invention which are not illustrated in the drawings, alternative forms of the devices may include operator-wearable, sensor equipped, devices such as camera-equipped and scanner-equipped glasses, bracelets, head-band, or like devices which have a capability of capturing data.

Each reader device 6 has at least "Unique ID" reading capability for reading any one of, or a combination of, 10 barcodes, 2D barcodes and RFID tags, using any one of, or a combination of, an infra-red scanner, a laser scanner, a camera with Optical Character Recognition (OCR), and an RFID reading. Each device 6 accordingly also comprises the relevant one or more of a scanner or scanners for the above technology, a camera for capturing images, a card reader (e.g. NFC smartcard or magnetic stripe card), a fingerprint scanner and an electronic signature capture pad.

Preferably each device 6 has additional functionality which comprises any one of, or a combination of:

Bluetooth, WiFi (or other) connectivity for linking to:
    sensors for embryo critical items (such as environmental monitoring, for example, temperature; humidity, volatile organic compounds (VOCs) and $CO_2$); and
    Bluetooth LE (low energy) beacons; and
other position location capability, such as by a global positioning capability (GPS, Glonass, Galileo) or local positioning system (LPS).

Preferred forms for the sensors include the "Bluechiip™" MEMS (micro-electromechanical systems) sensors of Bluechiip Ltd. Such MEMS sensors preferably include temperature sensing functionality and are preferably embedded in disposables such as:

vitrification/cryopreservation storage vessels/devices containing, for example, either sperm, embryos, oocytes or gametes during the process of vitrification/cryopreservation and subsequent storage;
cassettes and other holders for the vitrification/cryopreservation devices; and Canes, Canisters and Dewar LN2 tanks or vessels
Liquid nitrogen tanks
culture dishes for oocytes, embryos and gametes.

Advantageously, each Bluechiip™ smart chip contains Lorentz force resonators tuned to frequencies between about 1.3 MHz and about 4.1 MHz. The device may be passive, in that it does not require power but when the resonators are stimulated they return a signal that indicates the unique identification and temperature of each smart chip. The unique identification number is programmed during the manufacturing process and the tag is checked by an internal BCH error detection and correction code. Every time a smart chip is read, the instantaneous temperature is measured, time stamped and recorded. This allows a temperature history to be recorded to provide a more complete chain of custody. The smart chip will survive sterilisation by autoclaving or gamma irradiation with no degradation or loss of function.

Preferred forms of the reading/scanning devices 6 include smartphone and tablet devices running Apple iOS, MS Windows and Android or the equivalent mobile device operating system. They preferably use touch-technology, having touch-screen user interface and navigation. The database server of the central computer receives input from connected devices such the hand-held devices, and produces output which is sent back to connected devices, for example, computers 8, to the reading/scanning devices 6, and/or to a label and report printer 7.

As is described below, the database server of the central computer 2 receives input from the reading devices 6 during the course of the ART procedures, processes that input in accordance with algorithms within the database server, and sends output which has been produced by that processing to the reading devices 6. The database server of the central computer 2 may, on receipt of input from the devices 6, also send output to the label and report printer 7. Equally, the central computer 2 may receive input from connected PC's 8 and/or laptop/tablet devices in the same manner for processing and returning processed information.

Preferred forms of the database connected to the database server include off-the-shelf patient management databases which have been modified to implement the functionality required by embodiments of the present invention and custom-built databases which have been specifically written to implement that functionality.

A label and report printer 7 may produce labels which are to be attached to plastic-ware such as sample containers, tubes, dishes and the like, to patients' paperwork, and to patients' wrist-bands and the like.

The management system of preferred embodiments may be tailored to an individual laboratory in essentially four steps:
1. Define labels by specifying the type, size and content of the labels needed for all cycles run by a given clinic;
2. Define print groups by creating groups of labels that will be printed for all cycles and activities run by the clinic;
3. Define cycle rules by specifying which labels must be scanned for every witness session or for a particular day of a cycle;
4. Define activity rules by specifying which labels must be scanned for an activity.

Figure 12:
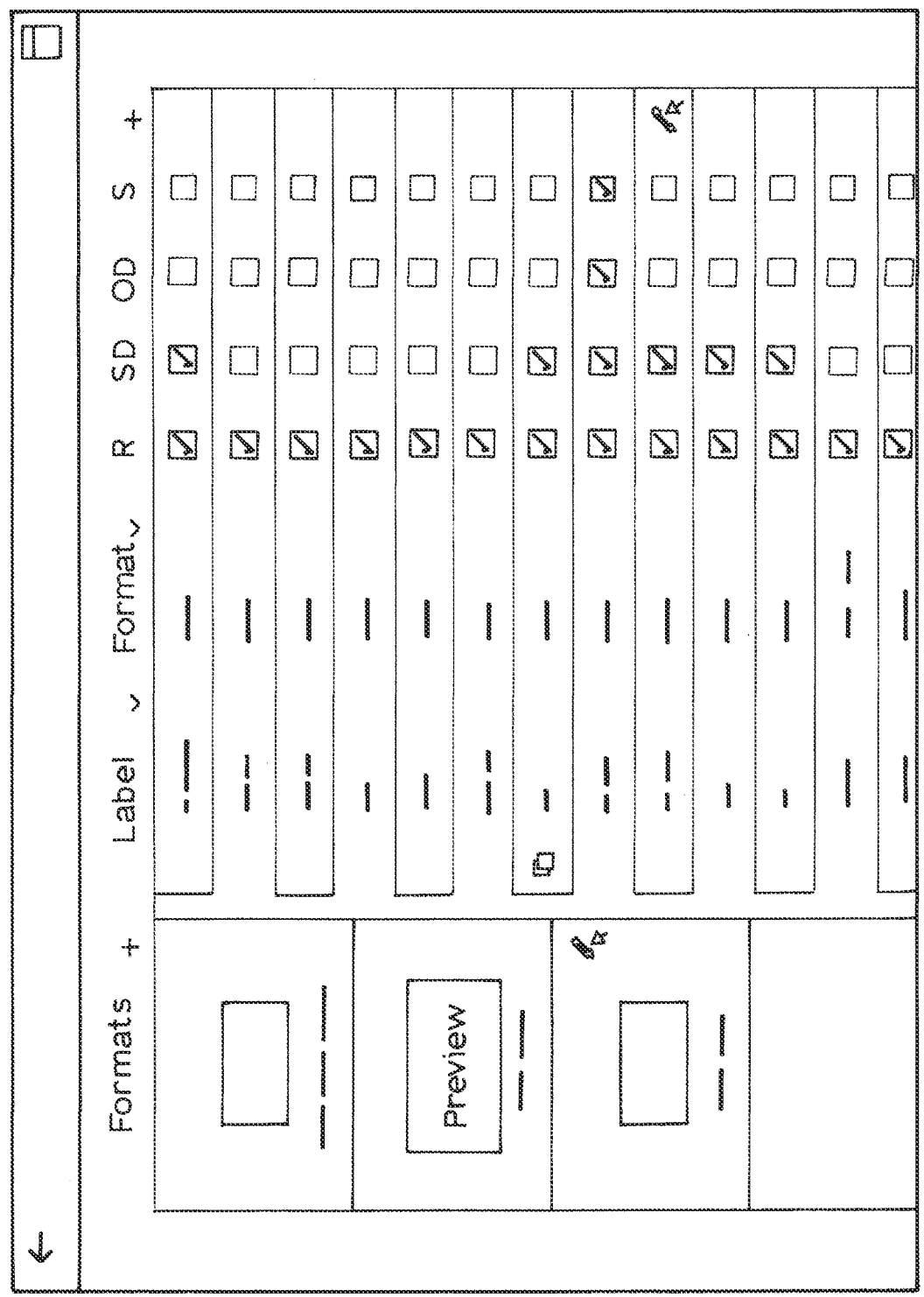
FIGS. 12 to 14 show, from the aspect of a user interface, the steps involved in creating, defining and assigning labels and print groups in accordance with a preferred embodiment.
Figure 13:
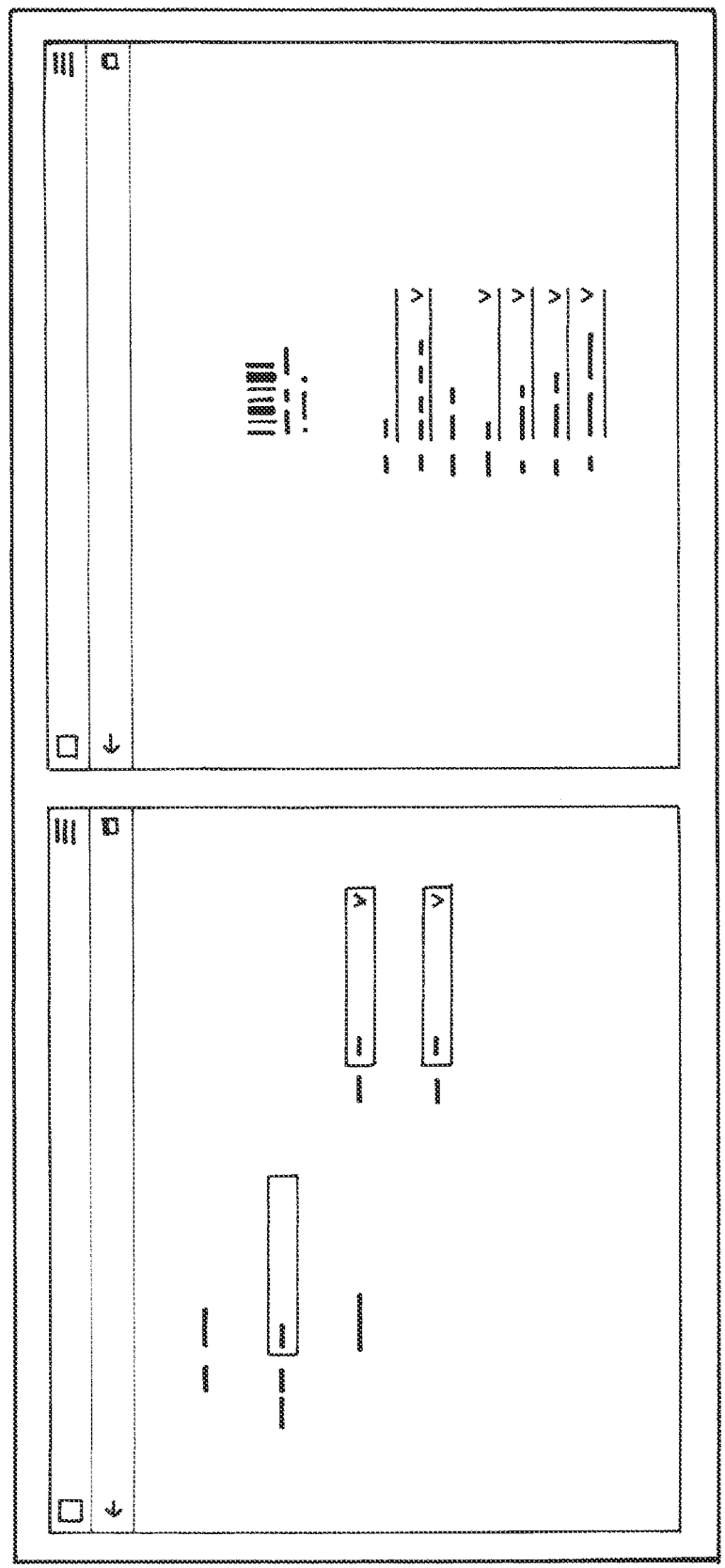
Figure 14:
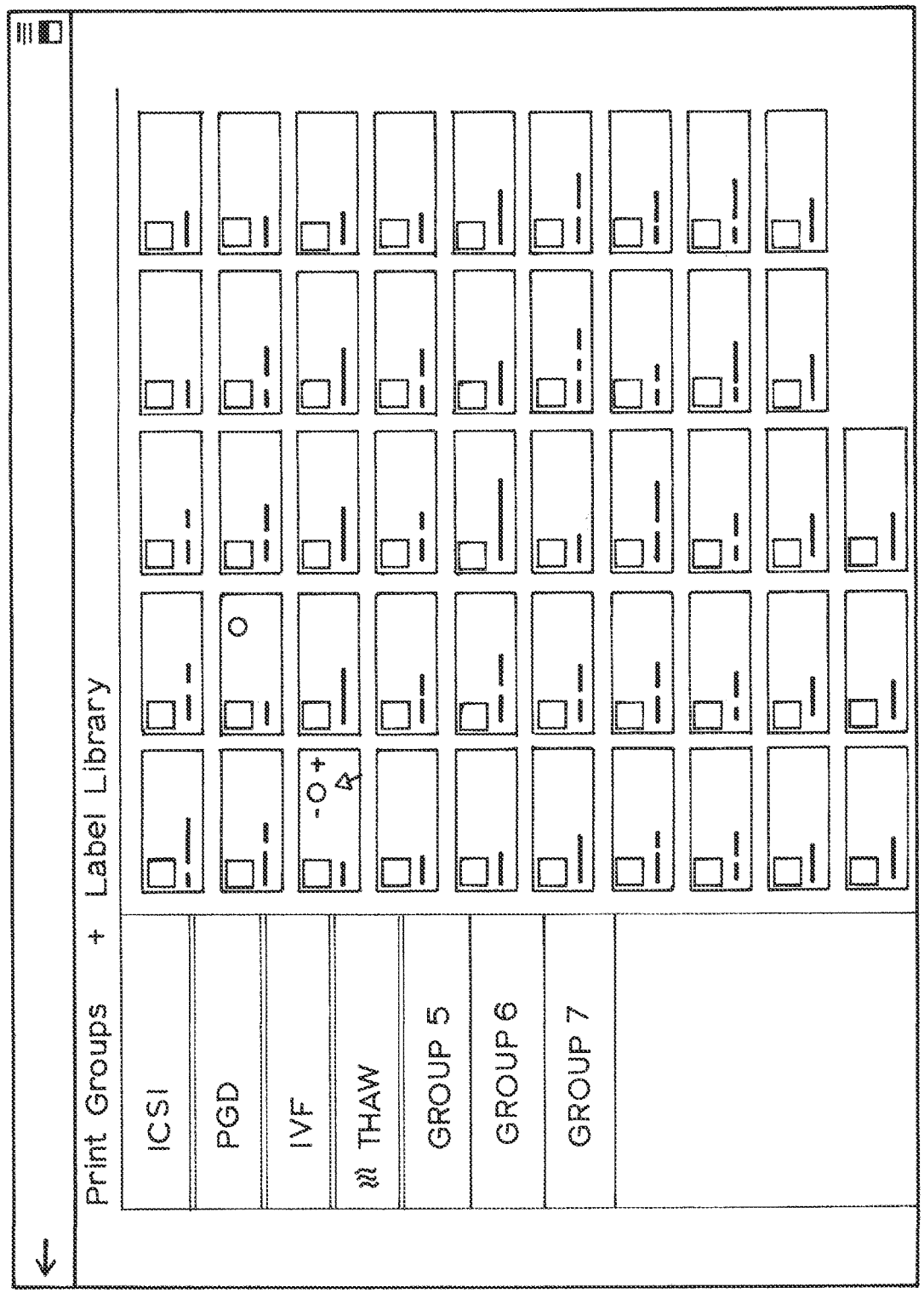
Figure 15:
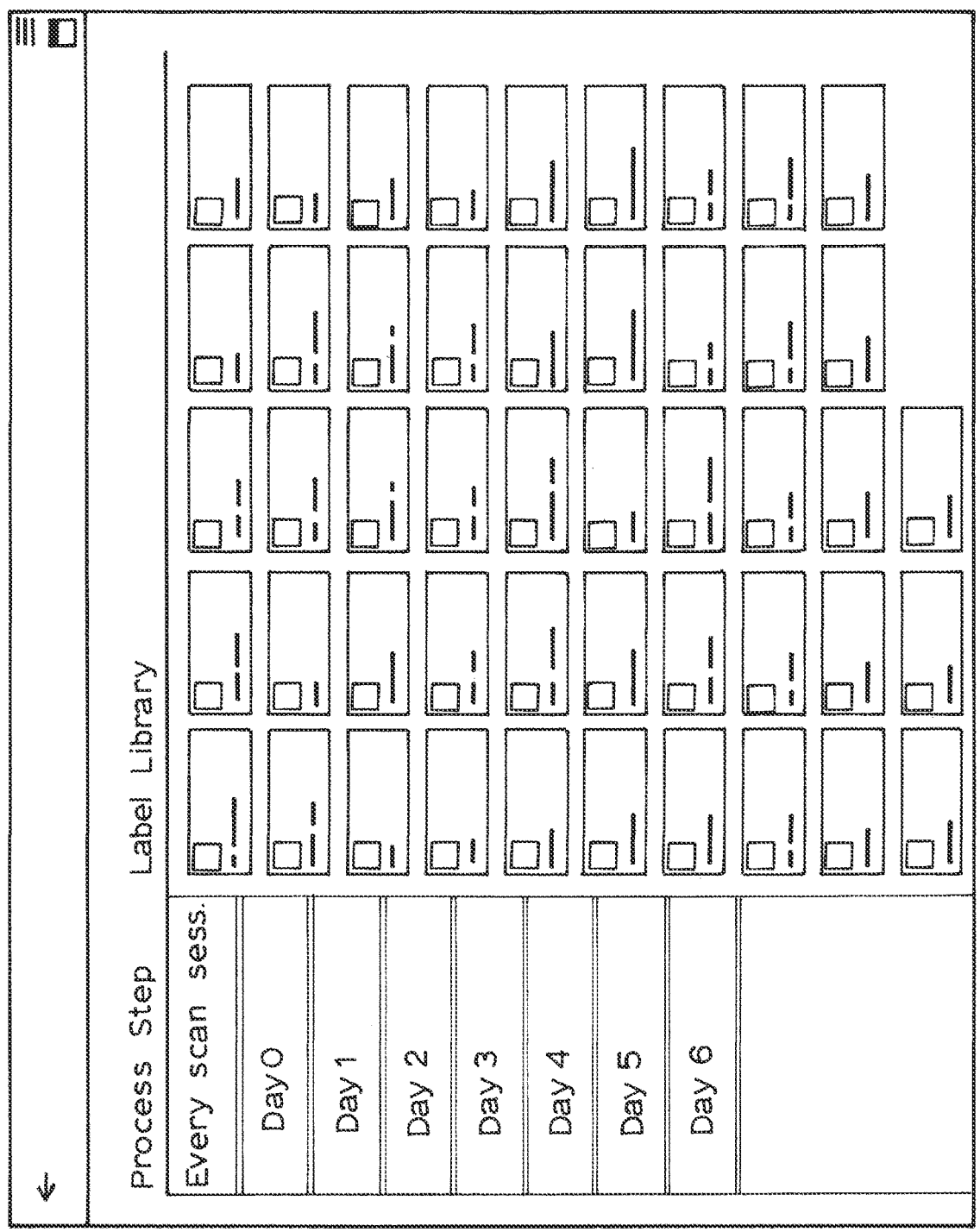
Figure 16:
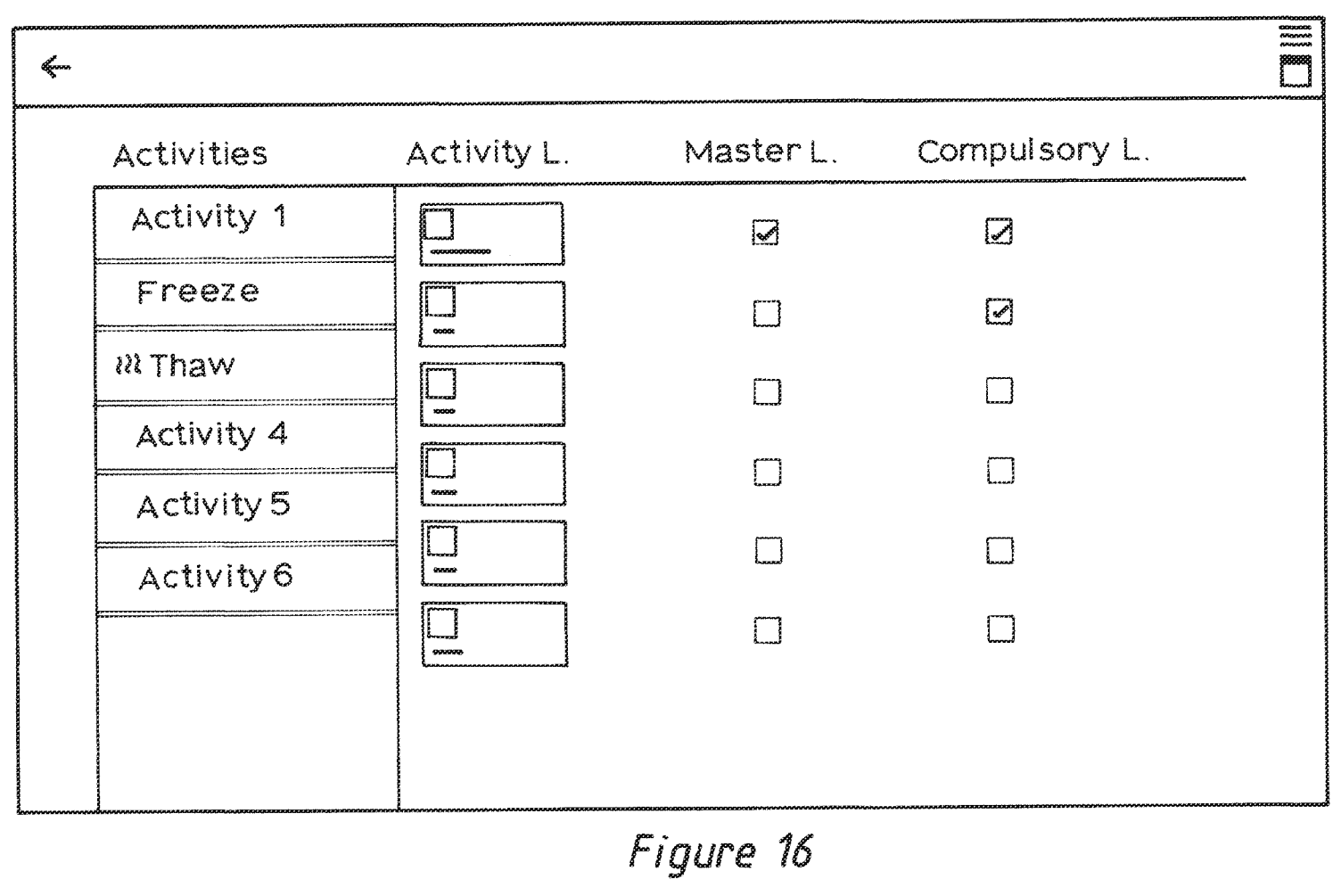
Figure 17:
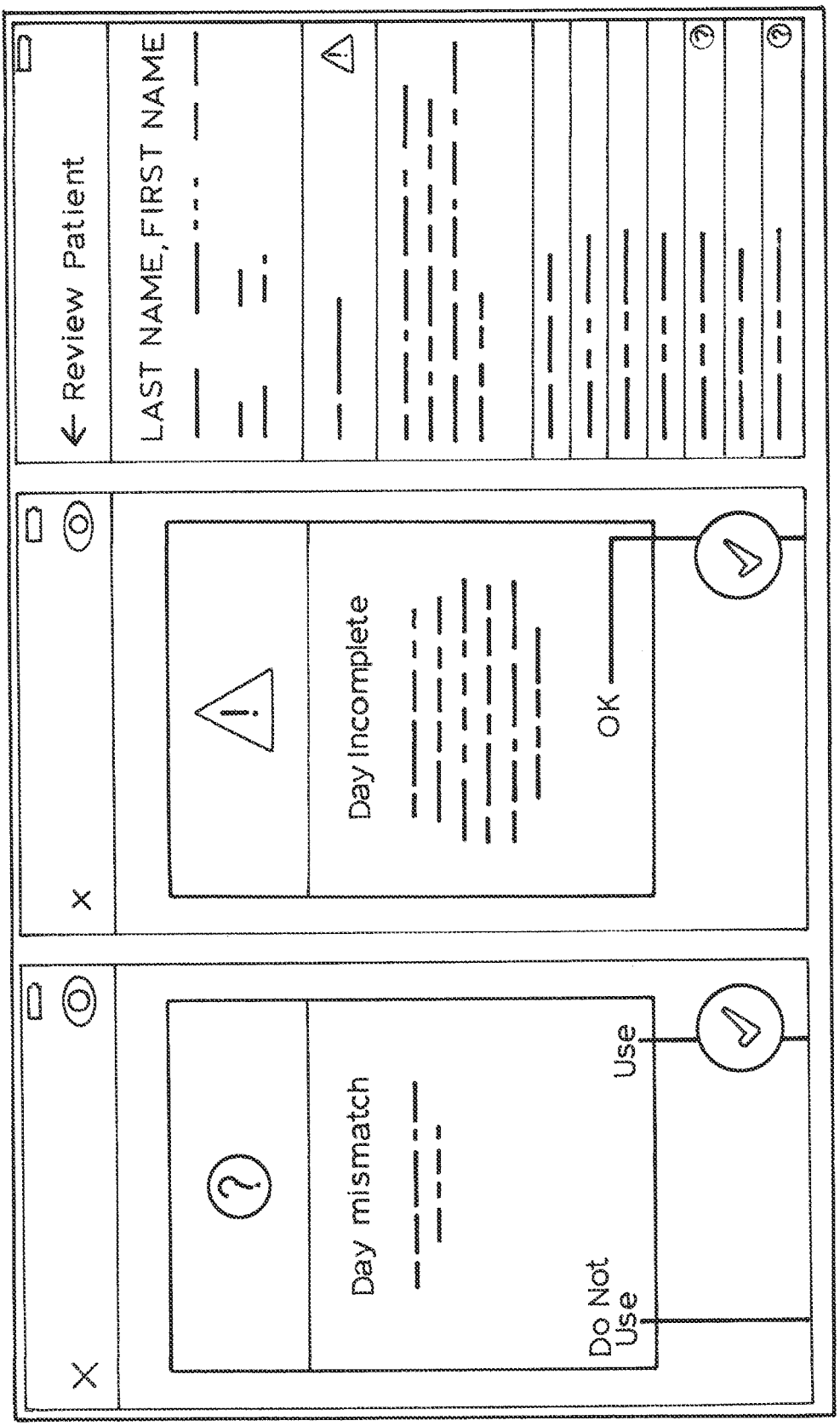
Figure 18:
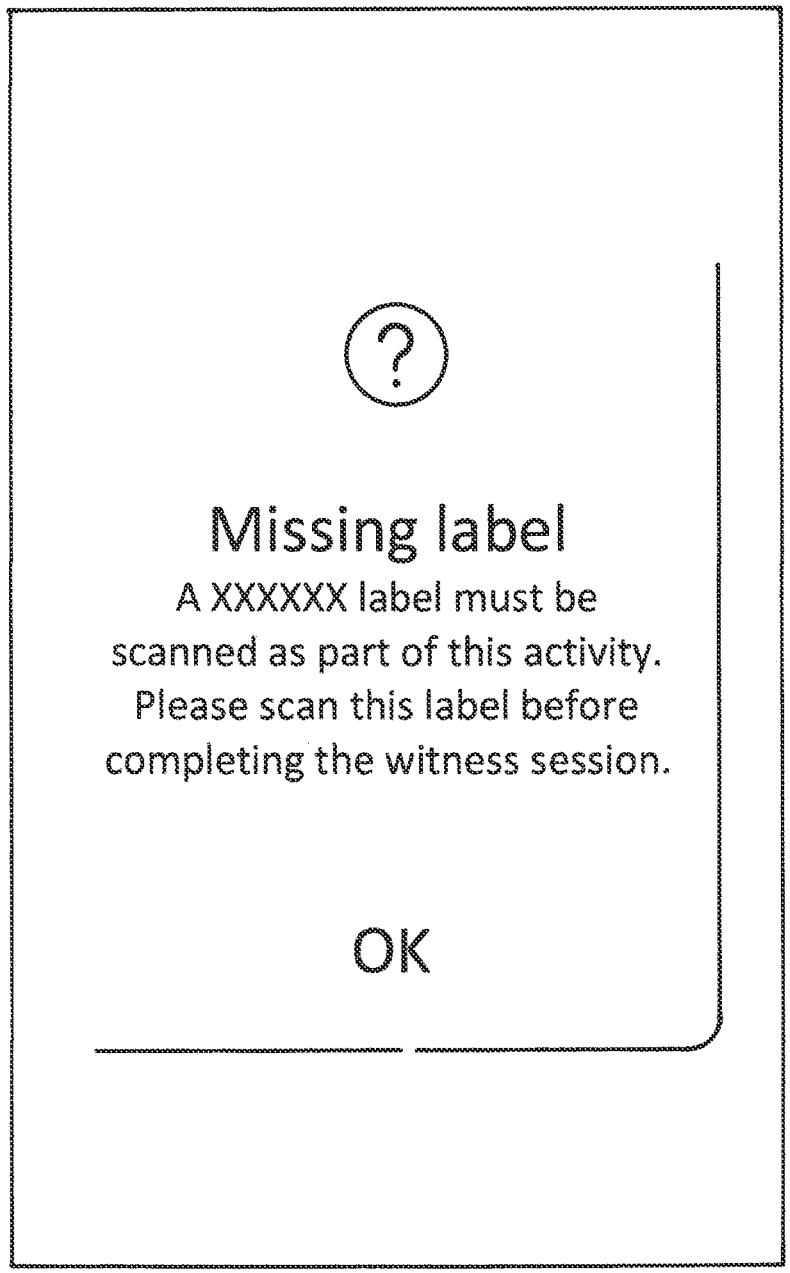

An example of the steps to define labels and print groups is illustrated in FIGS. 12 to 14 from a user interface perspective. The format is shown in FIG. 12. The input for adding and defining the label format is illustrated in FIG. 13, where consumables with more than one part can be catered for with the same label creation. As shown in FIG. 14, the labels can then be assigned to cycles for printing. In accordance with correlating the labels with the cycle/day, FIGS. 15 and 16 illustrate the activities and rules that can be established. Of the label library that is created, certain labels are assigned to the associated development day of the cycle and must be scanned accordingly. Labels are assigned to the day(s) on which they are scanned and as the laboratory/clinic operates, critical labels or activities for each day are selected. Icons of the user interface can be invoked to set rules. For example, a label can be linked to other labels to define a set of labels that must be scanned for a specific activity. Another example is that a rule may be set that defines labels that must be scanned for a particular day to be considered complete. By way of example, a rule can be set in which a label must be scanned for every witness session. FIG. 16 shows an interface display that enables the user to define rules for certain lab activities. FIGS. 17 and 18 show a user interface displayed message resulting from process flow checks where the set rules are applied an in so doing, incompatibilities, errors and missed steps are reported. A "Day mismatch" and "Day incomplete" message are shown as examples in FIG. 17.

Figure 42:
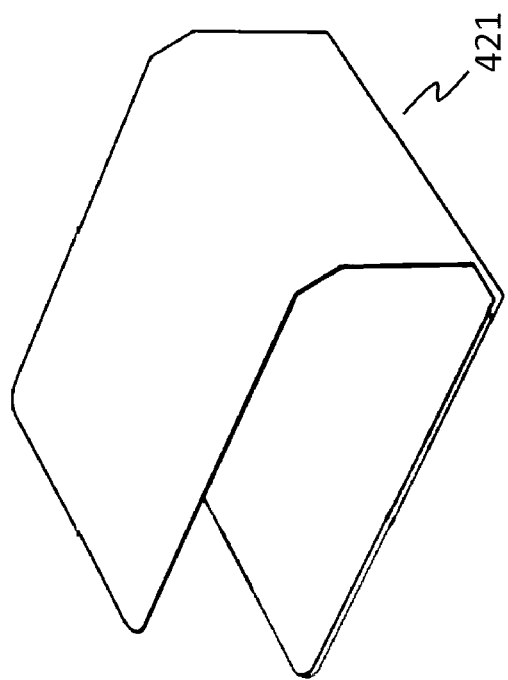
FIG. 42 shows an exemplary labelling of a biological sample incorporated into the cassette of FIGS. 41a and 41b in accordance with a preferred embodiment.

Preferred forms of identification labels include adhesive-backed paper labels or the like and microelectromechanical (MEMS) devices. An example of a label in use is illustrated in FIG. 42 at 421.

Software embedded in the reader/scanning devices 6 control their interaction with external technology devices (which are not illustrated in FIG. 1) and control their interactions with the database server of the central computer 2. Preferred aspects of that software include the following.

According to some preferred embodiments of the invention, the devices 6 do not store sensitive patient information, but the software only links it from the appropriately secured patient management databases within the database server of central computer 2. According to alternative preferred embodiments of the invention, the software has the ability to synchronise the input data in real time across the central system and across multiple devices in the same system with the database server and with multiple other hand-held devices 6.

The software contains operation and/or transaction logs and an audit log.

The software contains customisable process maps.

The software is customisable to interact with different patient management databases.

The software has the ability to track to the level of individual eggs and embryos from the same patient, across several ART cycles from the same patient, and across several combinations of gametes (e.g. sperm donors, different partners)

The software has the ability to manage tracking of diverging paths, for example multiple containers joined into one, or one biological material split across multiple diverging process paths Description of Operation The system operates by capturing data during the ART cycle and generating messages to an operator as confirmation, warning or alarm of the correctness of some condition. In particular, the devices 6 have the in-built software and functionality to perform actions of capturing data, performing a comparison of that data with reference data, and generating a confirmation, warning or alarm depending on the outcome of that comparison as is described in more detail herein. Preferably the devices 6 have additional functionality to perform tasks which do not involve the performing of a comparison. It is accordingly preferred that the hand-held devices 6 perform any one of, or a combination of, the following processing:

As is illustrated by way of example in the screen captures of FIGS. 22 to 32, the capture of data about the individual operator who is using the device.

The capture of identity data concerning the patient. This data includes data identifying the patient who is undergoing a procedure and patient identity data which is captured from vessels, stores and the like which store or hold the patient's biological material, and from sources which record the patient's test results. The data identifying the patient, and the patient identity data which is gathered from vessels, stores or the like is compared. Depending on the results of the comparison, the hand held devices 6 generate the appropriate one of a confirmation, a warning and an alarm to the operator.

The capture of process steps and the comparison of the captured process steps with a built-in customisable process map. Depending on the results of the comparison, the hand held devices 6 generate the appropriate one of a confirmation, a warning and an alarm to the operator, depending on the correctness of the step within the process.

The capture of the qualifications of the operator and their comparison with the customisable staff matrix to generate the appropriate one of a confirmation, a warning and an alarm to the operator, depending on the correctness of the operator's qualifications to perform the process.

The capture of information about the timing of the process steps and the order in which they were performed.

The capture of information about the environment and environmental parameters (for example temperature, humidity, $CO_2$ levels) during the process steps.

The capture of information about the operator's performance of the process steps to feed into customisable training and/or a KPI (key performance indicators) matrix.

The capture of information about the location of gametes and embryos.

The capture of information about the lot numbers, batch numbers, expiry dates and other information about the materials and consumables used during the process; and the linking of that information:
  to a supply tracker to generate the appropriate one of a confirmation, a warning and an alarm to the operator, depending on the suitability of the product for the process; and
  to a customisable organisation supply chain tracker or inventory system to generate the appropriate one of a confirmation, a warning and an alarm to the operator, depending on the inventory levels and the leadtime for the specific products.

The capture of information about the equipment used, their service, calibration and operational status and other information to generate the appropriate one of a confirmation, a warning and an alarm to the operator, depending on the suitability of the equipment to be used for the process.

The capture of all the above information about ID (including the location of a device 6 within the laboratory), process steps, operator, materials and equipment to generate the appropriate one of a confirmation, a warning and an alarm to the operator, depending on their combined appropriateness for the process.

The linking of all the information captured to the individual patients/embryos journey through the complete ART process. According to alternative preferred embodiments of the invention, this linking is performed, at least in part, by other devices within the system.

The capture of all deviations, warnings and alarms to a separate record that can be used for QA and QC purposes, audits and training needs. According to alternative preferred embodiments of the invention which are not illustrated in the drawings, this capture is performed, at least in part, by other devices within the system.

Customisable data matrix to capture and store relevant information for clinic's accreditation, audit or internal KPI purposes. According to alternative preferred embodiments of the invention which are not illustrated in the drawings, this linking is performed, at least in part, by other devices within the system 1.

In a process according to a preferred embodiment:
the day in an ART cycle on which an egg cell from one given patient is to be fertilized with a sperm cell from another given patient is arbitrarily assigned the label of "Day Zero" or, alternatively, "Day 0"; and in accordance with accepted timelines for incubation, which range from Day 0 to Day 5 or Day 6 (noting there has been some recent consideration of incubating until Day 7), each subsequent day for that ART cycle is numbered consecutively from Day Zero onwards. For example, if a fertilized egg cell is to be incubated for 5 days, incubation will be completed on "Day 5" and the next step in that ART cycle will take place on "Day 6".

Figure 20:
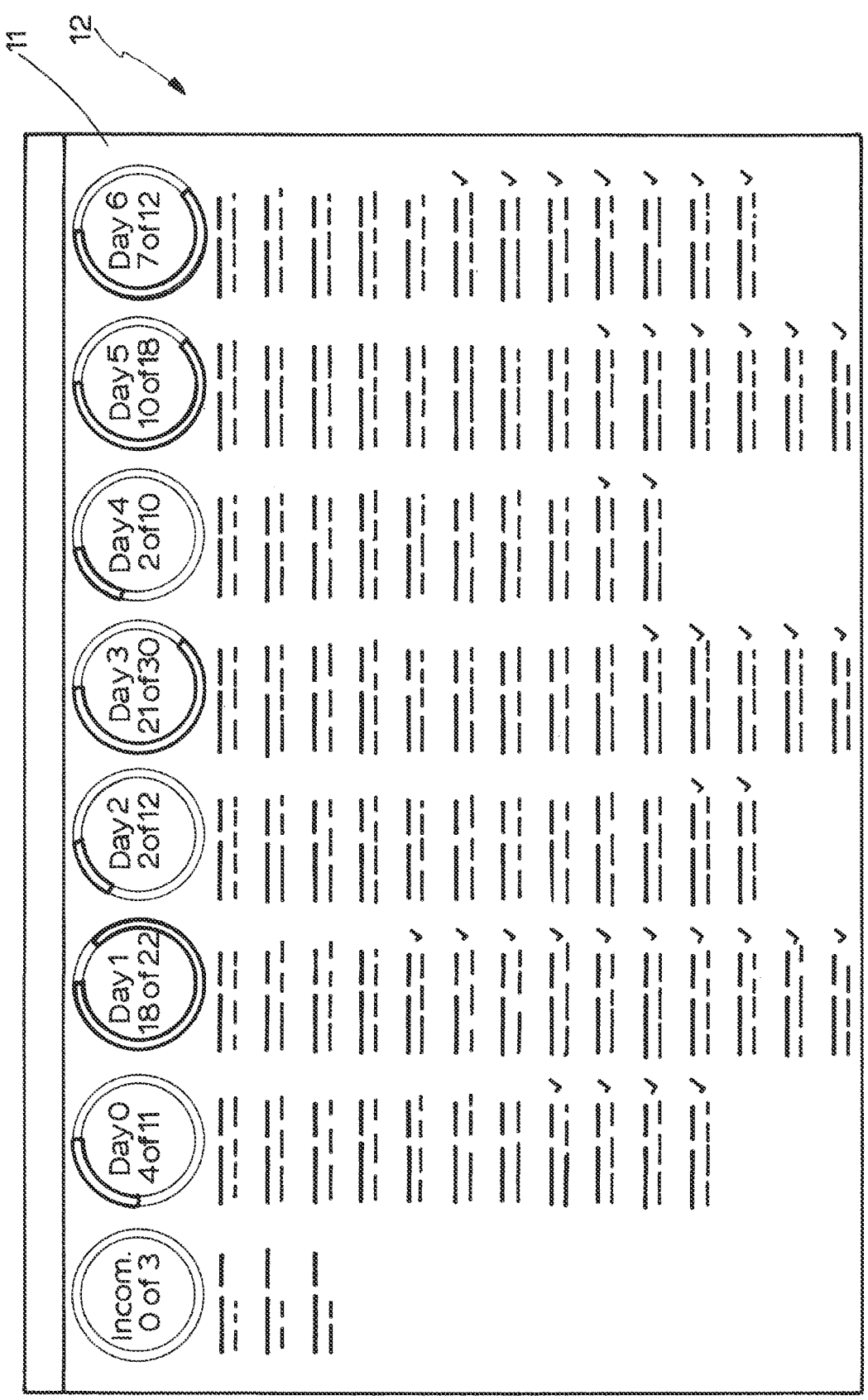
FIG. 20 shows a display suitable for web access of an overview of all current patients in a laboratory management system in the form of a dashboard display according to a preferred embodiment.

As is illustrated by way of example in FIG. 20, a comprehensive display of the status of every ART procedure which is underway in an ART clinic is presented in the form of a list named "Today's Active List" indicated by 12 and is readily displayed on a hand held device 6 or via a web accessible application in accordance with embodiments. The active list is also able to display previous day or upcoming day for planning purpose. That Active List is arranged in rows and columns. Each column is headed with a label which identifies the current day of all of the ART procedures which are being processed in the clinic. The contents of the column is a listing which identifies the patients whose procedures have reached that day of the ART cycle. A dashboard display 11 is also presented with the column label/headings which provides a ready indication of progress for samples according to their allocated days of the samples' development timeline.

In the Active List:
  for a patient whose ART cycle has completed the processing for that day, the identifier of the patient is greyed-out or otherwise marked to indicate that processing for the process for that day has been completed. FIG. 20 illustrates this with a tick shown next to such entries;
  for a patient in respect of whom there has been an error in processing, or an attempt to perform erroneous processing, the identifier of the patient is highlighted in red or otherwise marked to indicate an error, and remains marked until that error is corrected; and
  for a patient in respect of whom the processing necessary on that day has not yet been completed, the identifier of the patient is not marked.

Figure 19:
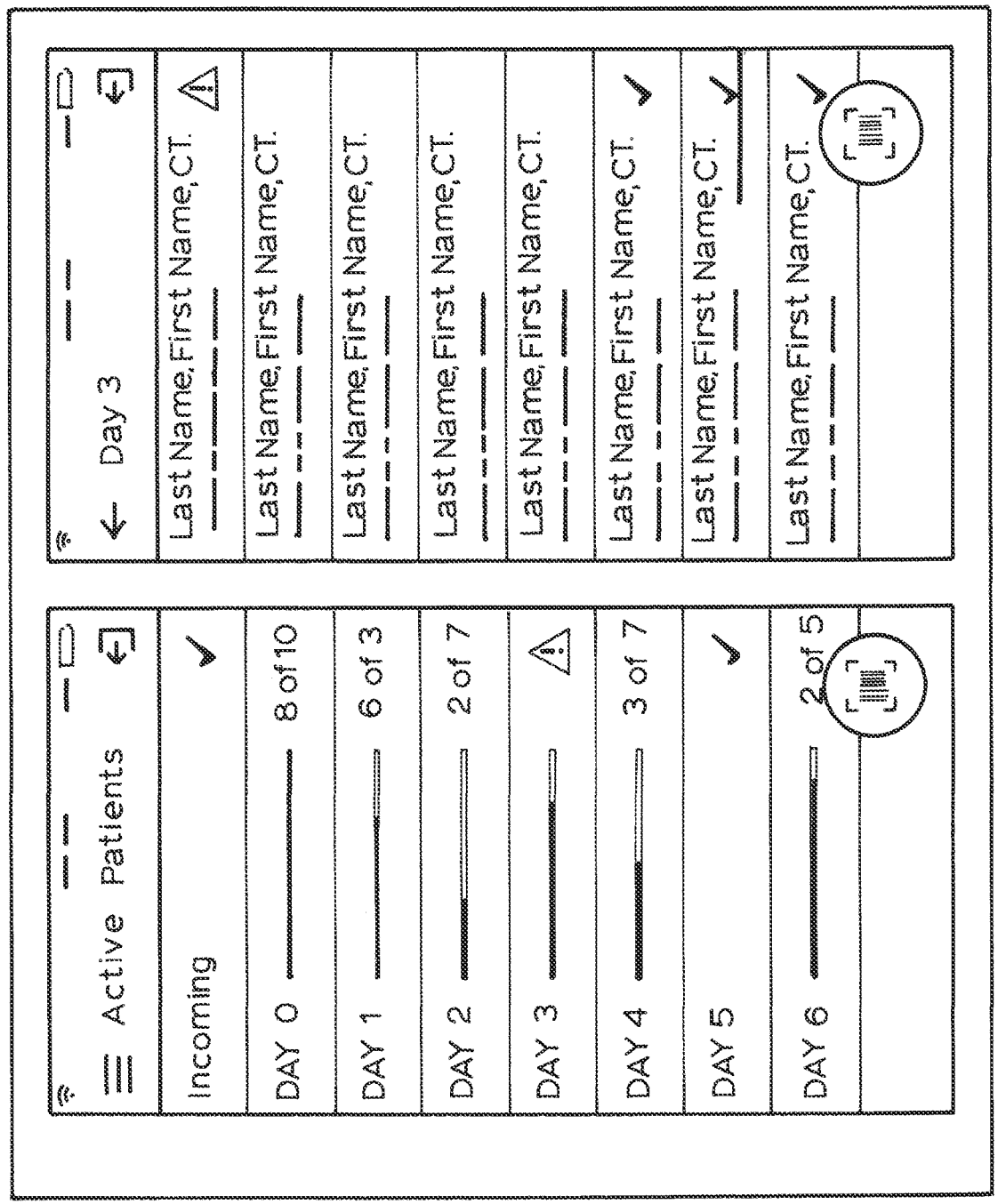
FIG. 19 shows a hand held display of an overview of all current patients in a laboratory management system according to a preferred embodiment.
Figure 21:
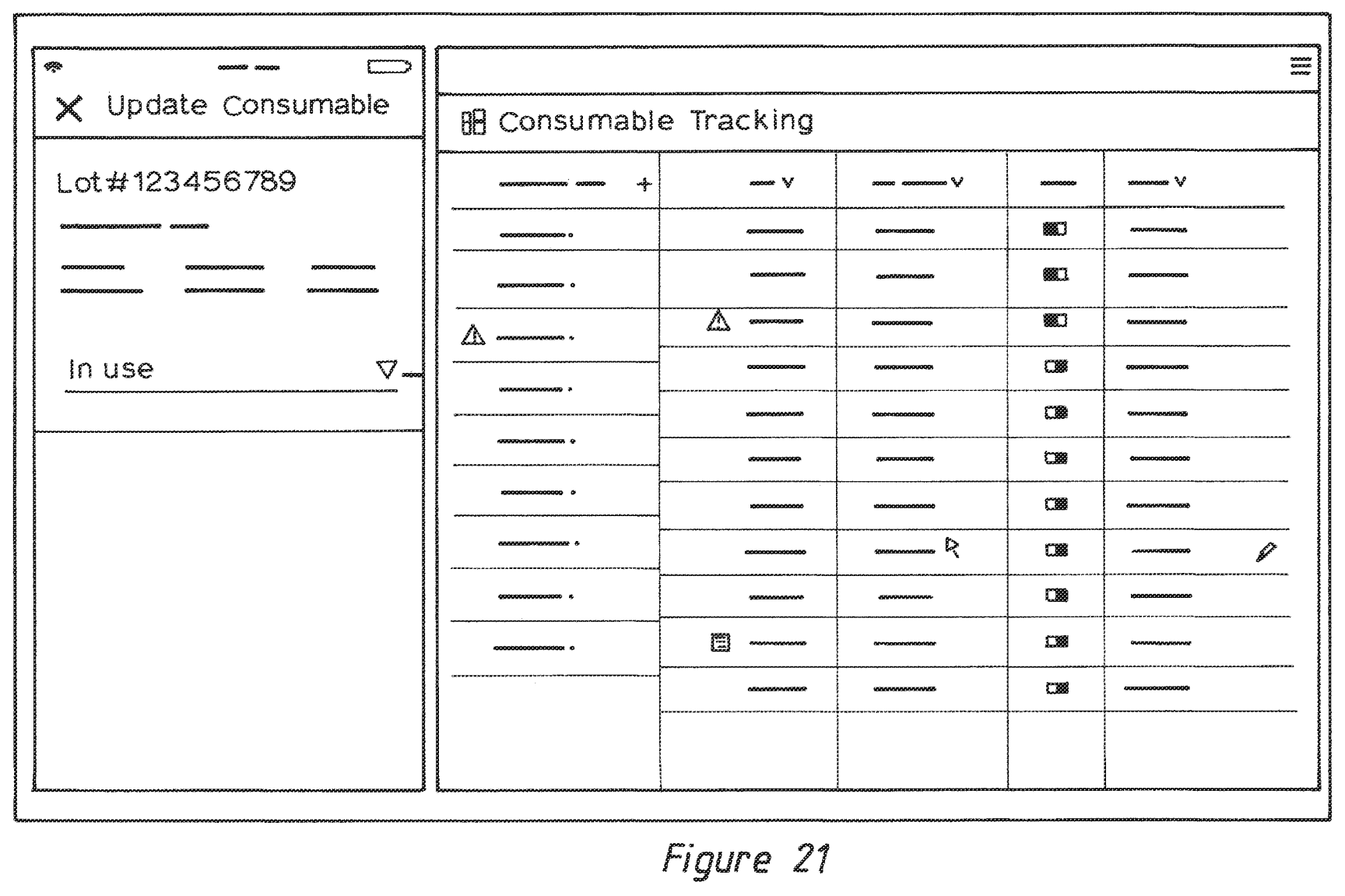

From the perspective of the user utilising a hand held device 6, a general laboratory overview can be gained as illustrated in FIG. 19. Equally, an indication of a laboratory overview can be shown via web access as illustrated in FIG. 20 where the dashboard display is provided. A specific function such as consumable management is displayed in FIG. 21.

Aspects of the operation of the hand-held devices are illustrated in the flow-charts of FIGS. 22 to 32 and in the data input and output screens of FIGS. 12 to 19, and 21 for example and are explained in further detailed herein.

Figure 22:
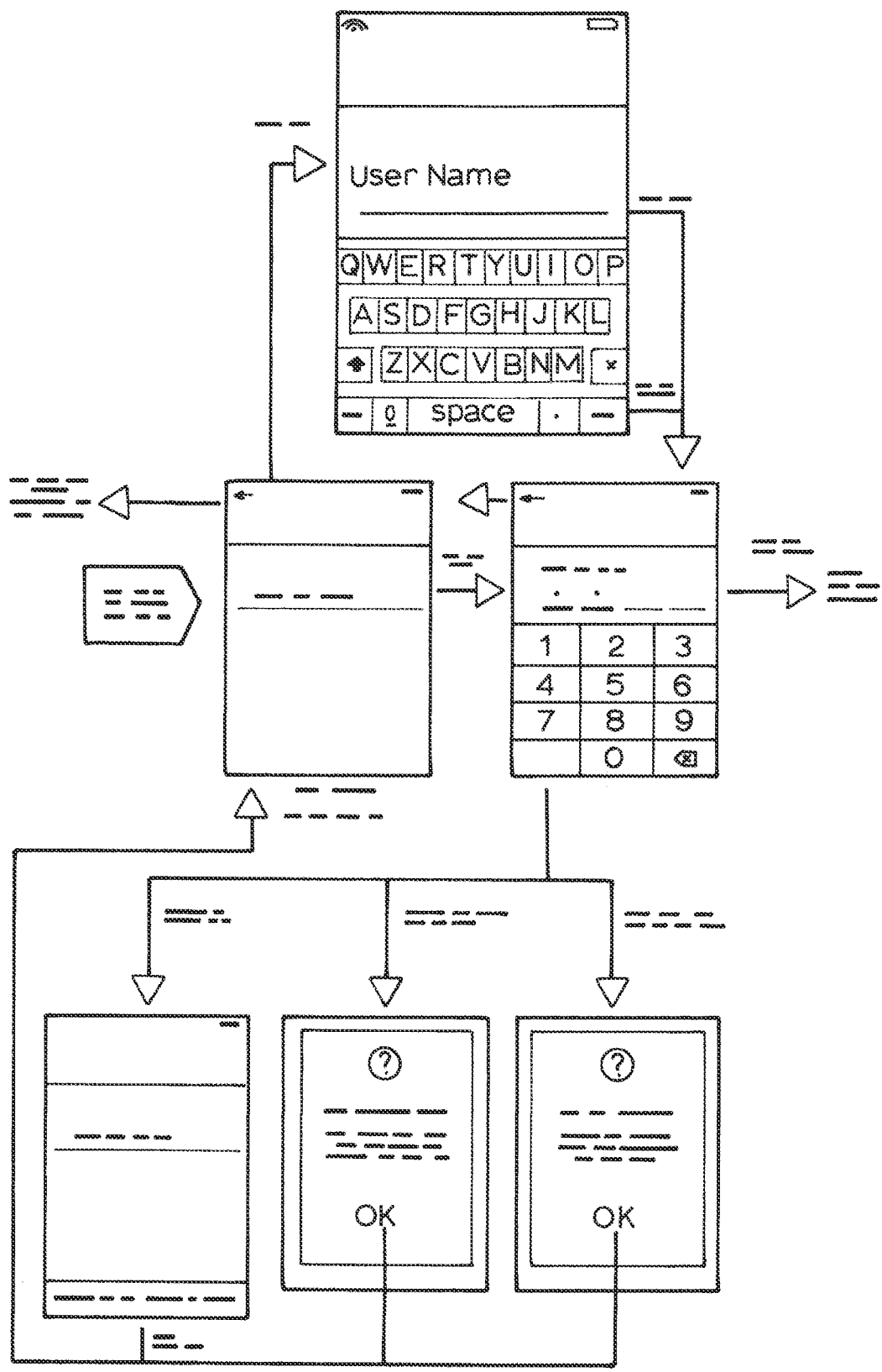
FIG. 22 shows, from the aspect of a user interface, an exemplary login process for a user in accordance with a preferred embodiment.

With reference to FIG. 22, in operation, the first screen the user encounters upon login is the Active Patient screen. FIG.

Figure 23:
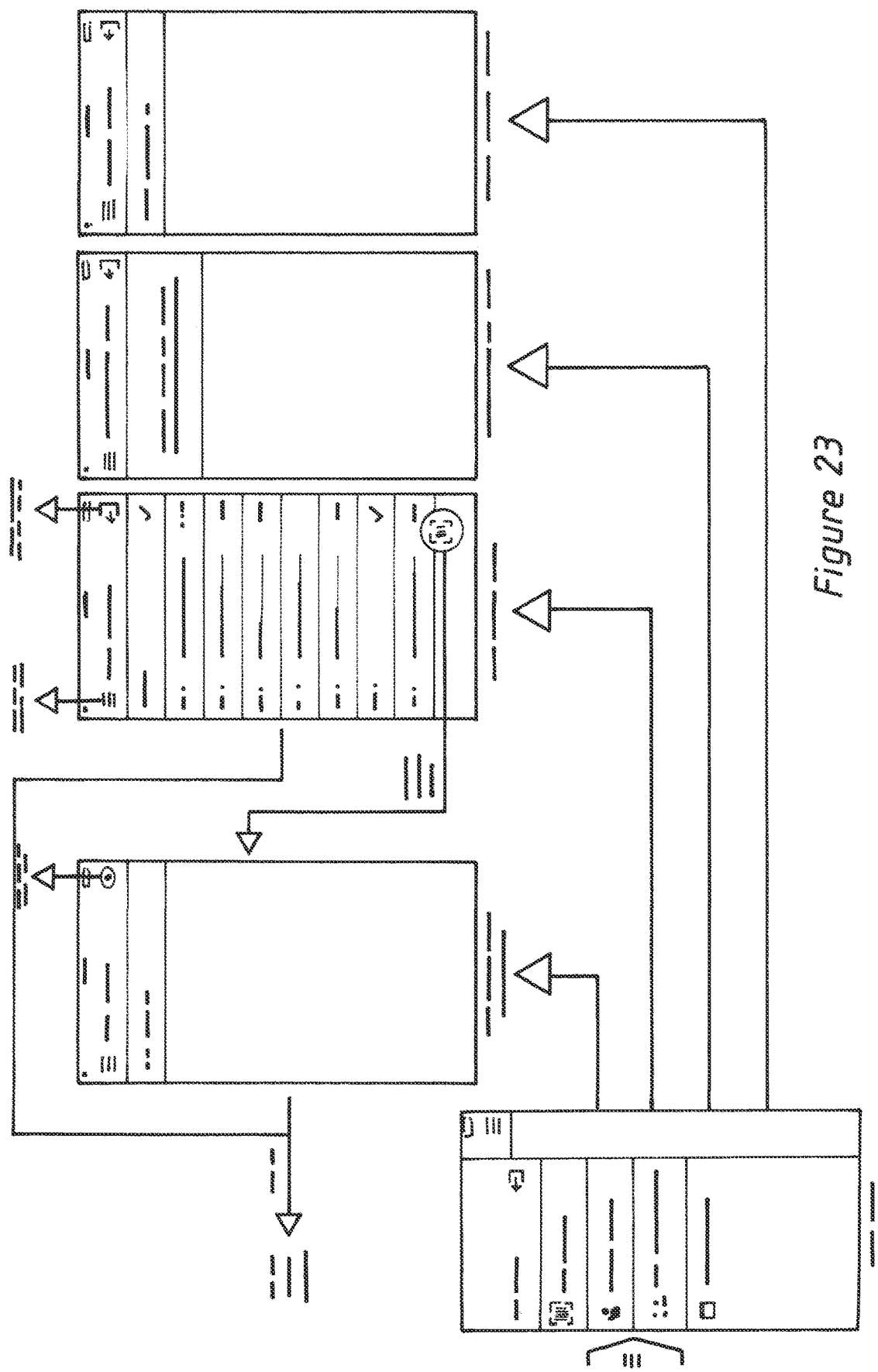
FIG. 23 shows, from the aspect of a user interface, an exemplary menu and screen displays for instigating a sample scan session in accordance with a preferred embodiment.

22 shows all possible outcomes a user may prompt, in flow chart form, when logging in. FIG. 23 shows all possible outcomes a user may prompt when using the App menu, which provides for the functionality of Scan Session; Active Patients; Track Consumables and; Patient History. The outcomes when instigating a Scan Session are also illustrated in FIG. 23.

With reference to FIGS. 24a to 24e, scenarios for scanning are able to be accommodated for an automated witnessing. Within this feature the user can run an automated witnessing session for a given patient activity. Rules applied to labels (specified within the accompanying web app) allow for a multitude of user errors to be flagged and mitigated.

Figure 24A:
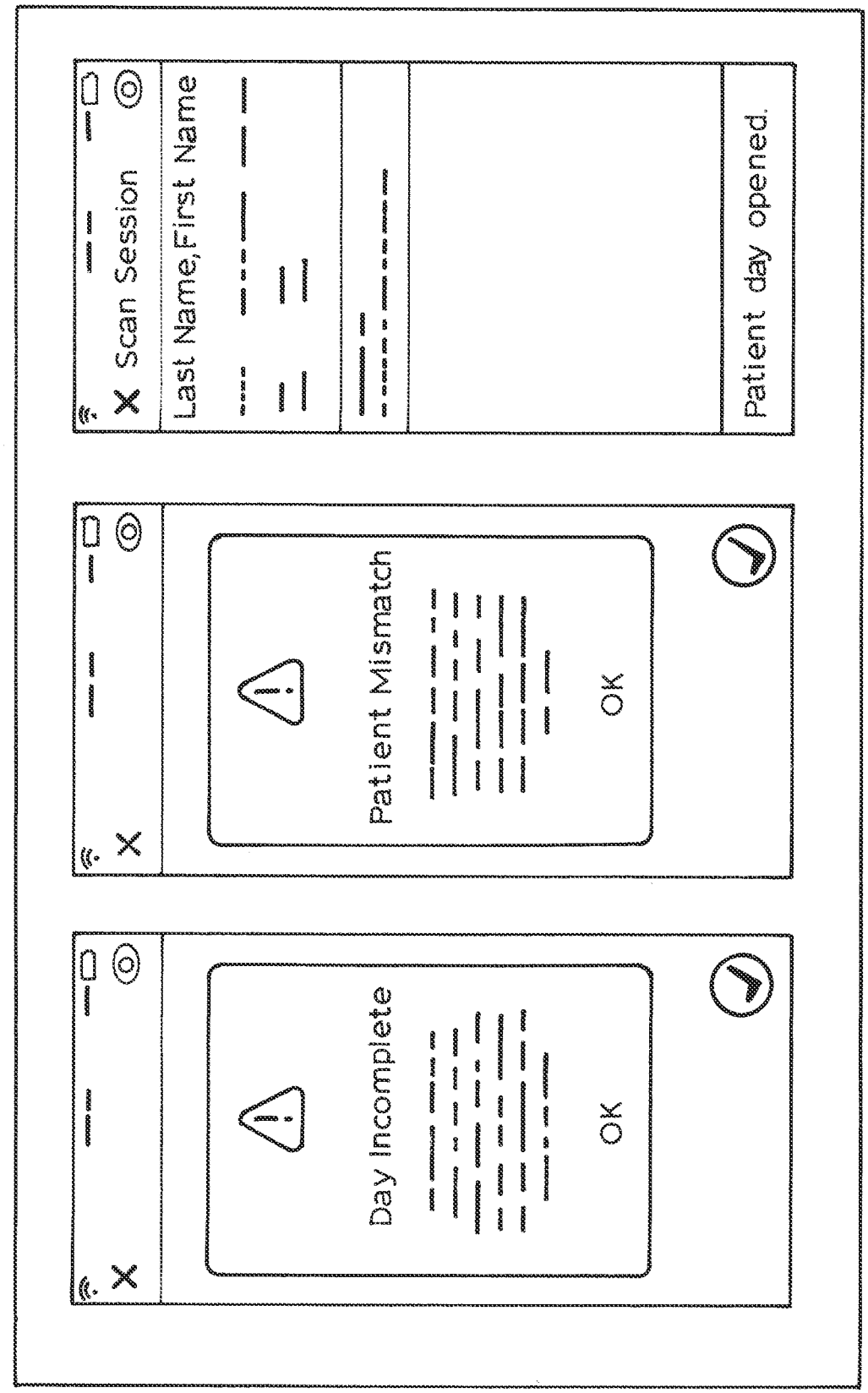
FIGS. 24a to 24e shows, from the aspect of a user interface, an exemplary series of screen displays within a scan process in accordance with a preferred embodiment indicating example errors being flagged.
Figure 24B:
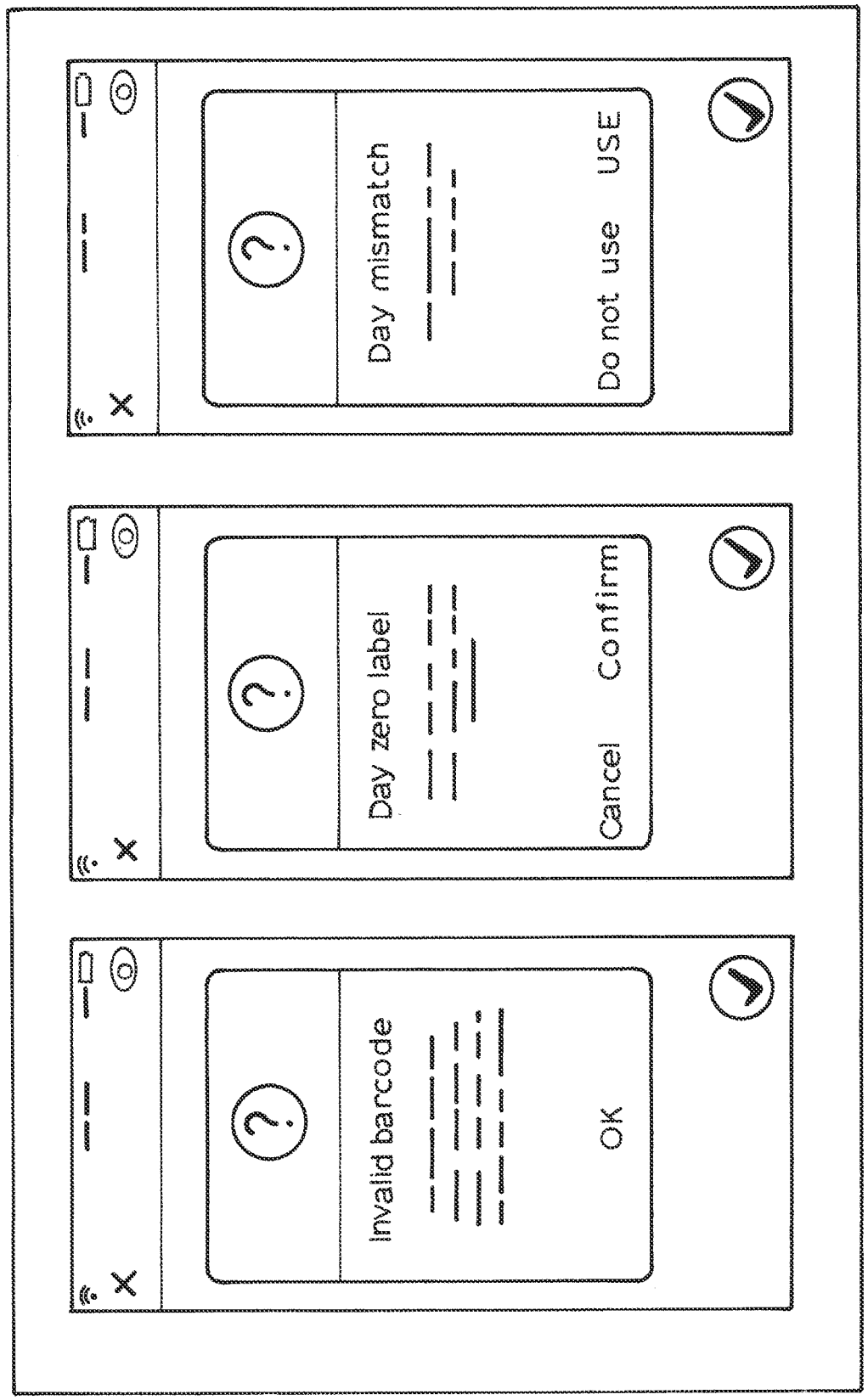
Figure 24C:
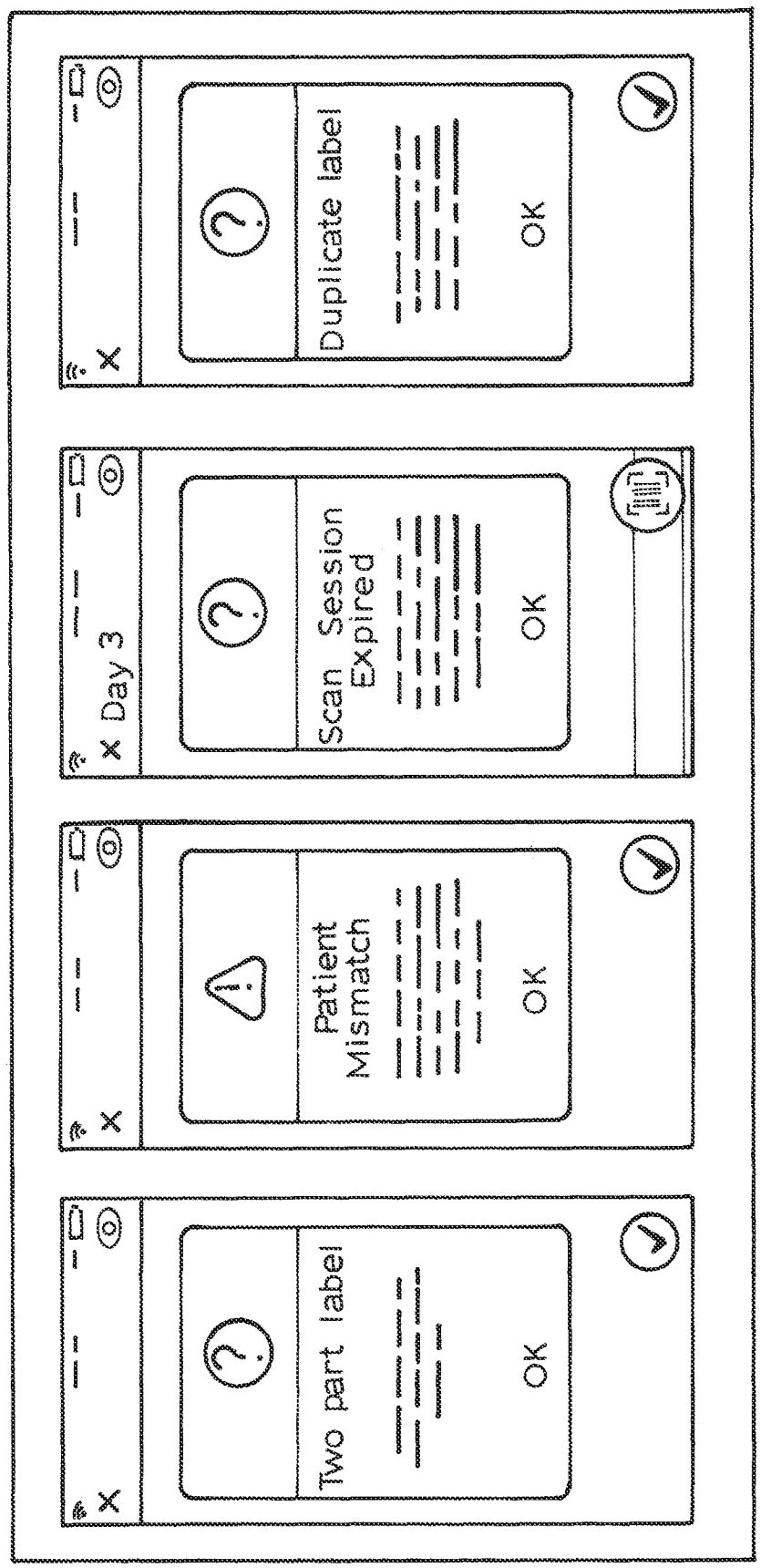
Figure 24D:
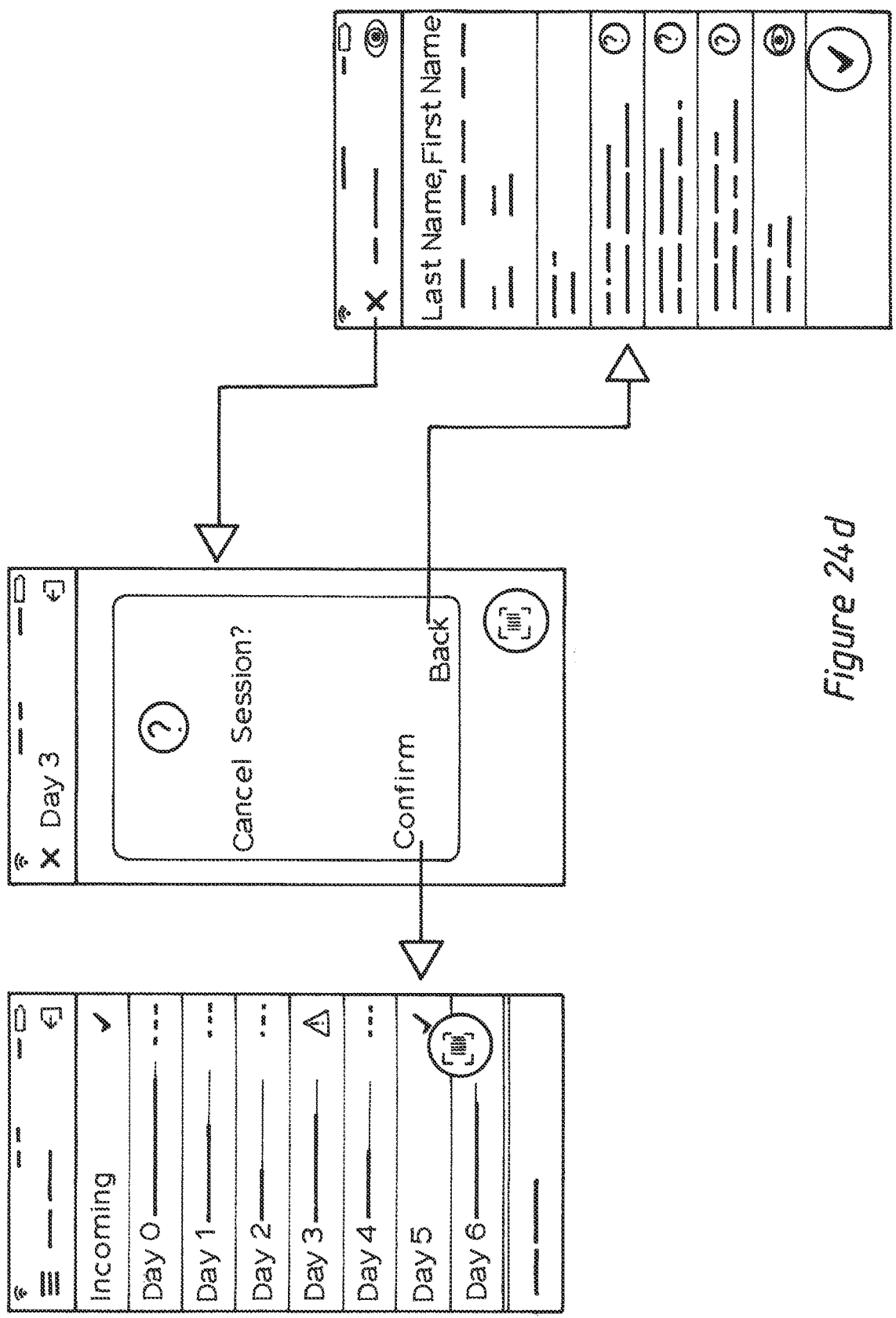
Figure 24E:
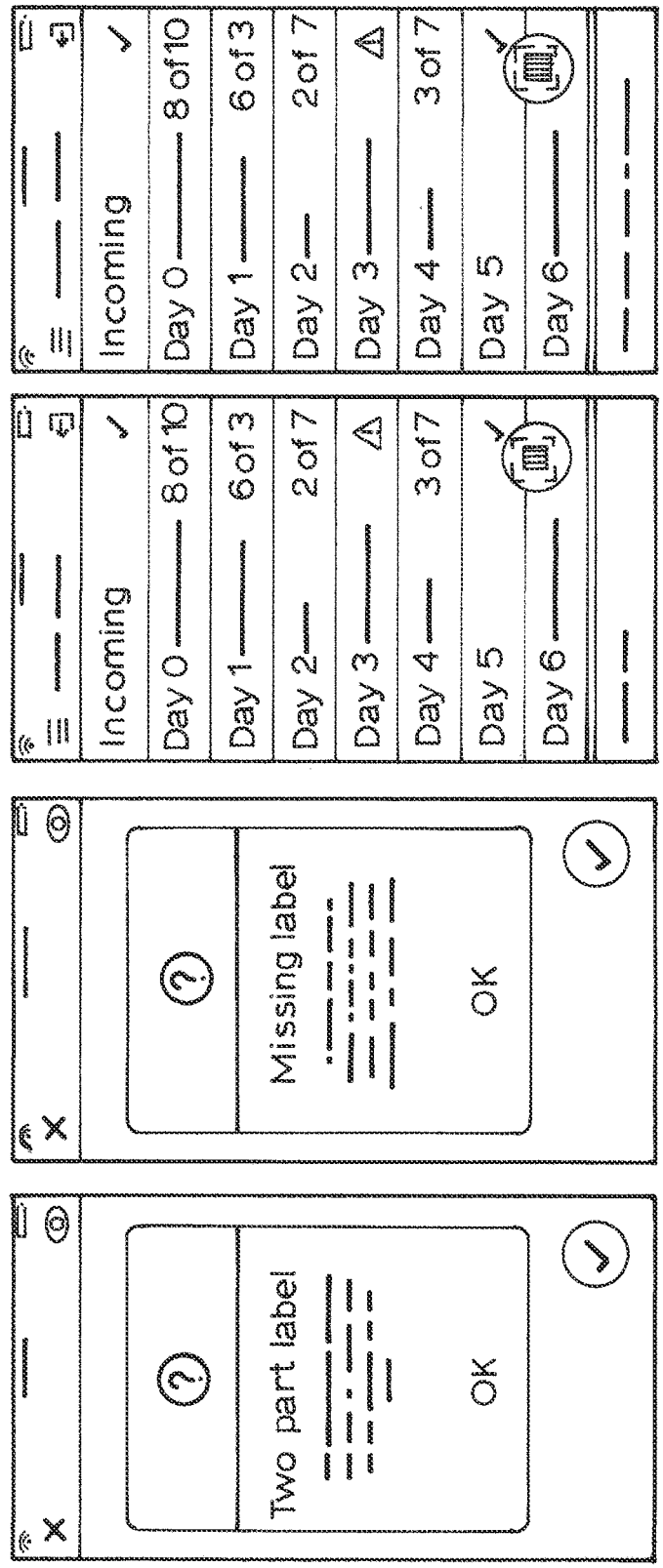

In a first case scenario, a first patient label is scanned/entered upon 'START' and progressing to the workflow options shown in FIG. 24a being one of: a "Day Incomplete" alert message is displayed and the user is returned to the login screen if a 'previous day' is incomplete based on the label rules; a "Patient Mismatch" alert message is displayed and a return to the active patient screen if a patient label is scanned that is already locked because of a patient mismatch or; if no mismatch or other error occurs then the system allows the user to proceed with a scan of a container label for a patient who has been manually set to day/cycle complete and proceeds with an auto patient open screen and then to possible flows of FIG. 24d or 24e.

In a second case scenario either the first patient label is scanned/entered or, at least one patient label has already been scanned/entered upon 'START' and unless the errors or oversights of FIG. 24b, i.e. 'Invalid barcode', 'Day zero label' or 'Day mismatch' occur progressing to workflow options shown in FIG. 24d or 24e.

In a third case scenario at least one patient label has already been scanned/entered and, where one of the four options of FIG. 24c may be progressed.

Figure 25:
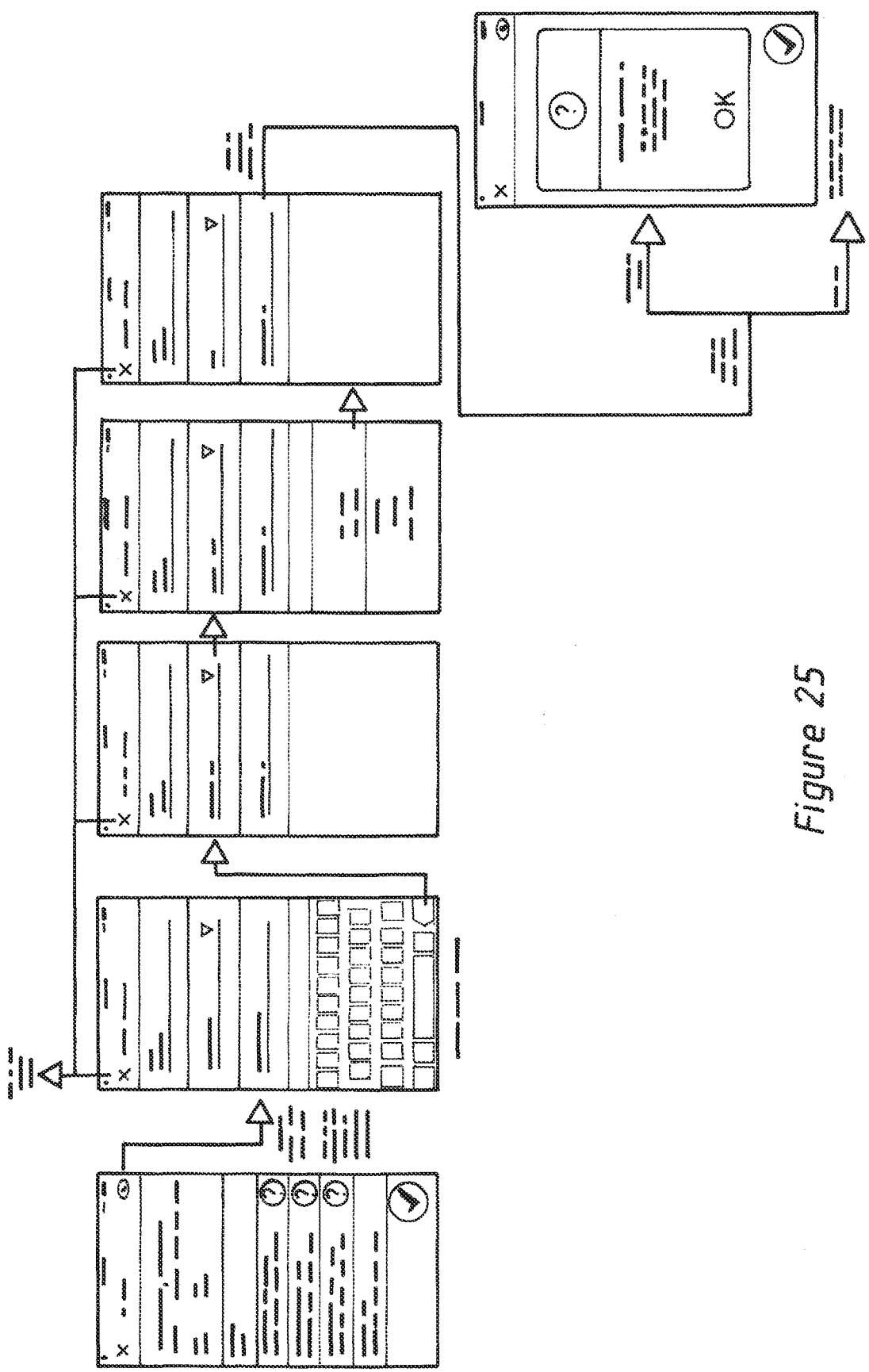
FIG. 25 shows, from the aspect of a user interface, an exemplary process for facilitating manual witnessing in accordance with a preferred embodiment.

With reference to FIG. 25 a manual witnessing process can be managed and the flow chart illustration of FIG. 25 shows the possible outcomes for the manual witnessing procedures. Manual witnessing allows the user to enter patient details manually that cannot be scanned or to be witnessed by a colleague and furthermore the labels may also be photographed for future reference.

Figure 26:
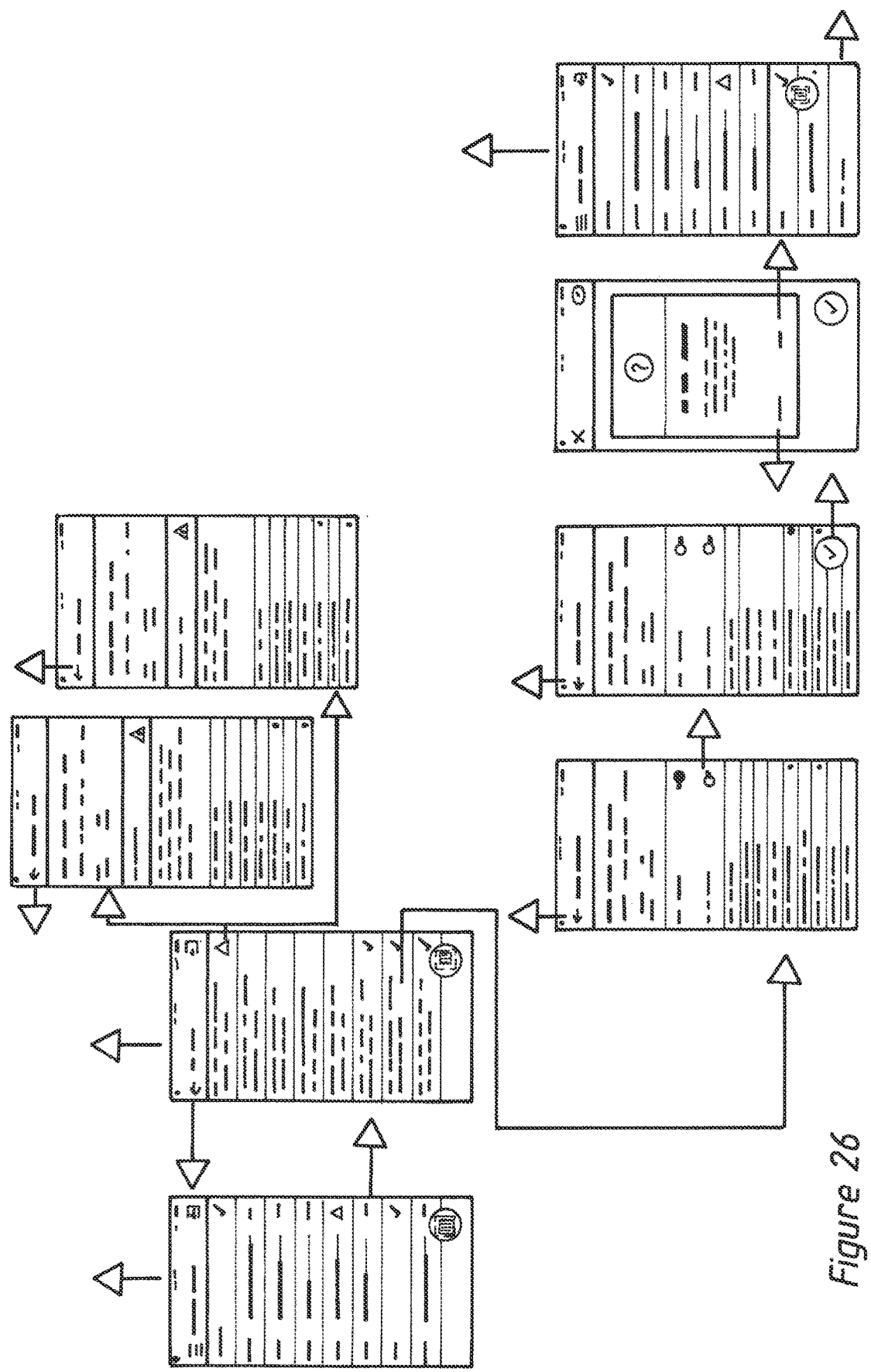
FIG. 26 shows, from the aspect of a user interface and in accordance with a preferred embodiment, an exemplary menu and screen displays for managing patient tasks within a working day where the tasks are sub-divided into the days of the biological sample development cycle.

With reference to FIG. 26 all possible outcomes of the menu within the Active Patient menu item are illustrated. The Active Patient list shows all the patient tasks for the working day sub-divided in days of the cycle. Within the feature the user can see the progress for the day, identify which patient tasks are complete, which patient tasks have errors associated with them, they can review the past five scan sessions for a given patient and close/open a day/cycle for a given patient.

Figure 27:
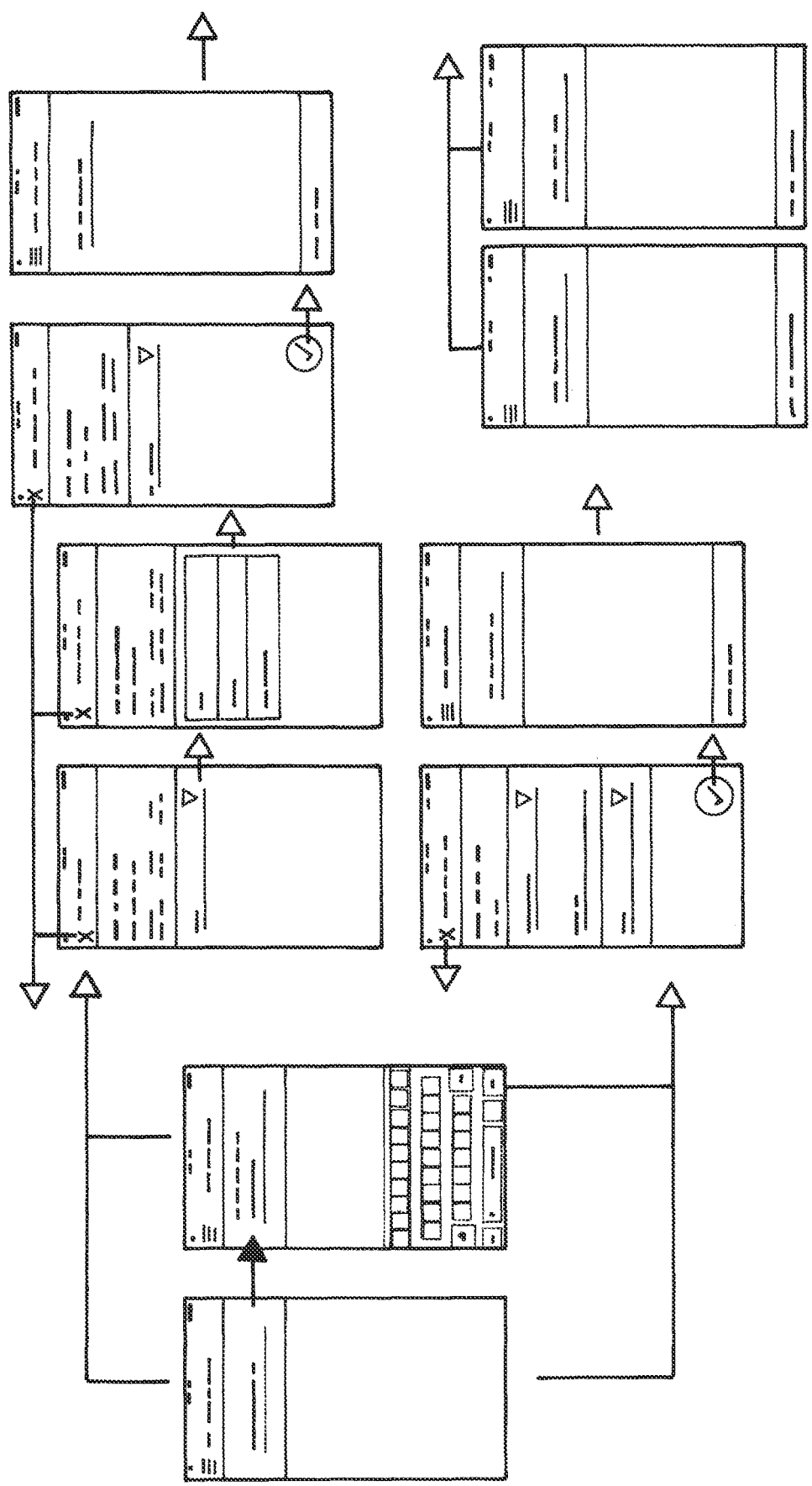
FIG. 27 shows, from the aspect of a user interface, an exemplary menu and screen displays for tracking consumable items in accordance with a preferred embodiment.

With reference to FIG. 27 all possible outcomes of the menu within the consumable tracking menu item are illustrated. The consumable tracking feature provides the ability to add a new consumable or change the status of a consumable that already exists on the system. The consumable tracking allows for a check for expiry dates and pre-warn users of expired inventory. It also allows the traceability to consumables against each patient.

Figure 28:
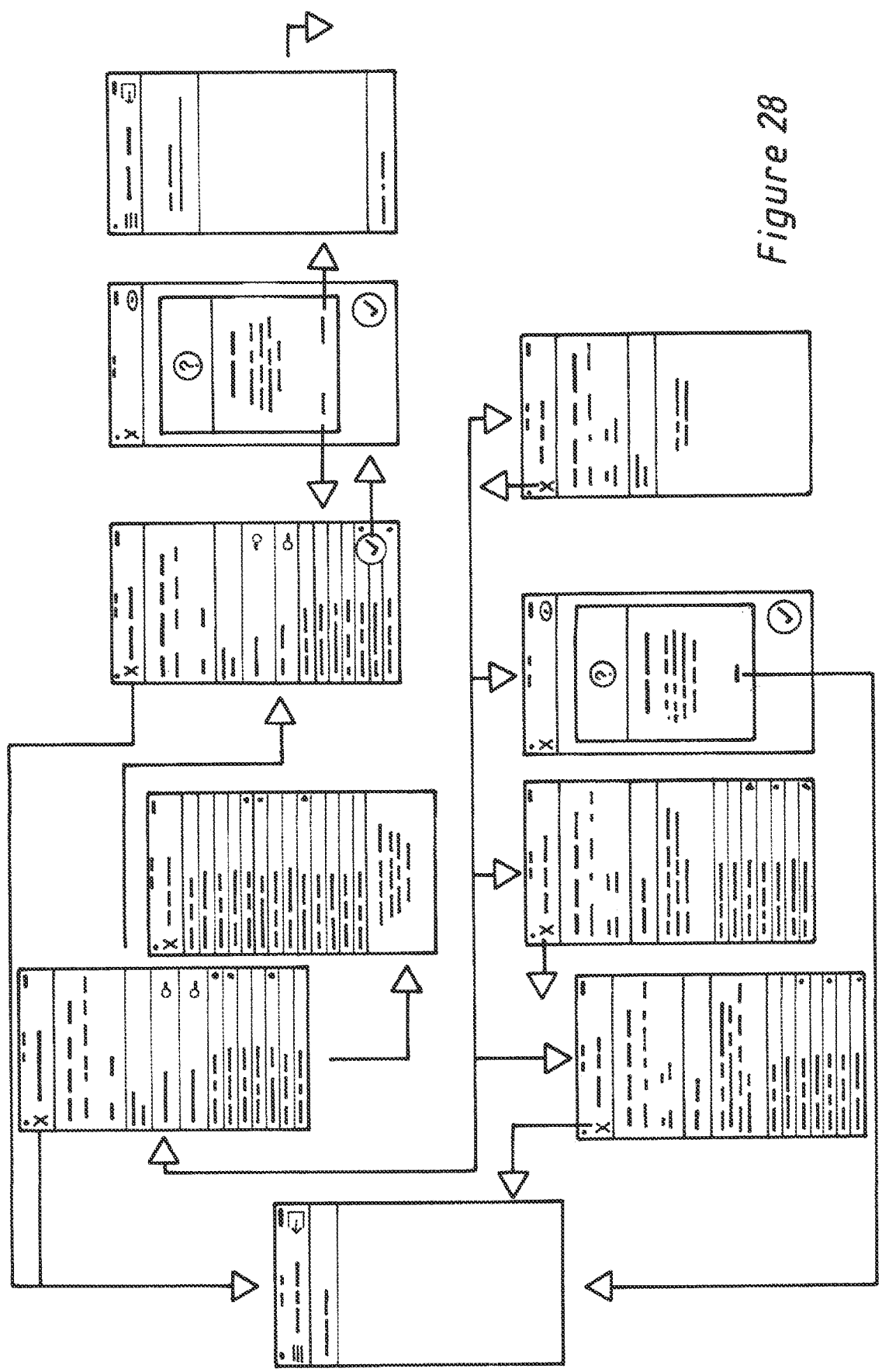
FIG. 28 shows, from the aspect of a user interface, an exemplary menu and screen displays for a user to review a patient history within the laboratory workflow and indicating example errors being flagged in accordance with a preferred embodiment.

With reference to FIG. 28 all possible outcomes within the patient history menu item are illustrated. The patient history feature allows the user to review the past five scan sessions for a patient and manually change the cycle status via scanning any patient label.

Timeout and lock out procedures for the hand held device 6 can be implemented in one of a number of ways that would be appreciated by the person skilled in the art.

Figure 29:
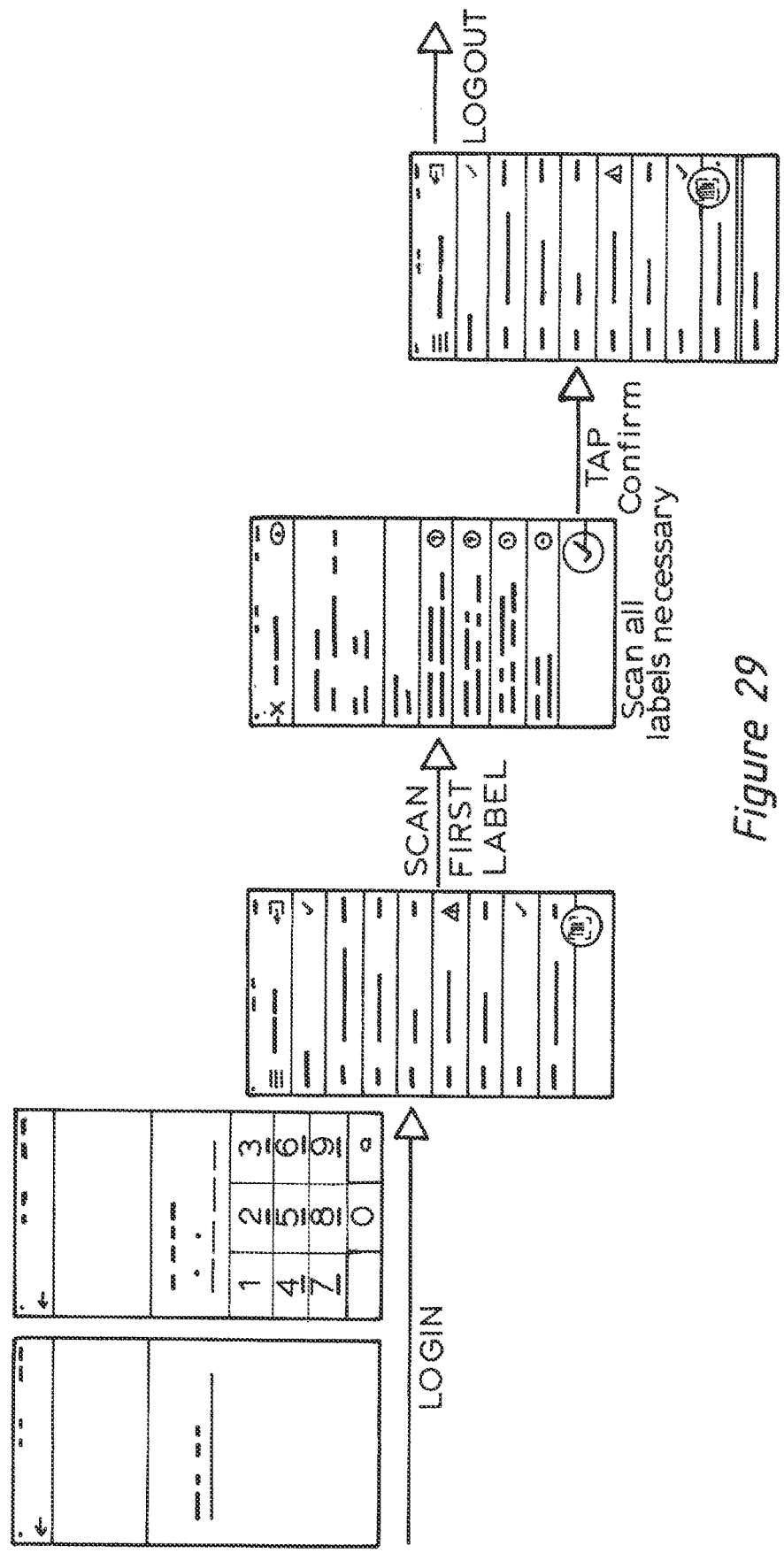
FIG. 29 shows, from the aspect of a user interface, an exemplary series of screen displays within a scan process illustrating an expedited scan session in accordance with a preferred embodiment.
Figure 30:
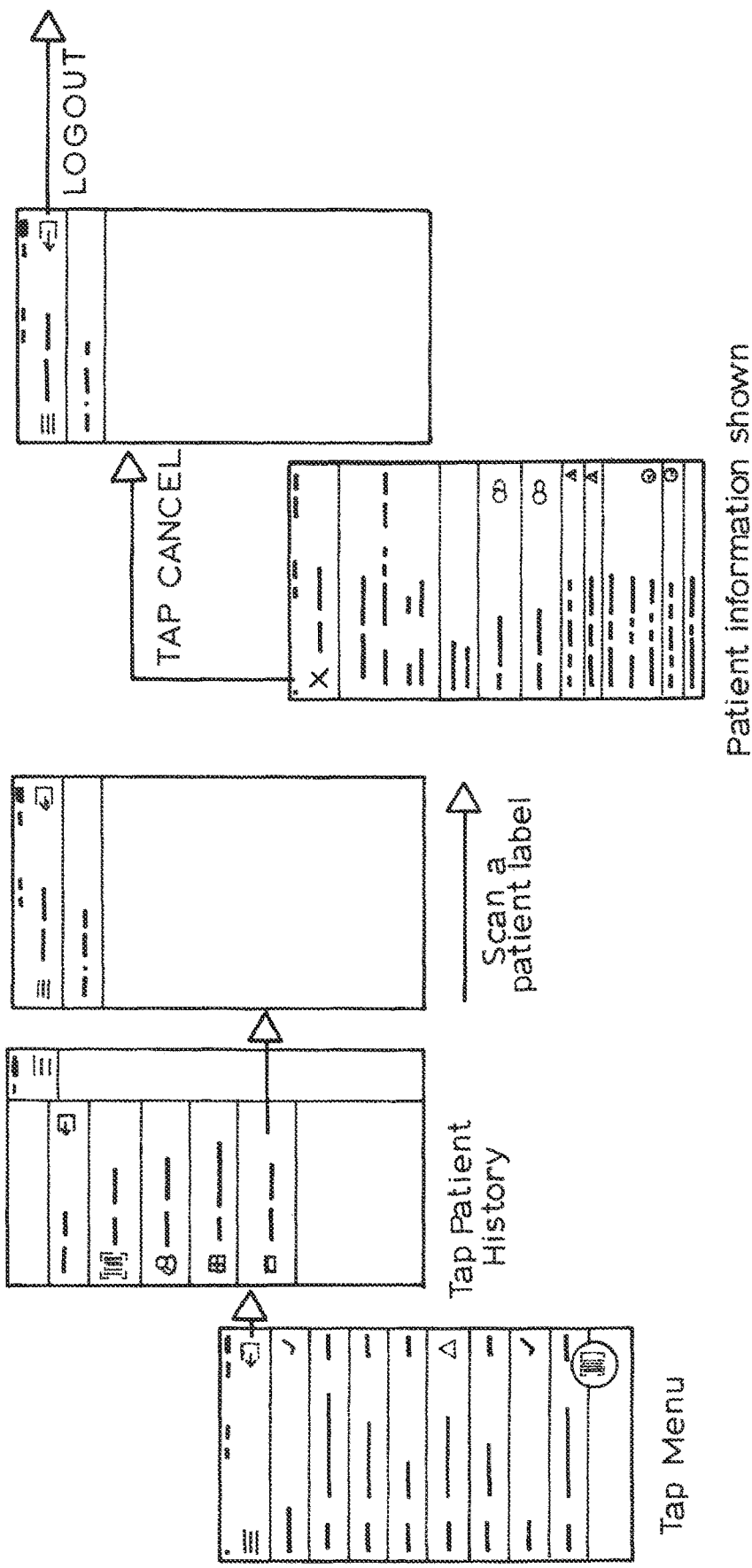
FIG. 30 shows, from the aspect of a user interface, an exemplary series of screen displays within a patient history review process illustrating an expedited session in accordance with a preferred embodiment.
Figure 31:
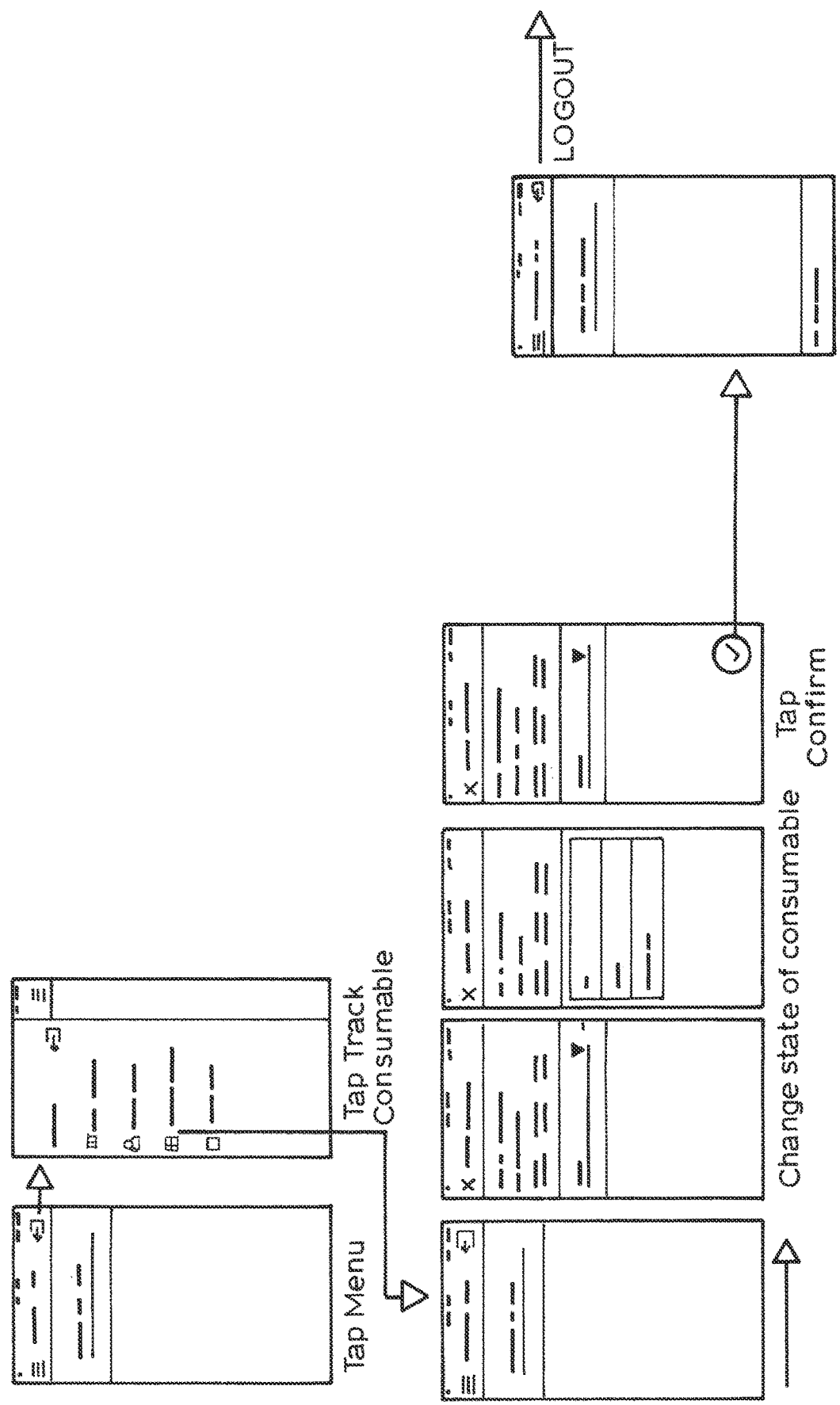
FIG. 31 shows, from the aspect of a user interface, an exemplary series of screen displays of process steps expediting the alteration of the status of a consumables lot in accordance with a preferred embodiment.

FIGS. 29 to 31 show a number of common use procedures that may be employed in accordance with preferred embodiments, namely, Scan Session, Review Patient History, and Activate Consumable Lot. With respect to the flow chart of display screens in FIG. 29 an expedited process for completing a scan session is shown. FIG. 30 illustrates an expedient mechanism for the procedure of reviewing patient history. The patient history feature allows the user to review the past five scan sessions for a patient and manually change the cycle status via scanning any patient label. FIG. 31 shows the steps for a quick change of status of a consumable lot or batch that is expanded from the menu, which can be invoked from a scan of the consumable label, changing the status and tapping to confirm before logging out.

Figure 32:
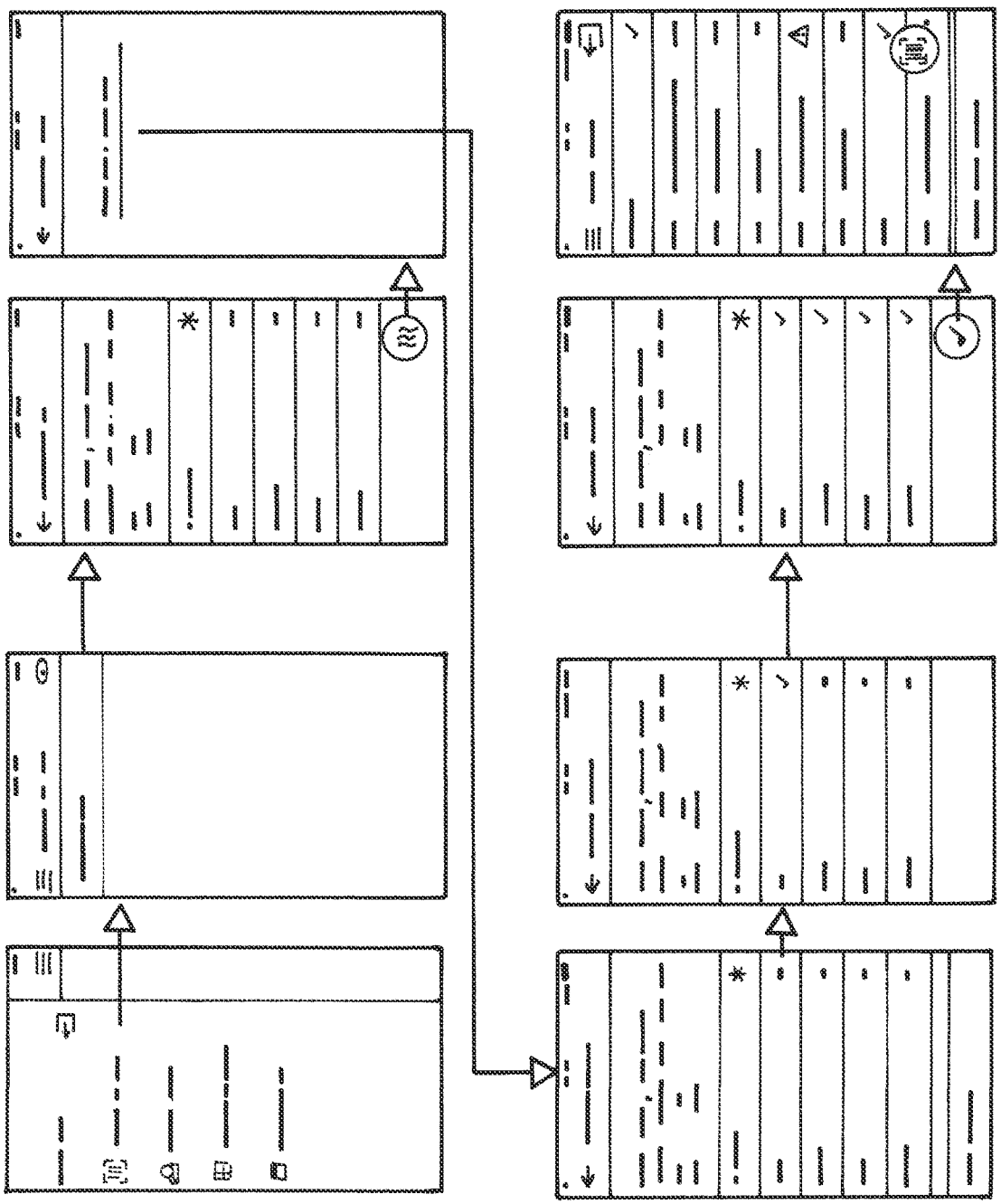
FIG. 32 shows, from the aspect of a user interface, an exemplary menu and screen displays for a user completing a scan session for retrieval and removal of a biological sample from a $LN_2$ environment in accordance with a preferred embodiment.

FIG. 32 illustrates a scan session and the operation of removal of an embryo once located in its storage point. Firstly, a scan session is started as normal. A patient file label is scanned. If the patient embryo's are in storage, the 'review patient' screen is displayed. The user confirms to remove embryo by tapping a "thaw" or equivalent 'remove' button. The user is then prompted to link their handheld device 6 to a reader by scanning a label on the reader. A pop-up message confirms connection. The location of a cassette with reader begins (away from the handheld). The status of progress may be presented on the handheld device 6. Once the location has been fully confirmed, the button to confirm removal appears. The handset display returns to home (Active List screen), a pop up confirms cassette removal. Sample Storage in $LN_2$ for Vitrification/Cryopreservation and Sample Thawing As noted above the devices 6 of FIG. 1 may have additional functionality which comprises any one of, or a combination of:

Bluetooth, WiFi (or other) connectivity for linking to:
  sensors for embryo critical items (such as environmental monitoring, for example, temperature; humidity, volatile organic compounds (VOCs) and $CO_2$); and
  Bluetooth LE (low energy) beacons; and
other position location capability, such as by a global positioning capability (GPS, Glonass, Galileo) or local positioning system (LPS).

Furthermore, as noted above, preferred forms for the sensors include the "Bluechiip" MEMS (micro-electromechanical systems) sensors of Bluechiip Ltd. Such MEMS sensors preferably include temperature sensing functionality and are preferably embedded in disposables such as:

vitrification/cryopreservation storage vessel/devices containing the sperm, embryo, eggs or gametes during the process of vitrification/cryopreservation and subsequent storage;
cassettes and other holders for the vitrification/cryopreservation devices; and Canes, canisters and dewars for storing vitrification devices
culture dishes for embryos/eggs and gametes.

Accordingly embodiments of the invention provide for an automated vitrification process. In a particularly preferred embodiment that utilises the "Bluechiip" MEMS (microelectromechanical systems) sensors of Bluechiip Ltd, a procedure is as follows. In accordance with embodiments described above, each step in the automated vitrification process involving labels and activities is defined. At stages in the process the system may use either a visual barcode/photo or a Bluechiip to identify the patient and store the information. References to the term 'sled' may be taken as the equivalent of the hand held device(s) 6 described above and herein.

With reference to FIGS. 33 to 47, devices utilised in the automated vitrification process involving any particular biological sample being processed may comprise the following as would be appreciated by the person skilled in the art: Sled 6 and mems reader 360; Bluechiip sensor(s) in the Cassette 380 and a barcode on the label of a Cassette 380. A Bluechiip device and a barcode on the Cane 441. A Bluechiip device is on the Canister 370. A Bluechiip device is on the Tank 350. A Bluechiip device or barcode on the Pod. A Bluechiip device or barcode on the Straw/cane or other vitrification devices such as the Cryotop. This device/s for Vitrification set up would need to: Read the Bluechiip ID or Read a barcode; communicate with the Electronic Medical Record (EMR) management system; Eg. Communicate with the Sled 6; be able to read the Bluechiip device(s) in the canisters 370 and the Cassette 3680. Either read the barcode or Bluechiip device of the pod, straw, or other vitrification devices such as a cryotop.

With respect to selection and thawing/warming of samples, devices used may comprise as would be appreciated by the person skilled in the art: Sled and MEMS reader; Bluechiip device in the Cassette; A barcode is on the label of the Cassette; Bluechiip and barcode is on the Cane; Bluechip is on the Canister; Bluechiip device is on the Tank; Bluechiip or barcode label is on Pod; A barcode is on the label of the Pod; Bluechiip or barcode label Straw and other vitrification devices such as Cryotop; This device/s for Embryo selection & Warming will: Read the Bluechiip ID and/or Read a barcode; Communicate with the Electronic Medical Record (EMR) management system; Eg. Communicate with the Sled; be able to read the Bluechiip device in the canister and cassette in the vertical plane in the storage system; Read the Bluechiip device on the Cassette and read the Bluechiip device or barcode label on the Pod in the horizontal plane within the Working station; Read the Bluechiip device or the a barcode of the Straw/Cryotop in the vertical plane within a LN2 transfer bucket; The device is required to read the barcode under LN2 and vapour conditions in the Working station prior to warming the pod;

An exemplary Automated Vitrification Steps (procedures) are as follows:
1. Label and fill 2× Vitbase™ dishes
   Read Dish barcode/label
   communicate to the central computer 2 of the system.
2. Switch automated vitrification instrument on.
3. Select protocol
4. Load operating tray
   Identify the media used in protocol.
   communicate to the central computer 2 of the system.
5. Load cassette and pods
6. Label Cassette and pods
   Read Cassette Bluechiip & barcode Pod barcode/label
   communicate to the central computer 2 of the system
7. Retrieve embryo dish from incubation instrument.
8. Place incubation dish under microscope remove lid
   Confirm patient match with dish barcode/label
   communicate to central computer 2 of the system.
9. Load the embryo onto the pods
   Confirm patient match with dish barcode/label with pod barcode/bluechiip
   Read the cassette, pod and the patient dish
   communicate to the central computer 2 of the system.
10. Load Cassette into automated vitrification Instrument.
11. Start automated vitrification protocol.
12. Automated vitrification protocol processing.
13. Alarm sounds, open door and grasp cassette with tweezers.
14. Immediately dunk the cassette into the $LN_2$ bucket.
15. Remove $LN_2$ bucket from automated vitrification Instrument.
16. Transfer $LN_2$ bucket to the storage area.
17. Transfer the Cassette to the storage device, double witness location.
   Confirm patient Scan Cassette
   Scan tank
   Scancanister
   communicate to the central computer 2 of the system.
18. Confirm run has finished.
19. Remove operating tray. Dispose of consumables.

An exemplary Embryo Selection & Warming protocol—Steps are as follows:
1. Prepare and label embryo culture dishes
   Confirm patient match
   communicate to the central computer 2 of the system.
2. Label and prepare warming dish
   Confirm patient match
   Communicate to the central computer 2 of the system.
3. Prepare warming dishes and media
4. Retrieve Cassette from storage device, double witness location.
   Confirm patient
   Scan tank
   Scan canister
   Scan cassette
   Confirm patient match
   Communicate to the central computer 2 of the system.
5. Take $LN_2$ transfer bucket containing cassette to the working station.
6. Place cassette in Working station vertically at side of stage.
7. Drag cassette onto stage in rear position.
8. Select pod and remove from cassette and place on magnetic holding position.
9. Double witness the Pod and the warming dishes.
   Confirm patient match-barcode
   communicate to the central computer 2 of the system.
10. Thaw embryo as per Gavi Thawing procedure
11. Thaw embryo transferred from warming dish to culture dish
   Confirm patient match-barcode
   communicate to the central computer 2 of the system.
12. Follow existing Lab protocols to continued culture and assessment of the embryo.
13. Repeat all steps for all remaining pods to be warmed.

Figure 33:
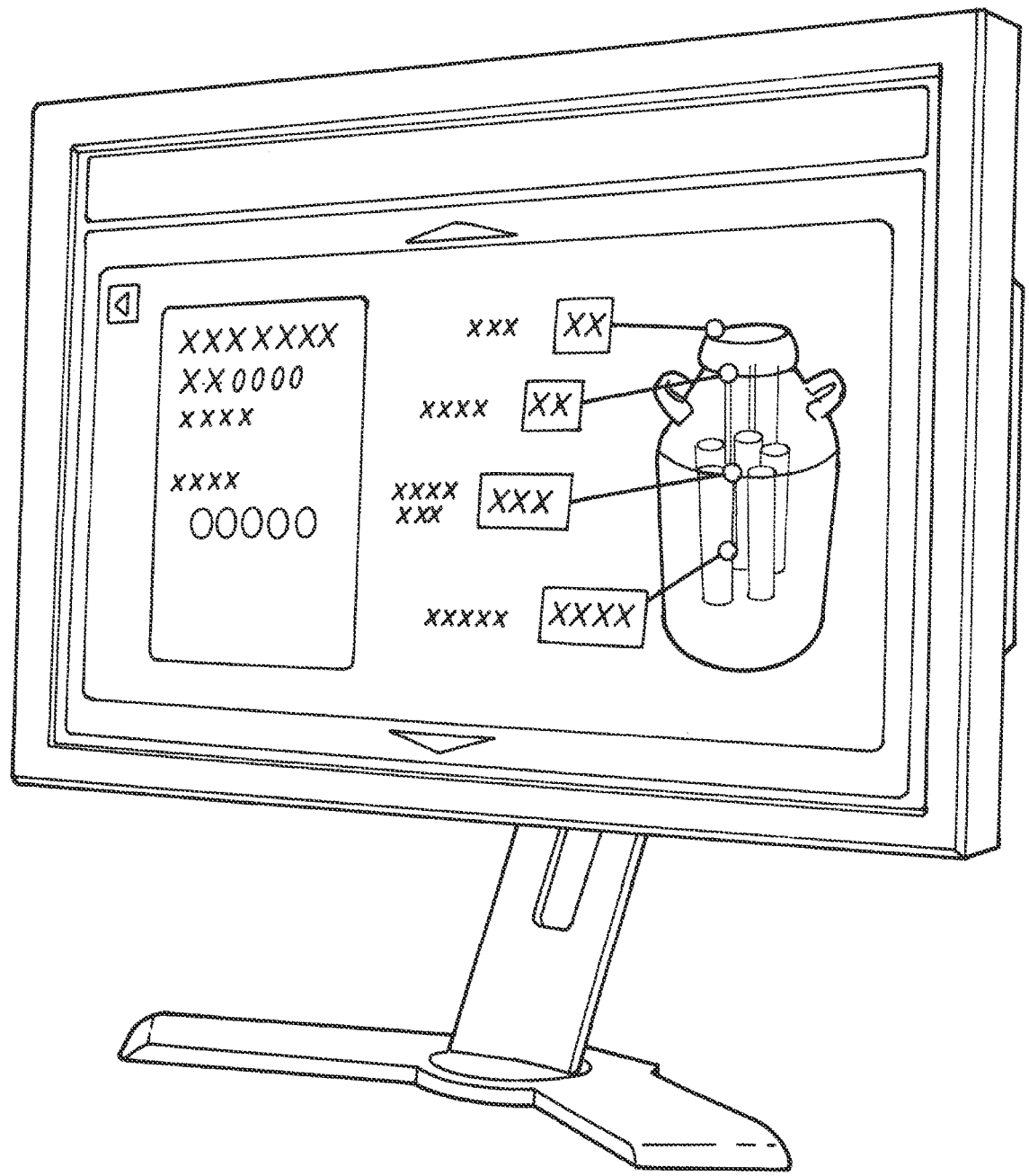
FIG. 33 illustrates a screen display resulting from a patient selection in a scan session which identifies the location of a given biological sample within a $LN_2$ environment in accordance with a preferred embodiment.
Figure 34:
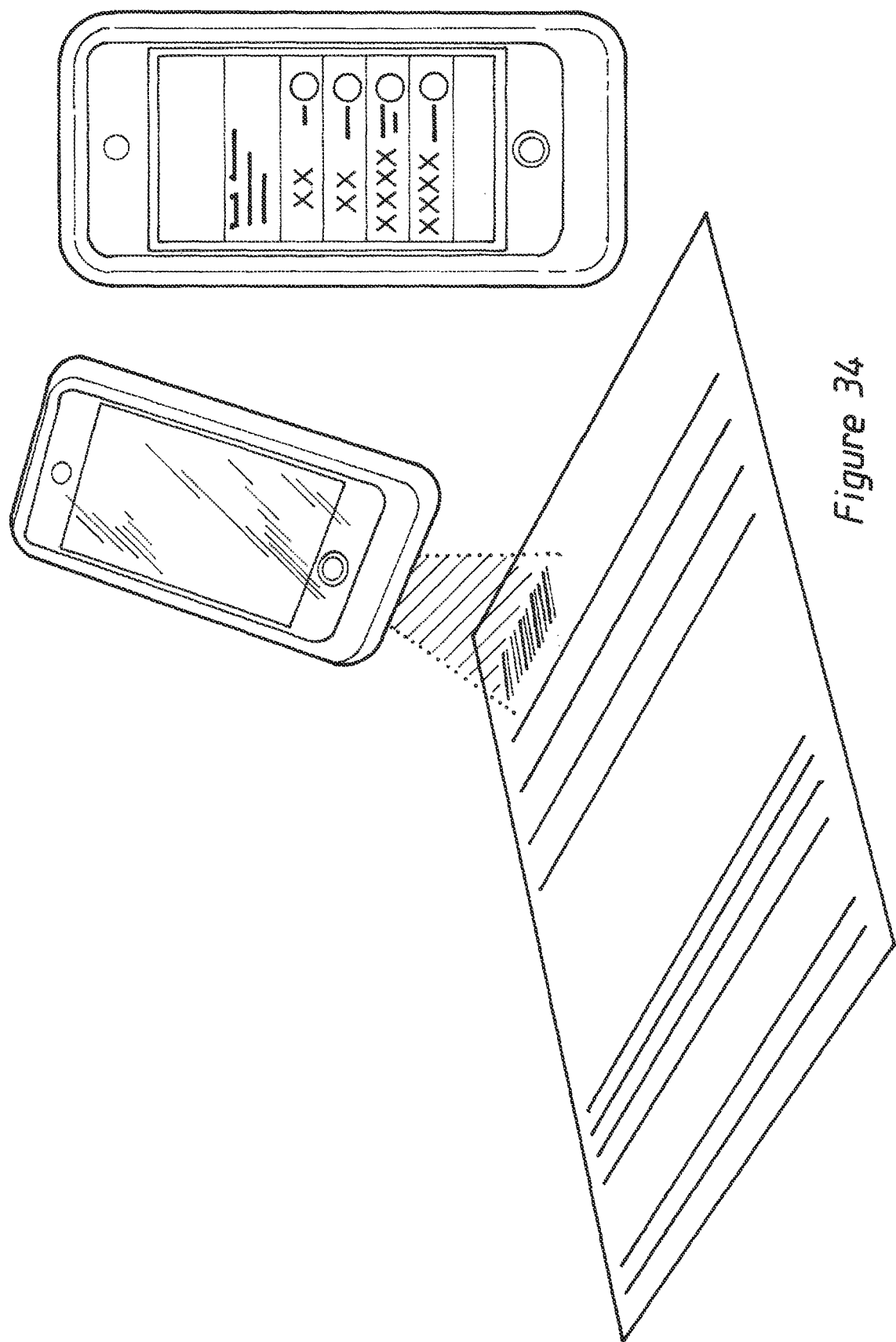
FIG. 34 illustrates the retrieval of patient information with the use of a hand held device in accordance with a preferred embodiment.

In accordance with a system workflow, the user will select the patient from the data base. Alternatively, the user may scan the barcode on a freeze sheet to bring up the patient on the database. Patient selection brings up another screen to show the details of the patient and the biological samples, as shown in FIG. 33. As shown by FIG. 34, start by scanning the Patient sheet with the Sled. This brings up a list of locations on the sled.

Figure 35:
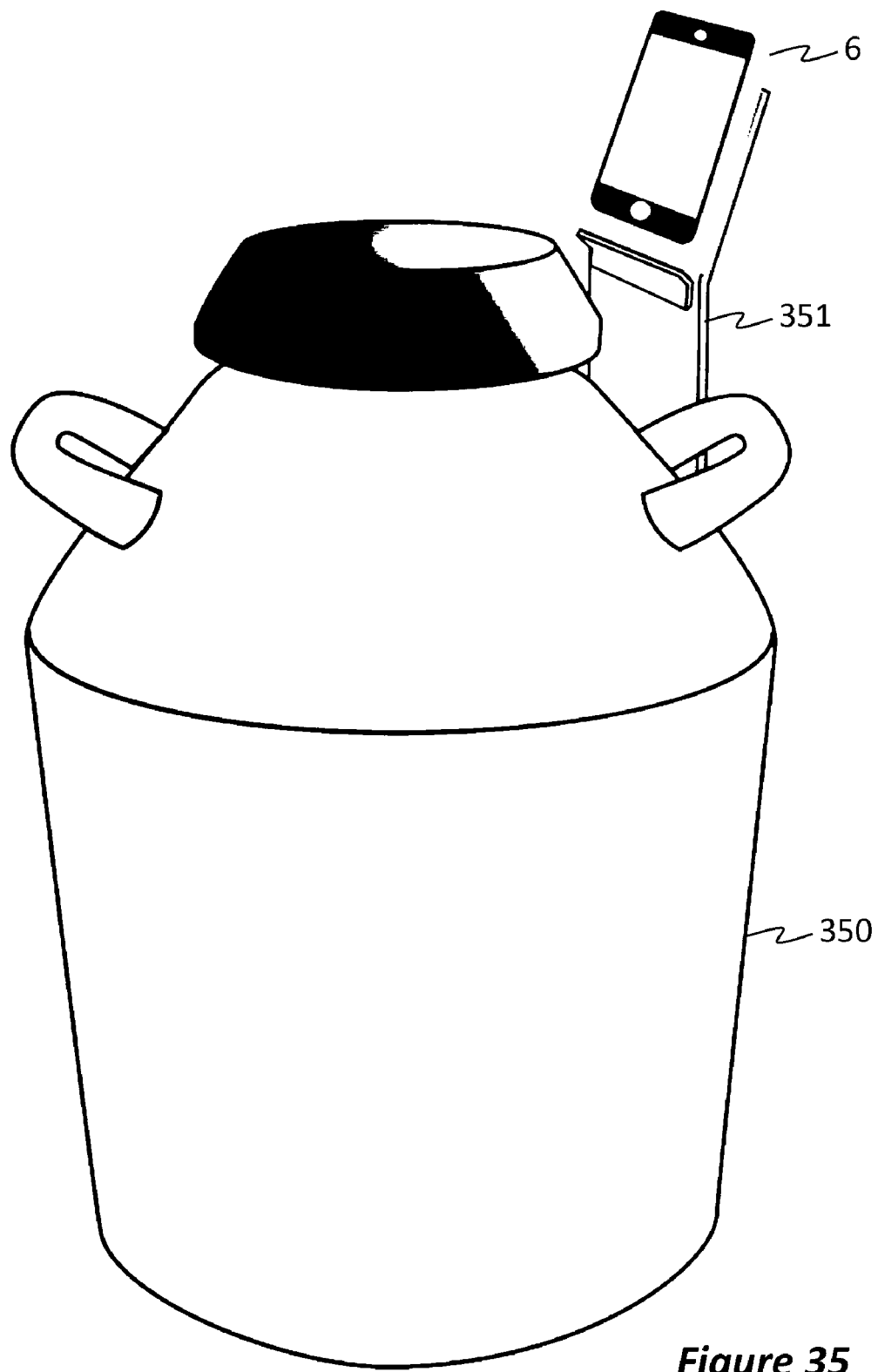
FIG. 35 illustrates an exemplary means for positioning or locating a hand held device in the course of a laboratory workflow in accordance with a preferred embodiment.
Figure 36:
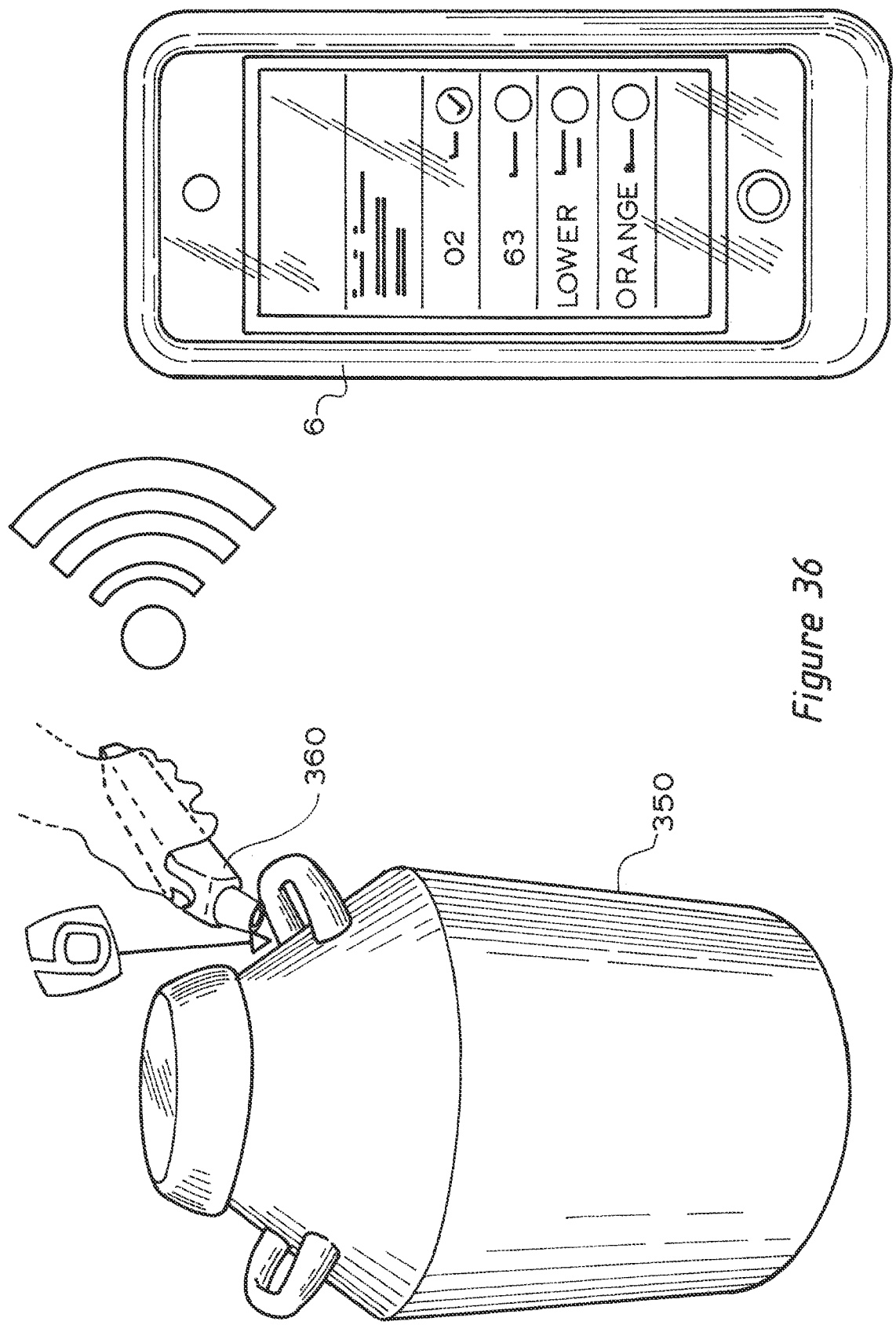
FIG. 36 illustrates a first step in indexing or addressing the location of a biological sample in a $LN_2$ environment in accordance with a preferred embodiment.
Figure 37:
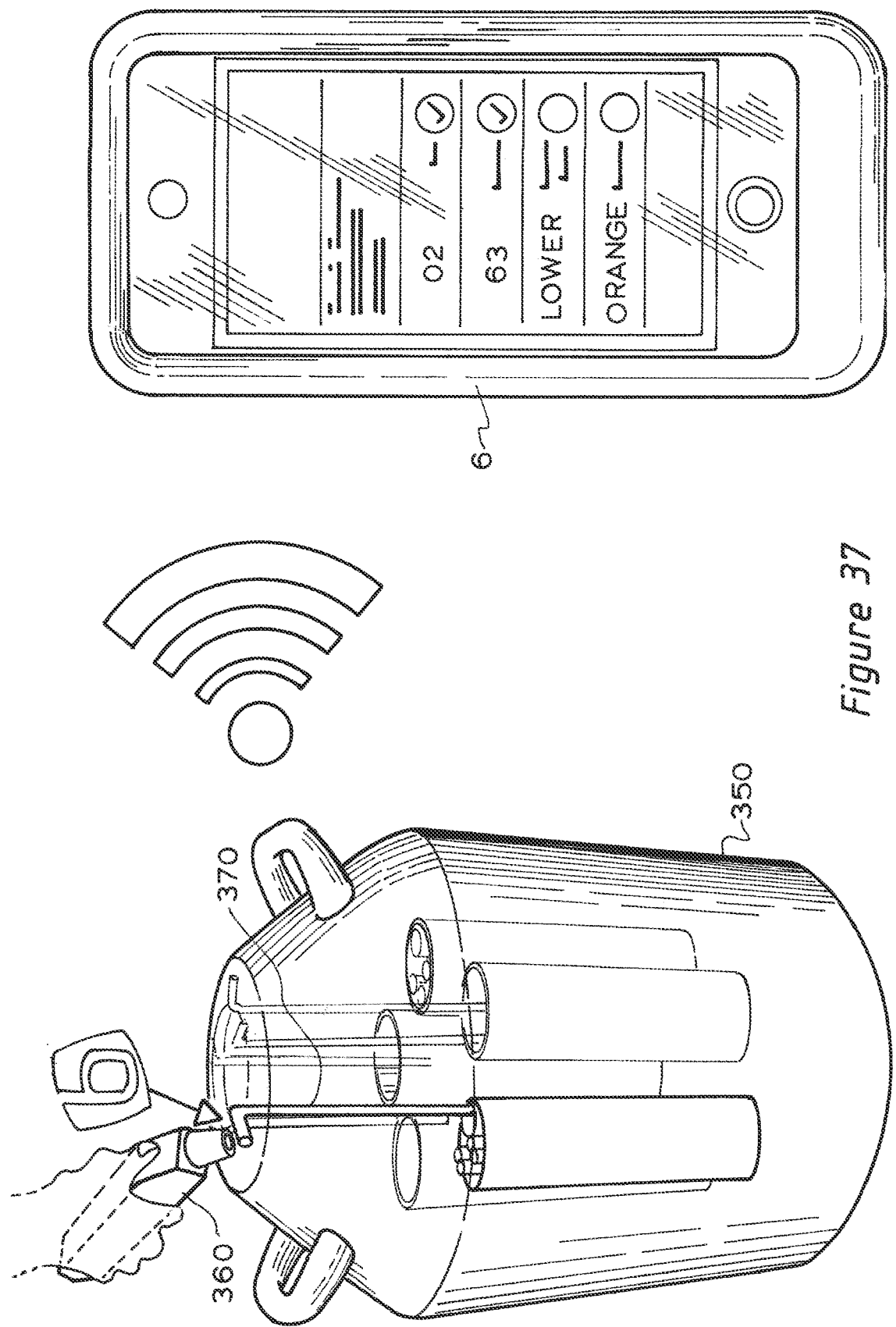
FIG. 37 illustrates a second step in indexing or addressing the location of a biological sample in a $LN_2$ environment in accordance with a preferred embodiment.
Figure 38:
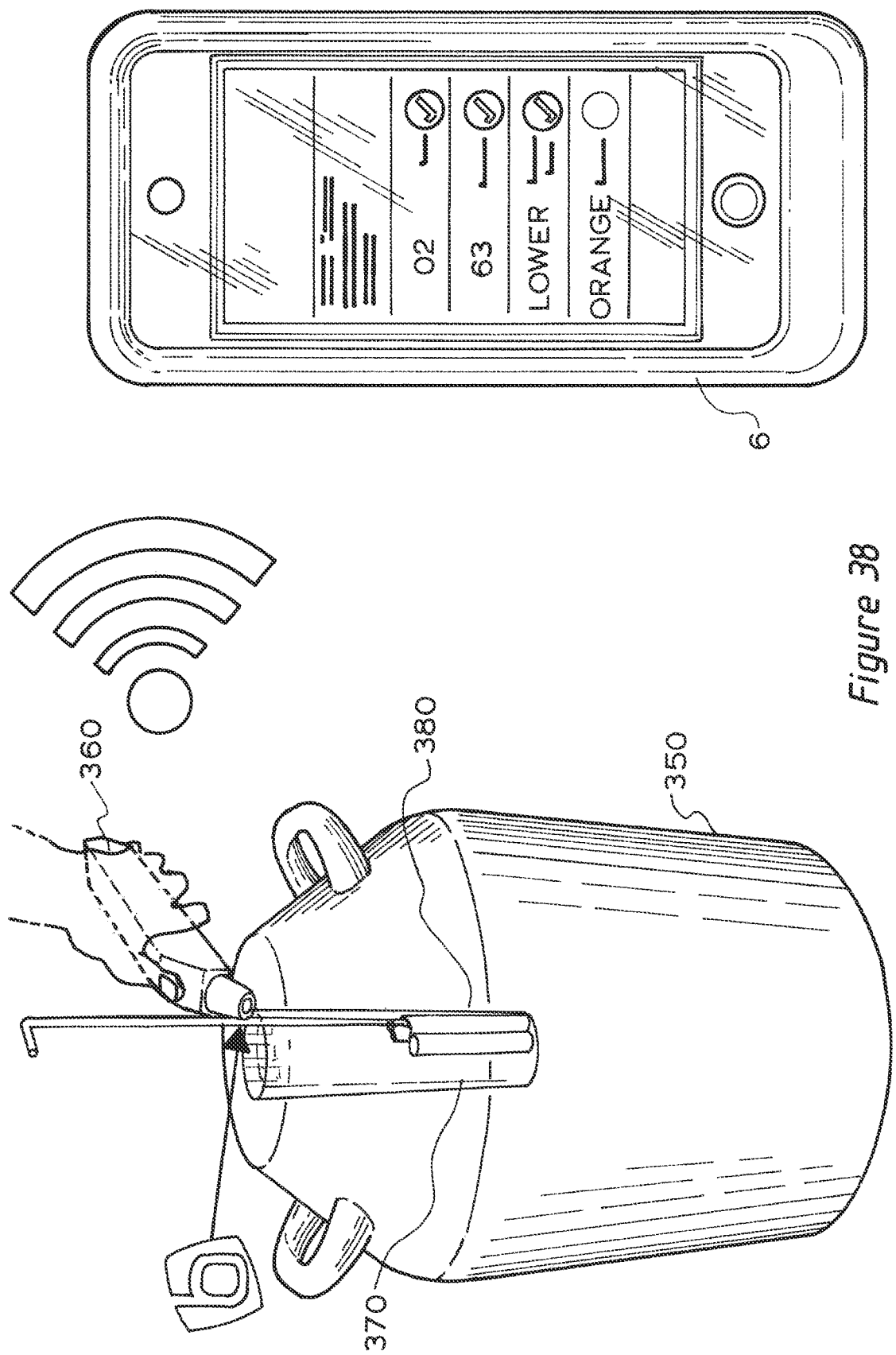
FIG. 38 illustrates a third step in indexing or addressing the location of a biological sample in a $LN_2$ environment in accordance with a preferred embodiment.

As illustrated in FIG. 35, the sled position could be placed on a magnetic stand 351 next to an opening of a Dewar tank 350. This keeps all the information close within user eye line and also keeps hands free; enables easier communication between Bluechiip reader and the Sled, and creates a common user experience and work flow across all storage locations, including different tanks i.e Vapour phase tanks. As shown in FIG. 36, it is possible to scan the tank Bluechiip tag with the Bluechiip reader, the location on the Sled will highlight correct. As shown in FIG. 37 the user scans the Canister Bluechiip tag with the Bluechiip reader, the location on the Sled will then highlight correct. As shown in FIG.

Figure 39:
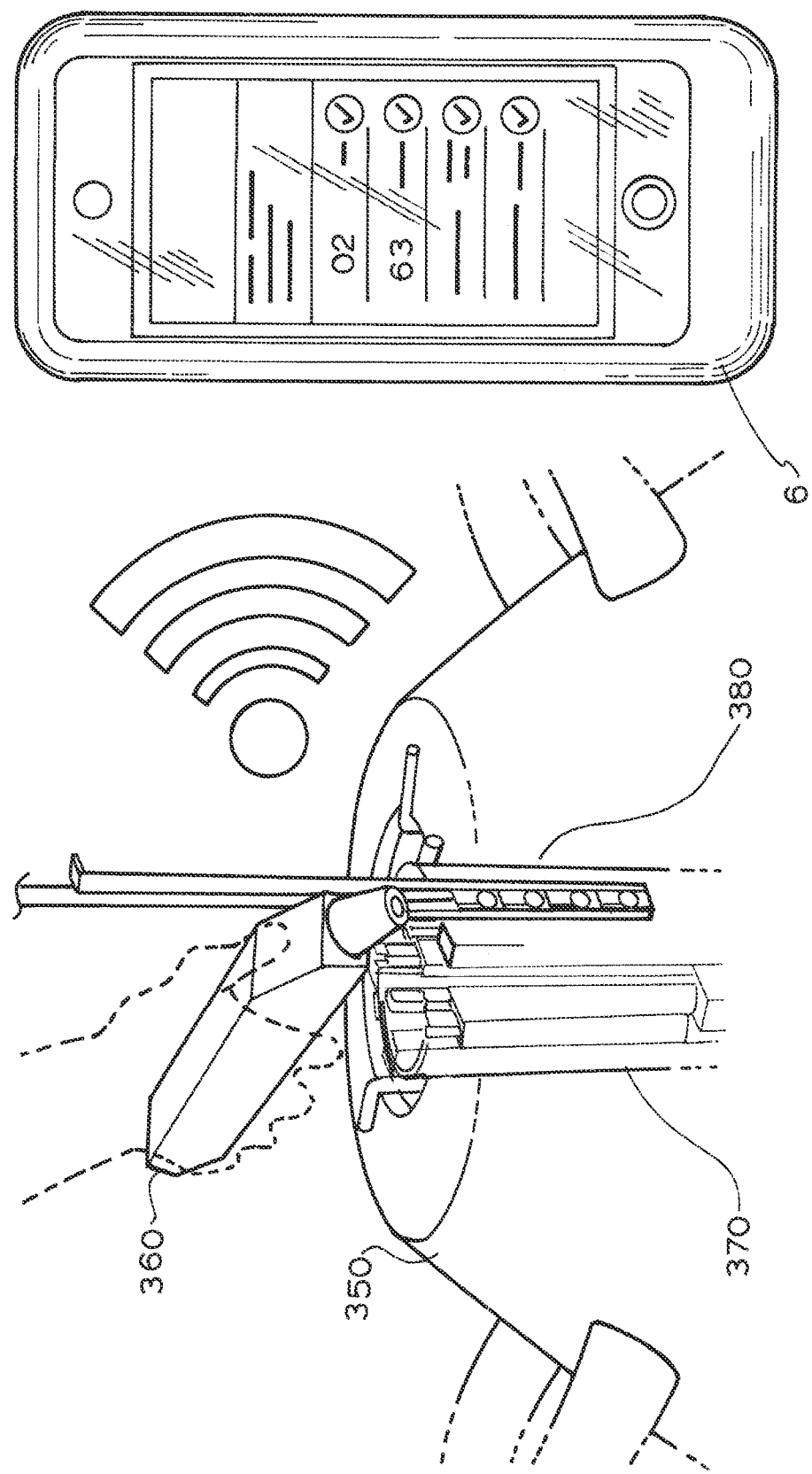
FIG. 39 illustrates a fourth step in indexing or addressing the location of a biological sample in a $LN_2$ environment in accordance with a preferred embodiment.
Figure 40:
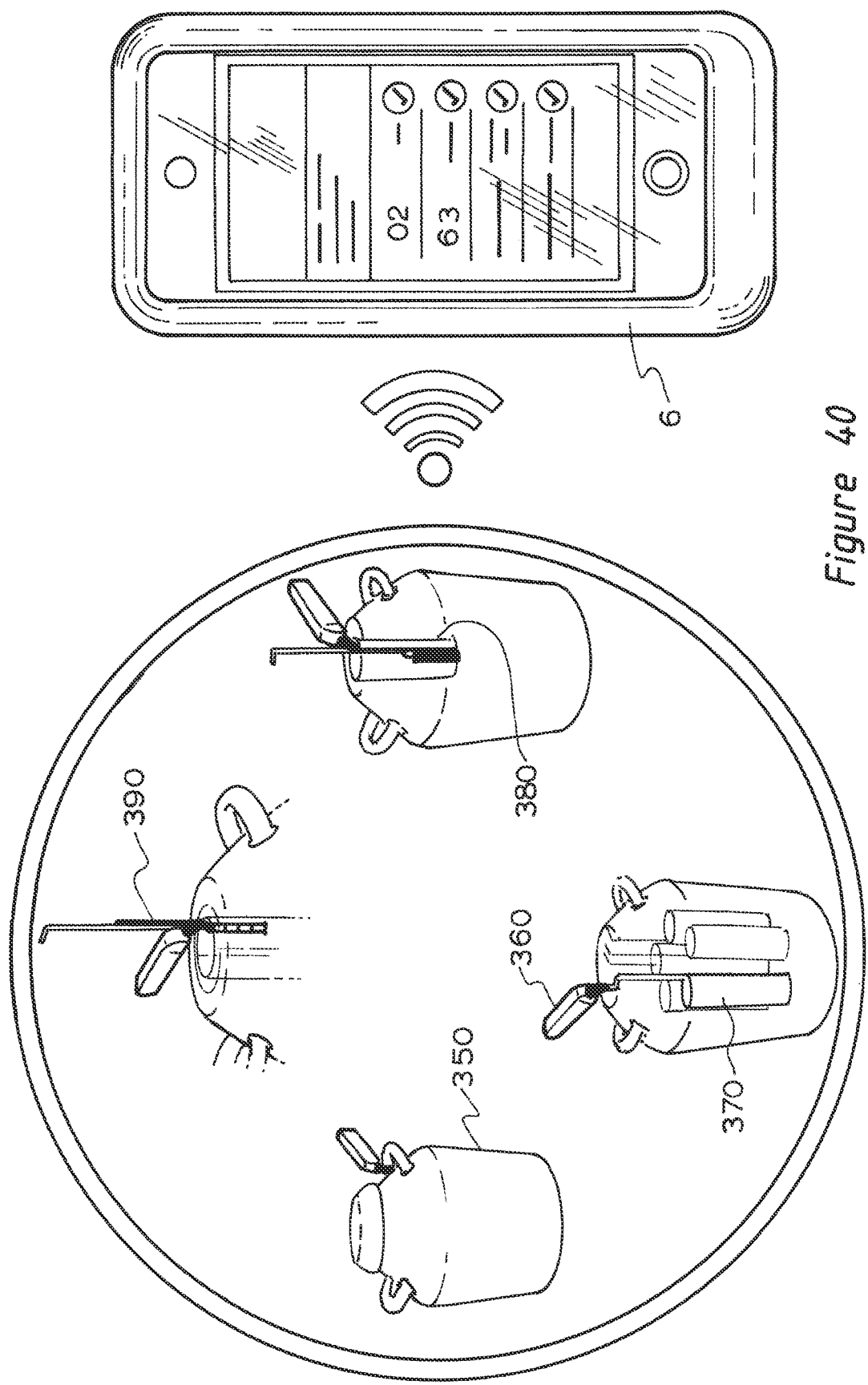
FIG. 40 is a schematic diagram of a system and process for storage of biological samples in a $LN_2$ environment in accordance with a preferred embodiment.

38, the user scans the Canister level Bluechiip tag with the Bluechiip reader, the location on the Sled will highlight correct. As shown in FIG. 39, the user scans the Cassette Bluechiip tag with the Bluechiip reader, the final check point will highlight correct. Then there is no mistake that the incorrect patient has been removed from the Storage system and exposed to ambient conditions. As shown in FIG. 40, the user may place a Patient Cassette into storage, simply scan all 4 of the Bluechiip devices in any order and store the information.

Other advantageous features available in preferred embodiments in regards to $LN_2$ tracking and the use of a Bluechiip device(s):

Ability to track and measure temperature of embryos and gametes under extreme conditions such as under liquid nitrogen temperature below −196° C.

Components of the reader comprise a mems reader and, a light which allows a user to view in the tank and, a locking mechanism which allows the user to read and pick up the patient sample at the same time. Indicator with light and noise to provide the user with a positive feedback when the correct samples has been located.

The problem of having all these valuable samples being stored in $LN_2$ tanks inter alia is managed presently using paper. Preferred embodiments of the present system overcomes this problem by having a centralised database which have the exact locations of all the samples at the patient and embryo/sample level. This is achieved by the samples being tagged using the Bluechiip technology every time it is moved in and out of the tank. As the $LN_2$ tank, the canisters, and cassette, and pods are all Bluechiip tagged or barcode tagged the location of the samples are always known.

Cassette Design

Figure 41A:
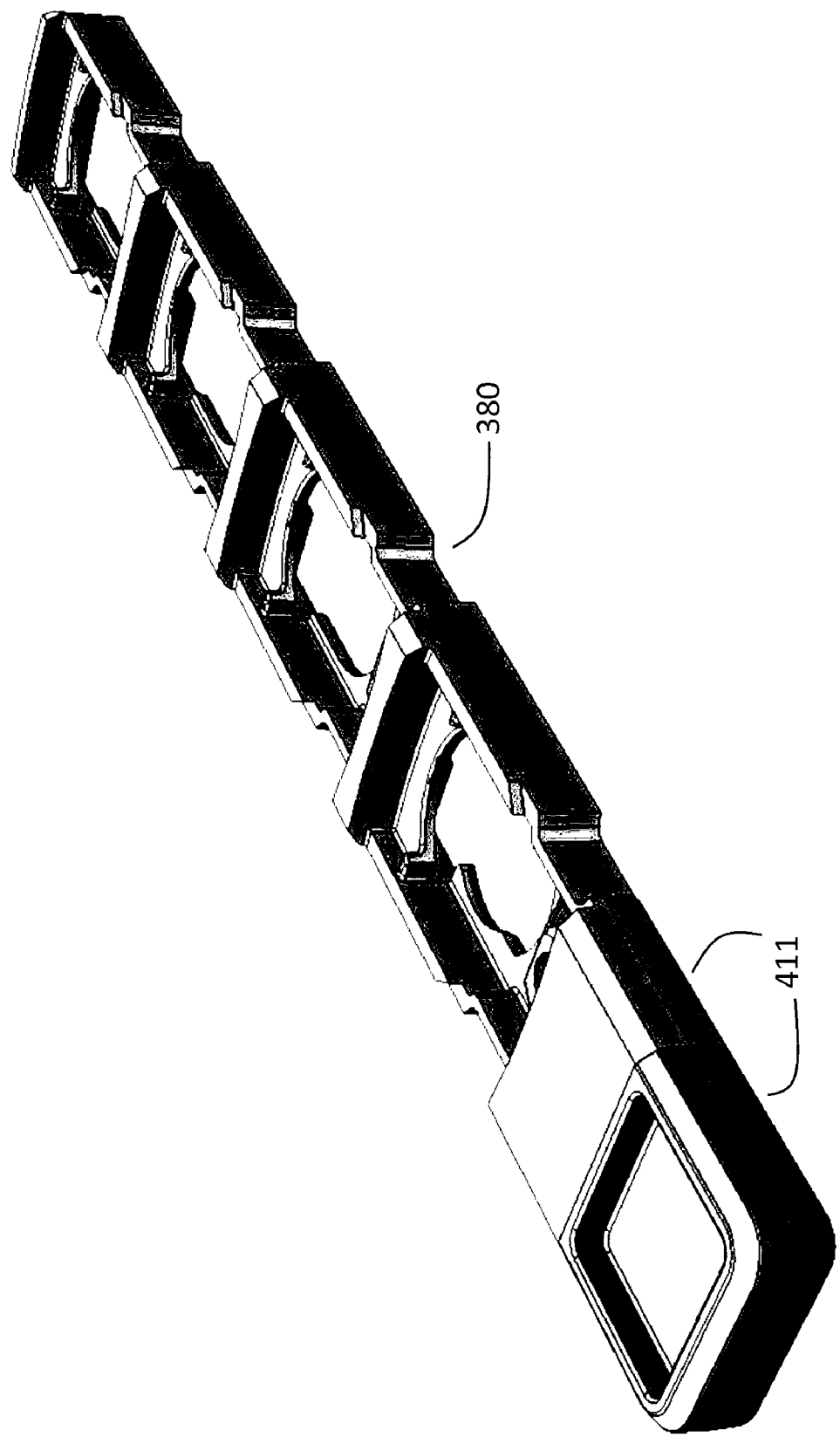
FIGS. 41a and 41b show a cassette incorporating a sample locating device in accordance with a preferred embodiment.
Figure 41B:
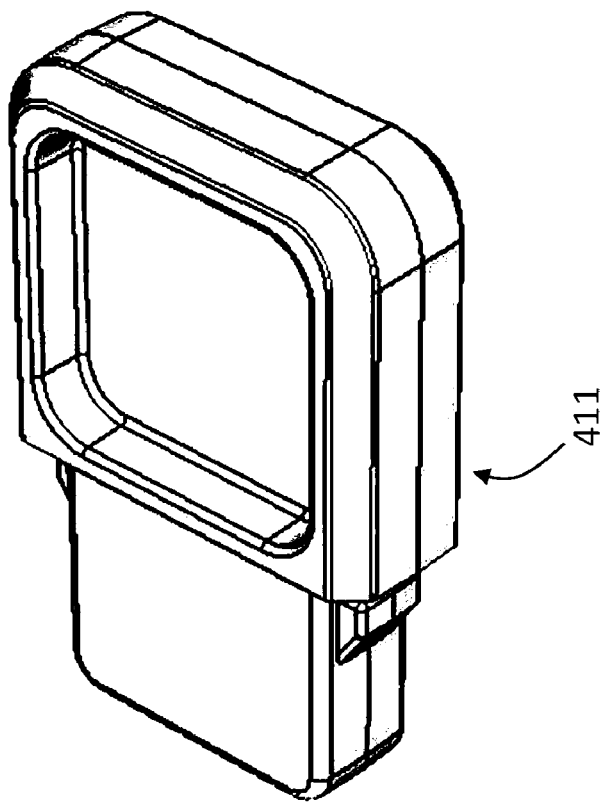
Figure 41B:
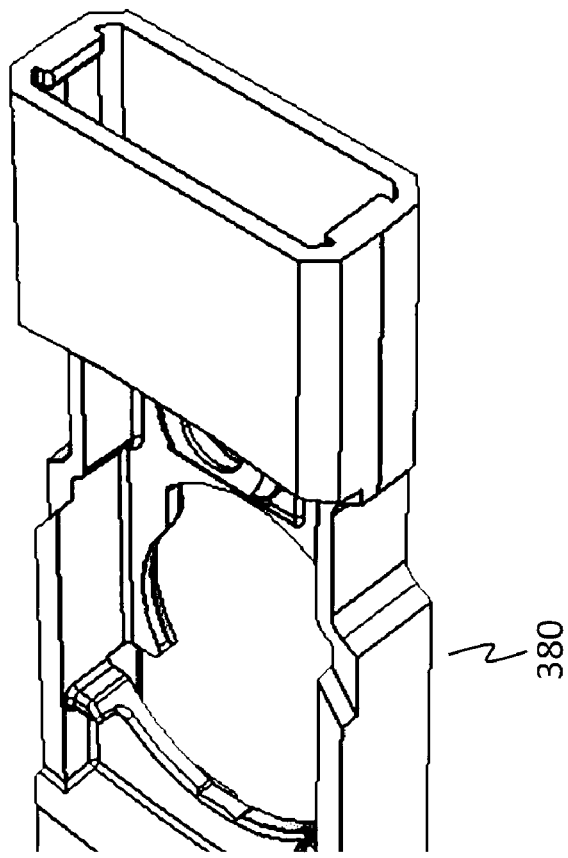
Figure 43:
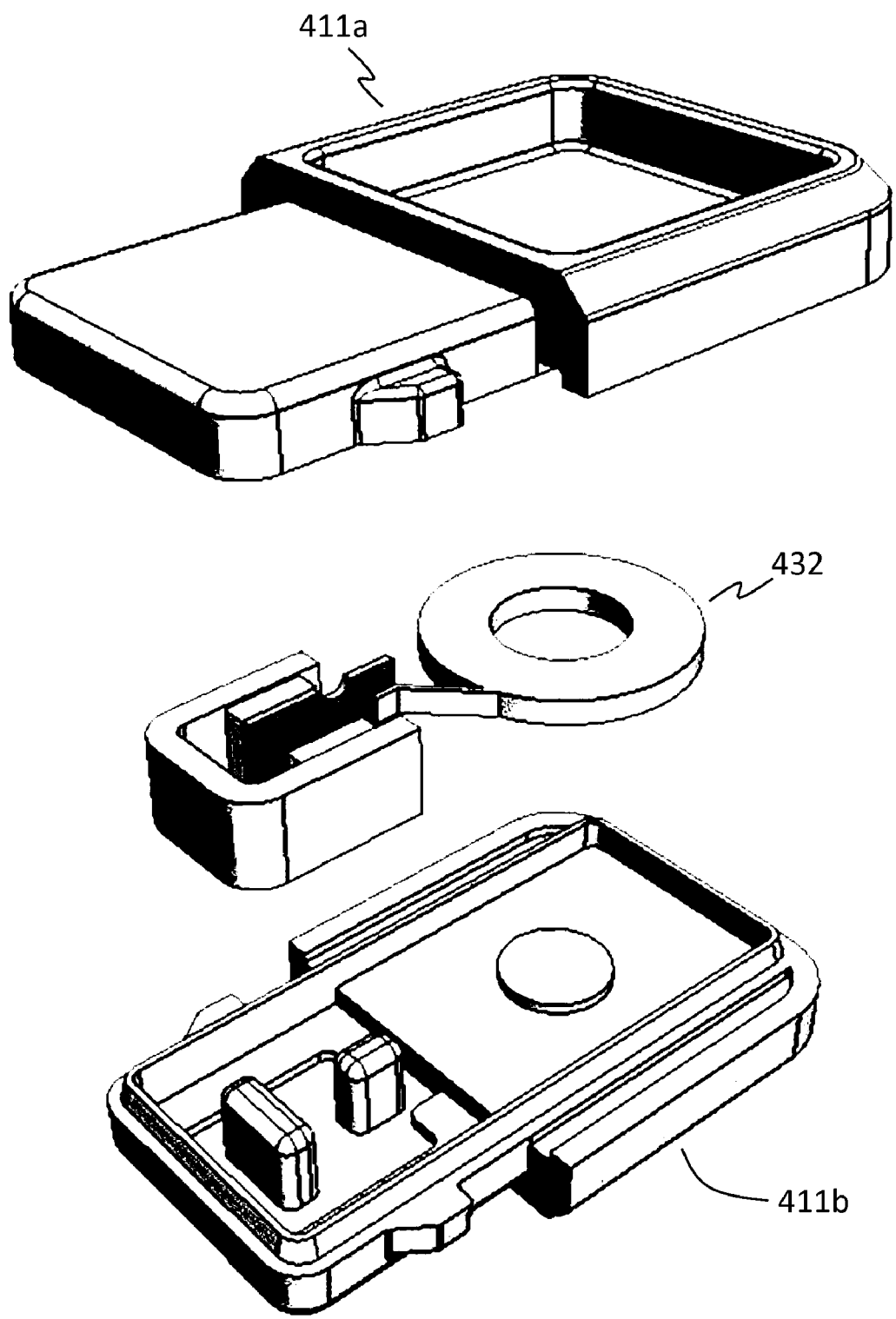
FIG. 43 shows an exploded view of the sample locating device of FIGS. 41a and 41b.
Figure 44:
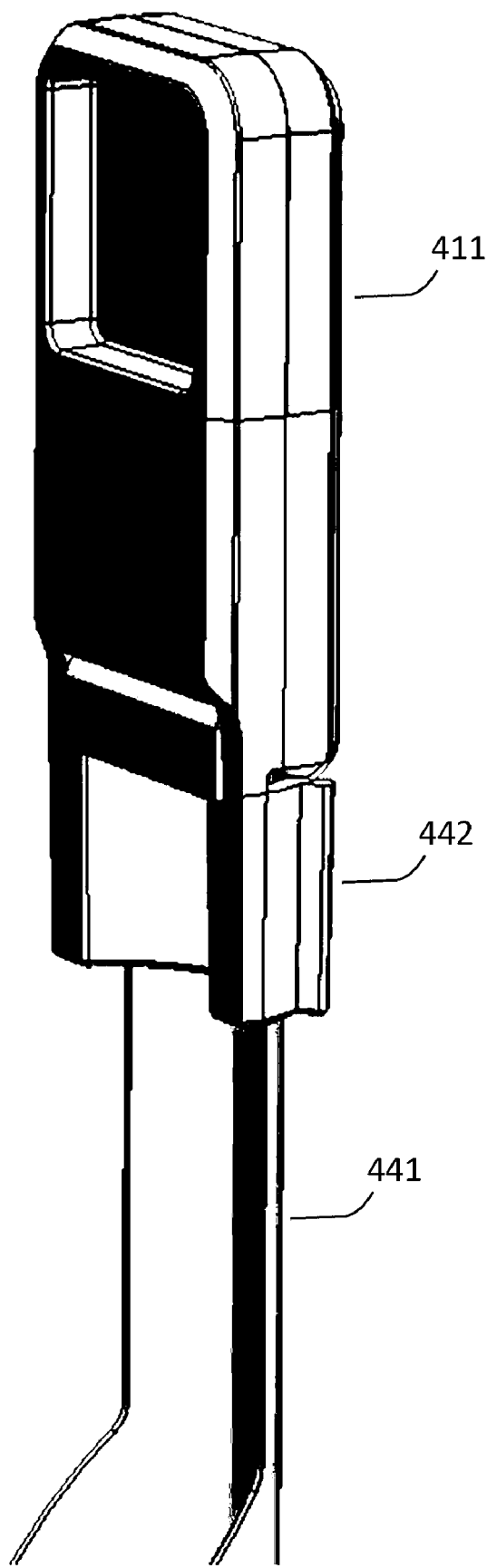
FIG. 44 shows an alternate embodiment of the sample locating device of FIGS. 41 and 43 positioned on a biological sample cane in accordance with another embodiment.
Figure 45:
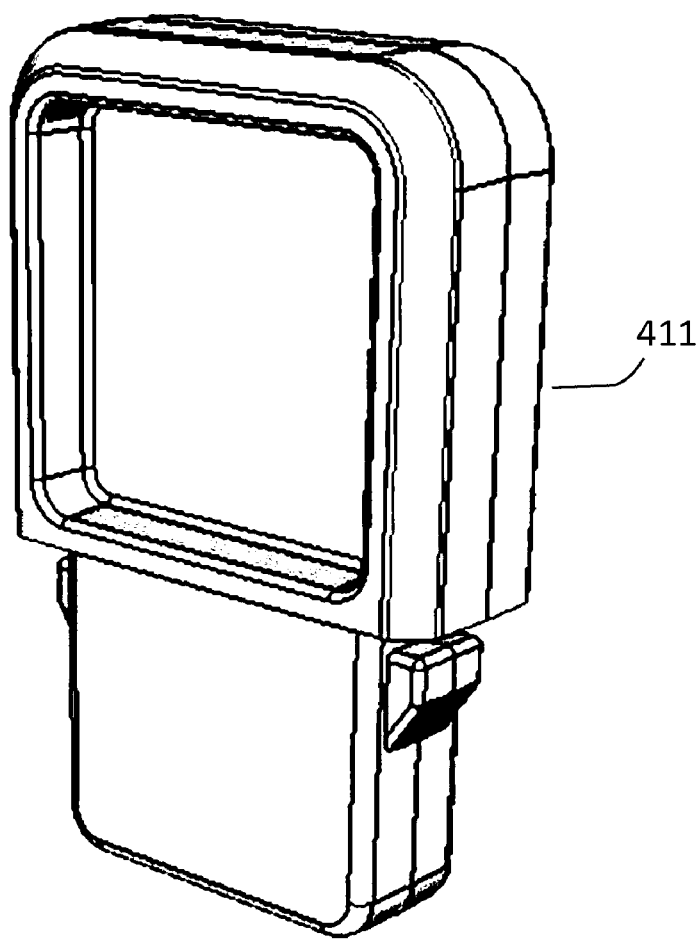
FIG. 45 shows another embodiment in which the sample locating device of FIGS. 41 and 43 may be fastened to laboratory apparatus.
Figure 45:
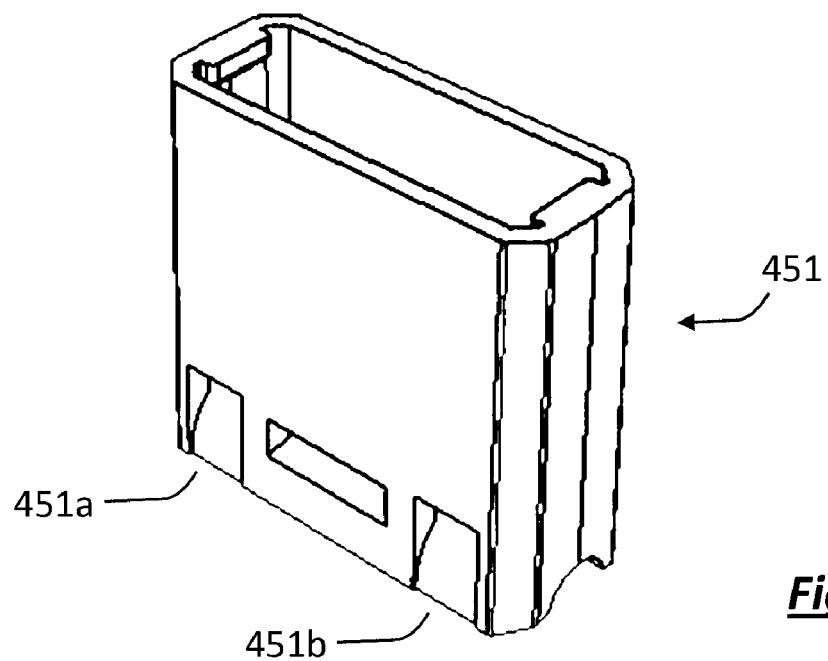

With respect to sensing in a cassette, a Bluechiip device may be integrated with the cassette through the design of a small assembly 411 that clips (one way) into the end of the cassette as shown in FIGS. 41*a* and 41*b*. With reference to FIG. 42, labels 421 may be applied to cassettes, for example, a 10 W×35 L mm label can be wrapped around the cassette label area where a full perimeter is 40 mm. As shown in FIG. 43, a Bluechiip tag may be incorporated using the internals of the active cylindrical Bluechiip tag 411 (magnets, yoke, and pcba) soldered to a 10 mm×1 mm flat coil 432 a new custom Bluechiip tag which can be created to integrate with the laboratory system instruments for biological sample treatment. In one example of preferred instrumentation the integration may involve 2 custom plastic housings 411*a* and 411*b* ultrasonically welded together and assembly features moulded into the lower housing. As shown in FIG. 44, the Bluechiip tag could be integrated with a Cane 441 through slight customisation of the cane top, and adding a plastic intermediate component 442. As shown in FIG. 45, an intermediate moulding 451 may be used to clip the Bluechiip tag 441 to the tank 350. This intermediate moulding has holes 451*a* and 451*b*, for zip ties 471 as shown in situ in FIG. 47.

Figure 46:
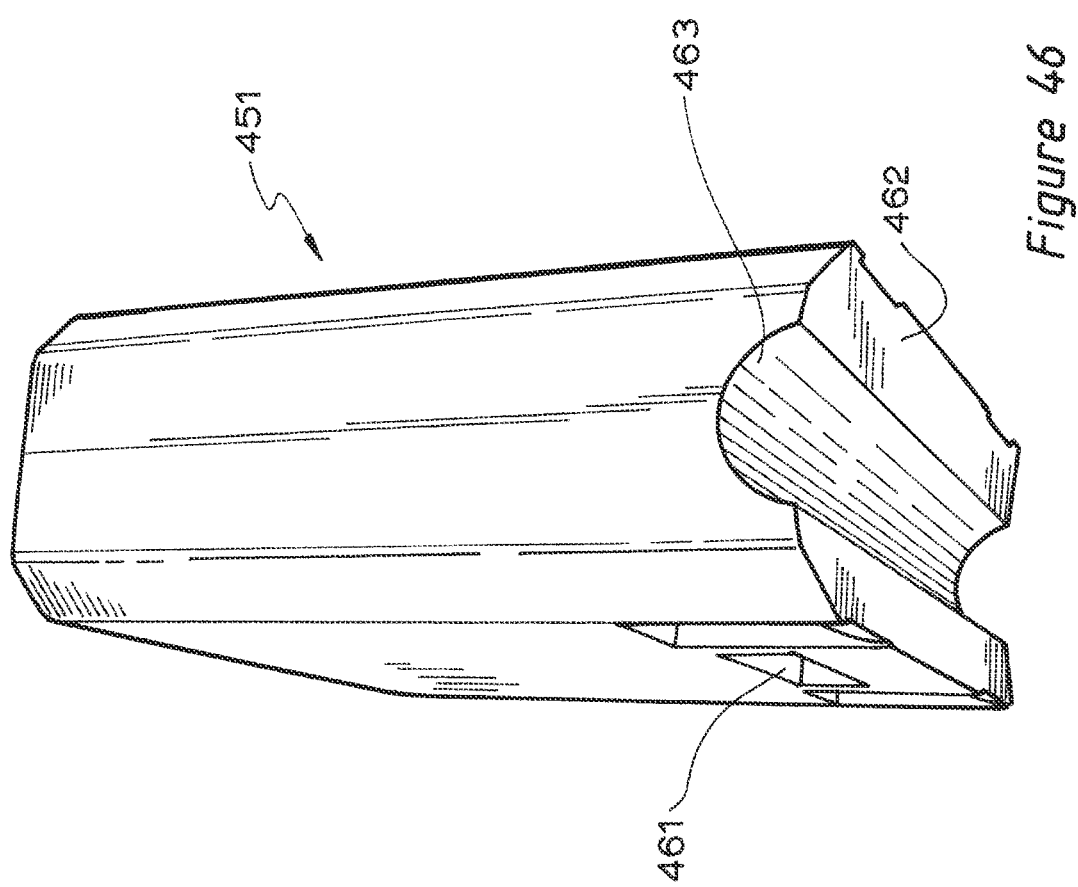
FIG. 46 shows an exemplary moulding for fastening the sample locating device of FIGS. 41 and 43 to laboratory apparatus in accordance with a preferred embodiment.
Figure 47:
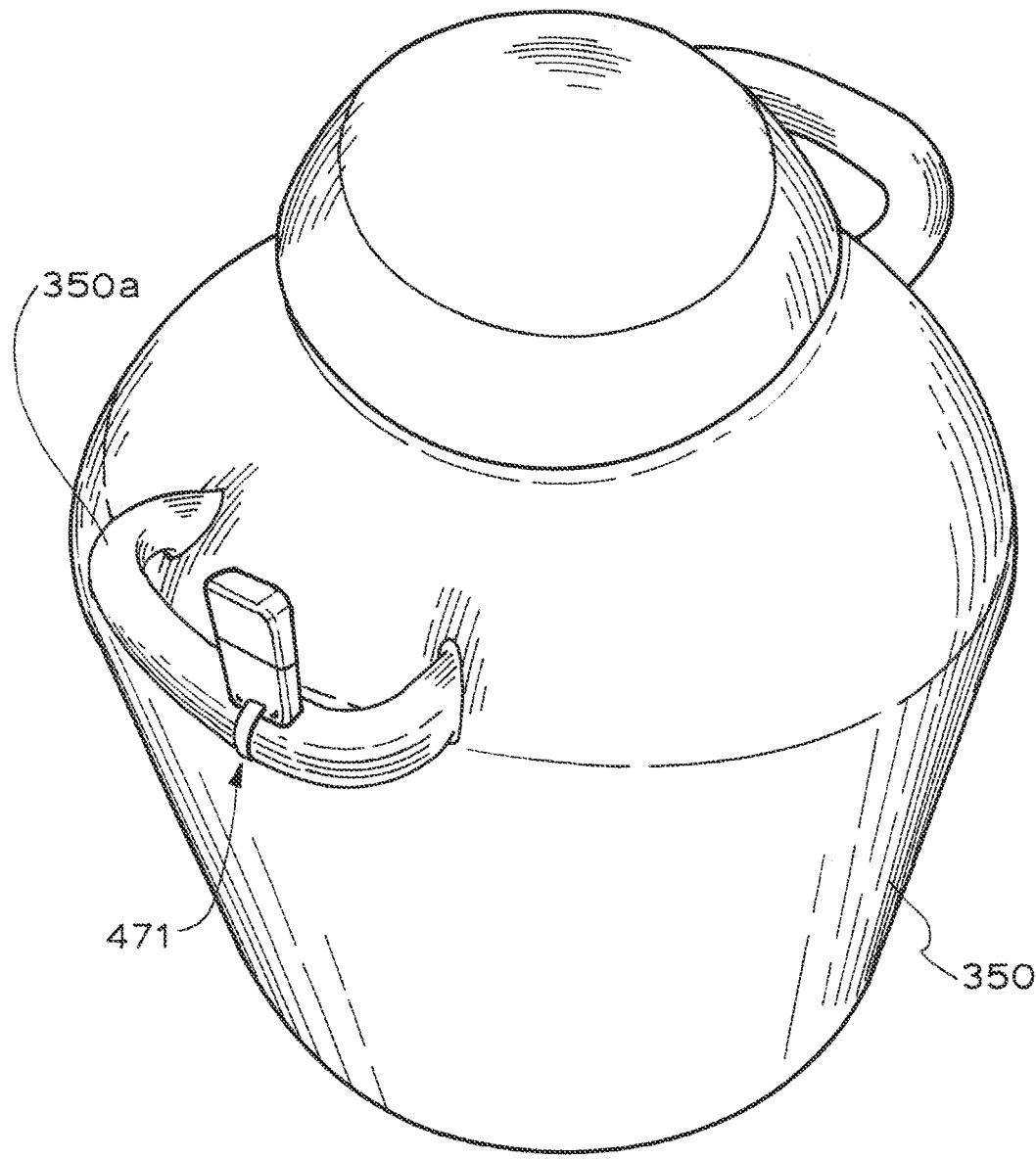
FIG. 47 shows an exemplary fastening of the sample locating device of FIGS. 41 and 43 to laboratory apparatus in accordance with a preferred embodiment.

With reference to FIG. 46 universal connection to a tank such as a Dewar tank 350 is illustrated. An intermediate moulding 451 is designed with 2 different radii in the lower mounting face 462 and 463 to allow for mounting to large or small handles, i.e. 350*a* as shown in FIG. 47 of a tank or the canister. As shown in FIG. 47, the Bluechiip tag may be connected to the tank via a zip tie 350*a*.

In preferred embodiments, the system is broken into essentially 4 components, namely:

The handheld device
which may be a iphone/itouch which is connected to a cradle which has a barcode scanner, magnetic strip reader.

The handheld device will have an witnessing app

The handheld device connects wirelessly via wifi or Bluetooth and communicates with other appliances and devices The web-base application, which can be run on a pc.
being Web-based allows the user to setup, print labels, monitor progress, track samples, track inventory, connect to EMR (electronic medical records)

The large screen to display the process of each patient. Activities screen.

The server which connects these components.

From a functionality point of view the system comprises the following:

User management
Define labels
Define lab processes
Define activities
Consumable lot tracking and consumable management
EMR bi directional which allows the system to connect to Electronic medical records to be able to receive and send information
Tracking of workflow and rules
Logs and reporting
Cycle progress management Desktop (This allows user to see patient overview and dashboard.)
Handheld device matching
Handheld manual witnessing
Cycle progress management handheld (This allows the user to see the patient overview)

From a technology point of view it is important to note the following that is brought into fruition by preferred embodiments:

Concept of allowing the users to define the labels and allocate them into days of the sample developmental timeline
Concept of assigning rules to each day which will warn user if a particular label is not scan on the day
Define labels and in the definition having labels which could be one of many, i.e. in the event of a dish there is a label for the lid and dish, therefore both dish and lid needs to be scanned.
Concept where it is possible to manage the workflow and actions of Embryologist, and prevent errors and missed steps
Concept where it is possible to have the notion of time, that each process needs to be performed within a specific timeframe. That could be in days, or in the event of critical steps that could be predefined by the user. That is, where
System and Database which will monitor and prevent an un-trained person from performing the tasks, he or she has been correctly trained to perform the task.
System and Database which will monitor and to prevent the user from using consumables and media which are:
Incorrect media
Has expired
Correct revision etc.
A centralised activity display which allows embryologist/ supervisor to immediately observe the process of all patients and warning when errors occur Witnessing and Tracking in $LN_2$ using the bluechiip technology. Cryomanagement of samples and stocktake The Bluechiip™ technology will preferably be used for tracking embryos and gametes under extreme conditions such as under liquid nitrogen temperature below −196 degrees.

Components include:
  Reader which consist of mems reader, light which allows to view in the tank, locking mechanism which allows the user to read and pick up the patient at the same time
  Bluechiip mems adapted for the automated vitrification cassette and patient canes
  Bluechiip mems adapted for the automated vitrification pods and the samples straws or other similar cryo storage vessels (e.g. Cryotop).
  Bluechiip mems adapted for the canister
  Bluechiip mems adapted for the $LN_2$ tank (dewar)
Ability to track sperm, gametes and embryos under $LN_2$ and outside $LN_2$
Combination of Mems chip and Barcode to track samples
Mems identification allow user to track both the temperature of the sample to prevent damage and the sample identification
The $LN_2$ storage system consists of
  $LN_2$ tank which is called a dewar. A dewar has the capability of storing 100s to 1000s of patient samples.
  A canister which sits inside the dewar depending on the size of the dewar there could be 6 canisters up to 100 s of canisters per dewar
  A cassette or cane, a cassette or cane holds multiple embryos or gamete sample of the same patient. Most canisters can hold up to 10s patients.
  Pod or straws, each cassette can hold up to 4 pods. Each cane can hold up to 10 straws.
Each of the individual components as described above is tagged with an identifier. This identifier can either be bluechiip mems or barcode.
Software database which allows each sample to be tracked as it is tagged into the location
The reader when in contact with the mems tag will identified and present the temperature of the sample when it is in contact.
A centralised database which will have the exact location of all samples in the Dewar tank. Current system is all on manual record and databases and in multiple location which makes it extremely difficult to locate a patient sample.
Simple and faster software stock take system without needing to disrupt the samples. Current process a physical inspection of 10% of the patient samples.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rexx; SAS; Scheme; sed; Simula; Smalltalk; Snobol; SQL; Visual Basic; Visual C++; Linux and XML.) for use with various operating systems or operating environments. The source code may define and use various data structures and communication messages.

The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

We claim:

1. A method of tracing one or more biological samples at any location in an assisted reproductive technology (ART) laboratory environment in the course of performance of a task, the method comprising the steps of:
   locating an RF transceiving device proximate a biological sample container wherein the RF transceiving device is encased in polymer that is resistant to a range of laboratory conditions including one or more of a cryo-environment and gamma irradiation;
   interrogating the RF transceiving device with a portable reader device for identification signals unique to the biological sample; and
   tracking the location of the one or more biological samples based on the interrogation of the RF transceiving device and indexing the location in a centralised database;
   wherein the method is periodically applied to one or more biological samples during (i) a configuration process and (ii) a supervision process,
   the configuration process involving creating and editing labels for the one or more biological samples associated with a patient, creating label groups corresponding to ART treatment cycles, assigning labels to a development timeline in each treatment cycle, specifying critical labels and specifying critical activities to be undertaken in relation to the one or more samples;
   the supervising process involving management of an active task list for the patient including progress of the biological sample against the development timeline, management of consumables and inventories for lot numbers of consumables used in the treatment cycles, and generating reports.

2. The method as claimed in claim 1 further comprising the steps of:
   locating further RF transceiving devices corresponding to each of a hierarchy of laboratory apparatus for addressing the location of the biological sample within a laboratory environment.

3. The method as claimed in claim 1 wherein one or a combination of the step of interrogating and the RF transceiving device comprises at least one MEMS device.

4. The method as claimed in claim 1 wherein the RF transceiving device is adapted to transmit in situ environmental conditions of the biological sample in addition to identification signals unique to the biological sample.

5. Apparatus for tracing one or more biological samples at any location in an assisted reproductive technology (ART) laboratory environment in the course of performance of a task, comprising:
   an RF transceiving device adapted for location proximate a biological sample container wherein the RF transceiving device is encased in polymer that is resistant to a range of laboratory conditions including one or more of a cryo-environment and gamma irradiation;
   interrogation means comprising at least a portable reader device for interrogating the RF transceiving device for identification signals unique to the one or more biological samples; and
   tracking the location of the one or more biological samples based on the interrogation of the RF transceiving device and indexing the location in a centralised database;

wherein the interrogation device periodically interrogates the RF transceiving device and periodically tracks the location of the one or more biological samples during (i) a configuration process and (ii) a supervision process, the configuration process involving creating and editing labels for the one or more biological samples associated with a patient, creating label groups corresponding to ART treatment cycles, assigning labels to a development timeline in each treatment cycle, specifying critical labels and specifying critical activities to be undertaken in relation to the one or more samples;

the supervising process involving management of an active task list for the patient including progress of the biological sample against the development timeline, management of consumables and inventories for lot numbers of consumables used in the treatment cycles, and generating reports.

6. Apparatus as claimed in claim 5 wherein one or a combination of the RF transceiving device and the interrogation means comprises a MEMS construction.

7. The method as claimed in claim 1 wherein the biological samples are chosen from one or more of sperm, embryo, eggs and gametes.

8. The method as claimed in claim 4 wherein the biological samples are chosen from one or more of sperm, embryo, eggs and gametes.

9. The method as claimed in claim 1 wherein the method further comprises the steps of:

capturing data or information about one or a combination of;

an individual operator handling the biological samples, including the qualifications of the operator, identity of a patient corresponding to the biological samples, laboratory process steps, including timing of process steps, the environment and environmental parameters including temperature, humidity, $CO_2$ levels during the process steps, the operator's performance of the process steps, the location of biological samples, the lot numbers, batch numbers, expiry dates and other information about the materials and consumables used during the process steps, the equipment used, including their service, calibration and operational status, performing a comparison of the captured data or information with reference data;

generating one or a combination of at least one confirmation, warning or alarm depending on the outcome of the comparison, and;

capturing the generated confirmations, warnings or alarms to a separate record to be used for quality assurance and quality control auditing and training.

* * * * *